US010863920B2

(12) United States Patent
Bukhman et al.

(10) Patent No.: US 10,863,920 B2
(45) Date of Patent: *Dec. 15, 2020

(54) SYSTEMS AND METHODS FOR GUIDANCE AND PLACEMENT OF AN INTRAVASCULAR DEVICE

(71) Applicant: C. R. Bard, Inc., Murray Hill, NJ (US)

(72) Inventors: Vladislav Bukhman, East Northport, NY (US); Anthony K. Misener, Bountiful, UT (US); Valeriy Vassylyev, Kiev (UA); Robin S. Urry, Sandy, UT (US); Brian S. Tanner, Layton, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 364 days.

This patent is subject to a terminal disclaimer.

(21) Appl. No.: 15/836,741

(22) Filed: Dec. 8, 2017

(65) Prior Publication Data
US 2018/0103869 A1  Apr. 19, 2018

Related U.S. Application Data

(63) Continuation of application No. 14/615,932, filed on Feb. 6, 2015, now Pat. No. 9,839,372.
(Continued)

(51) Int. Cl.
*A61B 5/06* (2006.01)
*A61B 5/0452* (2006.01)
(Continued)

(52) U.S. Cl.
CPC .............. *A61B 5/062* (2013.01); *A61B 5/042* (2013.01); *A61B 5/0452* (2013.01);
(Continued)

(58) Field of Classification Search
CPC ..... A61B 5/062; A61B 5/065; A61B 5/04085; A61B 5/042; A61B 5/061; A61B 5/0452; A61B 8/085; A61B 8/0841
See application file for complete search history.

(56) References Cited

U.S. PATENT DOCUMENTS 3,133,244 A  5/1964  Wojtulewicz
3,297,020 A  1/1967  Mathiesen
(Continued)

FOREIGN PATENT DOCUMENTS

AU  642647 B2  10/1993
AU  1860597 B2  6/1999
(Continued)

OTHER PUBLICATIONS

Odd, DE et al, Does Radio-opaque Contrast Improve Radiographic localisation of Percutaneous Central Venous Lines?, Arch Dis Child Fetal Neonatal Ed, pp. 41-43, vol. 89 No. 1, Jan. 2004.
(Continued)

*Primary Examiner* — Sanjay Cattungal
(74) *Attorney, Agent, or Firm* — Rutan & Tucker LLP

(57) ABSTRACT

A guidance and placement system and associated methods for assisting a clinician in the placement of a catheter or other medical device within the vasculature of a patient is disclosed. In one embodiment, a method for guiding a medical device to a desired location within a vasculature of a patient is also disclosed and comprises detecting an intravascular ECG signal of the patient and identifying a P-wave of a waveform of the intravascular ECG signal, wherein the P-wave varies according to proximity of the medical device to the desired location. The method further comprises determining whether the identified P-wave is elevated, determining a deflection value of the identified P-wave when the identified P-wave is elevated, and reporting information relating to a location of the medical device
(Continued)

within the patient's vasculature at least partially according to the determined deflection value of the elevated P-wave.

25 Claims, 14 Drawing Sheets

Related U.S. Application Data

(60) Provisional application No. 61/936,825, filed on Feb. 6, 2014.

(51) Int. Cl.
*A61B 5/0408* (2006.01)
*A61B 5/042* (2006.01)
*A61B 8/08* (2006.01)

(52) U.S. Cl.
CPC .......... *A61B 5/04085* (2013.01); *A61B 5/061* (2013.01); *A61B 5/065* (2013.01); *A61B 8/085* (2013.01); *A61B 8/0841* (2013.01)

(56) References Cited

U.S. PATENT DOCUMENTS

| | | |
|---|---|---|
| 3,625,200 A | 12/1971 | Muller |
| 3,674,014 A | 7/1972 | Tillander |
| 3,795,855 A | 3/1974 | Browning |
| 3,817,241 A | 6/1974 | Grausz |
| 3,847,157 A | 11/1974 | Caillouette et al. |
| 3,868,565 A | 2/1975 | Kuipers |
| 3,896,373 A | 7/1975 | Zelby |
| 3,902,501 A | 9/1975 | Citron et al. |
| 3,986,373 A | 10/1976 | Goodlaxson |
| 3,995,623 A | 12/1976 | Blake et al. |
| 4,003,369 A | 1/1977 | Heilman et al. |
| 4,063,561 A | 12/1977 | McKenna |
| 4,072,146 A | 2/1978 | Howes |
| 4,114,601 A | 9/1978 | Abels |
| 4,149,535 A | 4/1979 | Volder |
| 4,173,228 A | 11/1979 | Van Steenwyk et al. |
| 4,175,566 A | 11/1979 | Millar |
| 4,181,120 A | 1/1980 | Kunii et al. |
| 4,224,949 A | 9/1980 | Scott et al. |
| 4,244,362 A | 1/1981 | Anderson |
| 4,289,139 A | 9/1981 | Enjoji et al. |
| 4,317,078 A | 2/1982 | Weed et al. |
| 4,327,722 A | 5/1982 | Groshong et al. |
| 4,327,723 A | 5/1982 | Frankhouser |
| 4,362,166 A | 12/1982 | Furler et al. |
| 4,365,639 A | 12/1982 | Goldreyer |
| 4,380,237 A | 4/1983 | Newbower |
| 4,407,294 A | 10/1983 | Vilkomerson |
| 4,417,886 A | 11/1983 | Frankhouser et al. |
| 4,429,693 A | 2/1984 | Blake et al. |
| 4,431,005 A | 2/1984 | McCormick |
| 4,431,214 A | 2/1984 | Buffington |
| 4,445,501 A | 5/1984 | Bresler |
| 4,459,854 A | 7/1984 | Richardson et al. |
| 4,469,106 A | 9/1984 | Harui |
| 4,483,343 A | 11/1984 | Beyer et al. |
| 4,491,137 A | 1/1985 | Jingu |
| 4,565,201 A | 1/1986 | Lass |
| 4,572,198 A | 2/1986 | Codrington |
| 4,577,634 A | 3/1986 | Gessman |
| 4,582,067 A | 4/1986 | Silverstein et al. |
| 4,587,975 A | 5/1986 | Salo et al. |
| 4,588,394 A | 5/1986 | Schulte et al. |
| 4,593,687 A | 6/1986 | Gray |
| 4,595,012 A | 6/1986 | Webler et al. |
| 4,601,706 A | 7/1986 | Aillon |
| 4,608,989 A | 9/1986 | Drue |
| 4,608,992 A | 9/1986 | Hakim et al. |
| 4,619,247 A | 10/1986 | Inoue et al. |
| 4,622,644 A | 11/1986 | Hansen |
| 4,644,960 A | 2/1987 | Johans |
| 4,652,820 A | 3/1987 | Maresca |
| 4,660,571 A | 4/1987 | Hess et al. |
| 4,665,925 A | 5/1987 | Millar |
| 4,667,230 A | 5/1987 | Arakawa et al. |
| 4,674,518 A | 6/1987 | Salo |
| 4,676,249 A | 6/1987 | Arenas et al. |
| 4,681,106 A | 7/1987 | Kensey et al. |
| 4,681,117 A | 7/1987 | Brodman et al. |
| 4,688,578 A | 8/1987 | Takano et al. |
| 4,692,148 A | 9/1987 | Kantrowitz et al. |
| 4,697,595 A | 10/1987 | Breyer et al. |
| 4,700,997 A | 10/1987 | Strand |
| 4,706,681 A | 11/1987 | Breyer et al. |
| 4,710,708 A | 12/1987 | Rorden et al. |
| 4,733,669 A | 3/1988 | Segal |
| 4,737,794 A | 4/1988 | Jones |
| 4,741,356 A | 5/1988 | Letzo et al. |
| 4,742,356 A | 5/1988 | Kuipers |
| 4,753,247 A | 6/1988 | Kirsner |
| 4,770,185 A | 9/1988 | Silverstein et al. |
| 4,771,788 A | 9/1988 | Millar |
| 4,781,685 A | 11/1988 | Lehmann et al. |
| 4,784,646 A | 11/1988 | Feingold |
| 4,787,070 A | 11/1988 | Suzuki et al. |
| 4,787,396 A | 11/1988 | Pidorenko |
| 4,790,809 A | 12/1988 | Kuntz |
| 4,793,361 A | 12/1988 | DuFault |
| 4,794,930 A | 1/1989 | Machida et al. |
| 4,796,632 A | 1/1989 | Boyd et al. |
| 4,798,588 A | 1/1989 | Aillon |
| 4,798,598 A | 1/1989 | Bonello et al. |
| 4,809,681 A | 3/1989 | Kantrowitz et al. |
| 4,809,713 A | 3/1989 | Grayzel |
| 4,813,729 A | 3/1989 | Speckhart |
| 4,821,731 A | 4/1989 | Martinelli et al. |
| 4,834,709 A | 5/1989 | Banning et al. |
| 4,836,214 A | 6/1989 | Sramek |
| 4,840,182 A | 6/1989 | Carlson |
| 4,840,622 A | 6/1989 | Hardy |
| 4,841,977 A | 6/1989 | Griffith et al. |
| 4,849,692 A | 7/1989 | Blood |
| 4,850,358 A | 7/1989 | Millar |
| 4,852,580 A | 8/1989 | Wood |
| 4,856,317 A | 8/1989 | Pidorenko et al. |
| 4,856,529 A | 8/1989 | Segal |
| 4,860,757 A | 8/1989 | Lynch et al. |
| 4,867,169 A | 9/1989 | Machida et al. |
| 4,869,263 A | 9/1989 | Segal et al. |
| 4,869,718 A | 9/1989 | Brader |
| 4,873,987 A | 10/1989 | Djordjevich et al. |
| 4,887,606 A | 12/1989 | Yock et al. |
| 4,887,615 A | 12/1989 | Taylor |
| 4,889,128 A | 12/1989 | Millar |
| 4,899,756 A | 2/1990 | Sonek |
| 4,901,725 A | 2/1990 | Nappholz et al. |
| 4,905,698 A | 3/1990 | Strohl, Jr. et al. |
| 4,911,173 A | 3/1990 | Terwilliger |
| 4,911,174 A | 3/1990 | Pederson et al. |
| 4,917,669 A | 4/1990 | Bonaldo |
| 4,924,870 A | 5/1990 | Wlodarczyk et al. |
| 4,943,770 A | 7/1990 | Ashley-Rollman et al. |
| 4,945,305 A | 7/1990 | Blood |
| 4,947,852 A | 8/1990 | Nassi et al. |
| 4,957,110 A | 9/1990 | Vogel et al. |
| 4,957,111 A | 9/1990 | Millar |
| 4,961,433 A | 10/1990 | Christian |
| 4,966,148 A | 10/1990 | Millar |
| 4,967,753 A | 11/1990 | Haase et al. |
| 4,977,886 A | 12/1990 | Takehana et al. |
| 4,989,608 A | 2/1991 | Ratner |
| 4,989,610 A | 2/1991 | Patton et al. |
| 4,995,396 A | 2/1991 | Inaba et al. |
| 4,998,916 A | 3/1991 | Hammerslag et al. |
| 5,004,456 A | 4/1991 | Botterbusch et al. |
| 5,005,592 A | 4/1991 | Cartmell |
| 5,016,173 A | 5/1991 | Kenet et al. |
| 5,025,799 A | 6/1991 | Wilson |
| 5,029,585 A | 7/1991 | Lieber et al. |

(56) References Cited

U.S. PATENT DOCUMENTS

| | | |
|---|---|---|
| 5,040,548 A | 8/1991 | Yock |
| 5,042,486 A | 8/1991 | Pfeiler et al. |
| 5,045,071 A | 9/1991 | McCormick et al. |
| 5,046,497 A | 9/1991 | Millar |
| 5,050,607 A | 9/1991 | Bradley et al. |
| 5,057,095 A | 10/1991 | Fabian |
| 5,058,583 A | 10/1991 | Geddes et al. |
| 5,058,595 A | 10/1991 | Kern |
| 5,067,489 A | 11/1991 | Lind |
| 5,076,278 A | 12/1991 | Vilkomerson et al. |
| 5,078,140 A | 1/1992 | Kwoh |
| 5,078,148 A | 1/1992 | Nassi et al. |
| 5,078,149 A | 1/1992 | Katsumata et al. |
| 5,078,678 A | 1/1992 | Katims |
| 5,078,714 A | 1/1992 | Katims |
| 5,084,022 A | 1/1992 | Claude |
| 5,092,341 A | 3/1992 | Kelen |
| 5,099,845 A | 3/1992 | Besz et al. |
| 5,099,850 A | 3/1992 | Matsui et al. |
| 5,100,387 A | 3/1992 | Ng |
| 5,105,829 A | 4/1992 | Fabian et al. |
| 5,109,862 A | 5/1992 | Kelen et al. |
| 5,114,401 A | 5/1992 | Stuart et al. |
| 5,121,750 A | 6/1992 | Katims |
| 5,125,410 A | 6/1992 | Misono et al. |
| 5,134,370 A | 7/1992 | Jefferts et al. |
| 5,144,955 A | 9/1992 | O'Hara |
| 5,146,151 A | 9/1992 | Korn |
| 5,156,151 A | 10/1992 | Imran |
| 5,158,086 A | 10/1992 | Brown et al. |
| 5,160,342 A | 11/1992 | Reger et al. |
| 5,161,536 A | 11/1992 | Vilkomerson et al. |
| 5,174,295 A | 12/1992 | Christian et al. |
| 5,174,299 A | 12/1992 | Nelson |
| 5,184,601 A | 2/1993 | Putman |
| 5,184,627 A | 2/1993 | de Toledo |
| 5,190,045 A | 3/1993 | Frazin |
| 5,202,985 A | 4/1993 | Goyal |
| 5,205,830 A | 4/1993 | Dassa et al. |
| 5,211,165 A | 5/1993 | Dumoulin et al. |
| 5,211,636 A | 5/1993 | Mische |
| 5,212,988 A | 5/1993 | White et al. |
| 5,214,615 A | 5/1993 | Bauer |
| 5,217,026 A | 6/1993 | Stoy et al. |
| 5,220,924 A | 6/1993 | Frazin |
| 5,233,994 A | 8/1993 | Shmulewitz |
| 5,235,987 A | 8/1993 | Wolfe |
| 5,239,464 A | 8/1993 | Blair et al. |
| 5,240,004 A | 8/1993 | Walinsky et al. |
| 5,243,995 A | 9/1993 | Maier |
| 5,246,007 A | 9/1993 | Frisbie et al. |
| 5,246,426 A | 9/1993 | Lewis et al. |
| 5,247,171 A | 9/1993 | Wlodarczyk et al. |
| 5,251,635 A | 10/1993 | Dumoulin et al. |
| 5,255,680 A | 10/1993 | Darrow et al. |
| 5,257,636 A | 11/1993 | White |
| 5,257,979 A | 11/1993 | Jagpal |
| 5,261,409 A | 11/1993 | Dardel |
| 5,265,610 A | 11/1993 | Darrow et al. |
| 5,265,614 A | 11/1993 | Hayakawa et al. |
| 5,267,569 A | 12/1993 | Lienhard |
| 5,269,306 A | 12/1993 | Warnking et al. |
| 5,270,810 A | 12/1993 | Nishimura |
| 5,271,404 A | 12/1993 | Corl et al. |
| 5,273,025 A | 12/1993 | Sakiyama et al. |
| 5,273,042 A | 12/1993 | Lynch et al. |
| 5,274,551 A | 12/1993 | Corby, Jr. |
| 5,275,053 A | 1/1994 | Wlodarczyk et al. |
| 5,279,129 A | 1/1994 | Ito |
| 5,279,607 A | 1/1994 | Schentag et al. |
| 5,280,786 A | 1/1994 | Wlodarczyk et al. |
| 5,287,331 A | 2/1994 | Schindel et al. |
| 5,289,373 A | 2/1994 | Zarge et al. |
| 5,292,342 A | 3/1994 | Nelson et al. |
| 5,307,072 A | 4/1994 | Jones, Jr. |
| 5,311,871 A | 5/1994 | Yock |
| 5,313,949 A | 5/1994 | Yock |
| 5,318,025 A | 6/1994 | Dumoulin et al. |
| 5,325,860 A | 7/1994 | Seward et al. |
| 5,325,873 A | 7/1994 | Hirschi et al. |
| 5,330,496 A | 7/1994 | Alferness |
| 5,331,966 A | 7/1994 | Bennett et al. |
| 5,333,614 A | 8/1994 | Feiring |
| 5,337,678 A | 8/1994 | Grout |
| 5,341,807 A | 8/1994 | Nardella |
| 5,343,865 A | 9/1994 | Gardineer et al. |
| 5,345,940 A | 9/1994 | Seward et al. |
| 5,348,020 A | 9/1994 | Hutson |
| 5,350,352 A | 9/1994 | Buchholtz et al. |
| 5,357,961 A | 10/1994 | Fields et al. |
| 5,365,935 A | 11/1994 | Righter et al. |
| 5,366,443 A | 11/1994 | Eggers et al. |
| 5,368,048 A | 11/1994 | Stoy et al. |
| 5,375,596 A | 12/1994 | Twiss et al. |
| 5,376,083 A | 12/1994 | Mische |
| 5,377,678 A | 1/1995 | Dumoulin et al. |
| 5,385,053 A | 1/1995 | Wlodarczyk et al. |
| 5,385,146 A | 1/1995 | Goldreyer |
| 5,391,199 A | 2/1995 | Ben-Haim |
| 5,394,876 A | 3/1995 | Ma |
| 5,394,877 A | 3/1995 | Orr et al. |
| 5,395,366 A | 3/1995 | D'Andrea et al. |
| 5,398,683 A | 3/1995 | Edwards et al. |
| 5,398,691 A | 3/1995 | Martin et al. |
| 5,411,485 A | 5/1995 | Tennican et al. |
| 5,413,107 A | 5/1995 | Oakley et al. |
| 5,417,208 A | 5/1995 | Winkler |
| 5,417,701 A | 5/1995 | Holmes |
| 5,422,478 A | 6/1995 | Wlodarczyk et al. |
| 5,423,334 A | 6/1995 | Jordan |
| 5,423,877 A | 6/1995 | Mackey |
| 5,425,367 A | 6/1995 | Shapiro et al. |
| 5,425,370 A | 6/1995 | Vilkomerson |
| 5,425,382 A | 6/1995 | Golden et al. |
| 5,427,114 A | 6/1995 | Colliver et al. |
| 5,429,132 A | 7/1995 | Guy et al. |
| 5,429,617 A | 7/1995 | Hammersmark et al. |
| 5,431,641 A | 7/1995 | Grozinger et al. |
| 5,433,729 A | 7/1995 | Adams et al. |
| 5,437,276 A | 8/1995 | Takada |
| 5,437,277 A | 8/1995 | Dumoulin et al. |
| 5,438,873 A | 8/1995 | Wlodarczyk et al. |
| 5,443,066 A | 8/1995 | Dumoulin et al. |
| 5,443,489 A | 8/1995 | Ben-Haim |
| 5,445,150 A | 8/1995 | Dumoulin et al. |
| 5,445,166 A | 8/1995 | Taylor |
| 5,450,846 A | 9/1995 | Goldreyer |
| 5,453,575 A | 9/1995 | O'Donnell et al. |
| 5,453,576 A | 9/1995 | Krivitski |
| 5,456,256 A | 10/1995 | Schneider et al. |
| 5,456,718 A | 10/1995 | Szymaitis |
| 5,464,016 A | 11/1995 | Nicholas et al. |
| 5,474,065 A | 12/1995 | Meathrel et al. |
| 5,476,090 A | 12/1995 | Kishi |
| 5,480,422 A | 1/1996 | Ben-Haim |
| 5,487,729 A | 1/1996 | Avellanet et al. |
| 5,490,522 A | 2/1996 | Dardel |
| 5,492,538 A | 2/1996 | Johlin, Jr. |
| 5,494,038 A | 2/1996 | Wang et al. |
| 5,500,011 A | 3/1996 | Desai |
| 5,500,012 A | 3/1996 | Brucker et al. |
| 5,505,205 A | 4/1996 | Solomon et al. |
| 5,509,822 A | 4/1996 | Negus et al. |
| 5,513,637 A | 5/1996 | Twiss et al. |
| 5,515,160 A | 5/1996 | Schulz et al. |
| 5,515,853 A | 5/1996 | Smith et al. |
| 5,517,989 A | 5/1996 | Frisbie et al. |
| 5,522,878 A | 6/1996 | Montecalvo et al. |
| 5,522,880 A | 6/1996 | Barone et al. |
| 5,526,812 A | 6/1996 | Dumoulin et al. |
| 5,531,664 A | 7/1996 | Adachi et al. |
| 5,536,248 A | 7/1996 | Weaver et al. |
| 5,540,230 A | 7/1996 | Vilkomerson |
| 5,540,681 A | 7/1996 | Strul et al. |

(56) References Cited

U.S. PATENT DOCUMENTS

| | | |
|---|---|---|
| 5,542,938 A | 8/1996 | Avellanet et al. |
| 5,546,949 A | 8/1996 | Frazin et al. |
| 5,546,951 A | 8/1996 | Ben-Haim |
| 5,555,618 A | 9/1996 | Winkler |
| 5,558,091 A | 9/1996 | Acker et al. |
| 5,568,809 A | 10/1996 | Ben-haim |
| D375,450 S | 11/1996 | Bidwell et al. |
| 5,570,671 A | 11/1996 | Hickey |
| 5,575,291 A | 11/1996 | Hayakawa et al. |
| 5,588,442 A | 12/1996 | Scovil et al. |
| 5,592,939 A | 1/1997 | Martinelli |
| 5,598,846 A | 2/1997 | Peszynski |
| 5,599,299 A | 2/1997 | Weaver et al. |
| 5,600,330 A | 2/1997 | Blood |
| 5,603,333 A | 2/1997 | Konings |
| 5,606,981 A | 3/1997 | Tartacower et al. |
| 5,610,967 A | 3/1997 | Moorman et al. |
| 5,617,866 A | 4/1997 | Marian, Jr. |
| 5,622,169 A | 4/1997 | Golden et al. |
| 5,622,170 A | 4/1997 | Schulz |
| 5,622,184 A | 4/1997 | Ashby et al. |
| 5,623,931 A | 4/1997 | Wung et al. |
| 5,624,430 A | 4/1997 | Eton et al. |
| 5,626,554 A | 5/1997 | Ryaby et al. |
| 5,626,870 A | 5/1997 | Monshipouri et al. |
| 5,630,419 A | 5/1997 | Ranalletta |
| 5,638,819 A | 6/1997 | Manwaring et al. |
| 5,640,967 A | 6/1997 | Fine et al. |
| 5,644,612 A | 7/1997 | Moorman et al. |
| 5,645,065 A | 7/1997 | Shapiro et al. |
| 5,651,047 A | 7/1997 | Moorman et al. |
| 5,654,864 A | 8/1997 | Ritter et al. |
| D383,968 S | 9/1997 | Bidwell et al. |
| 5,662,115 A | 9/1997 | Torp et al. |
| 5,665,103 A | 9/1997 | Lafontaine et al. |
| 5,665,477 A | 9/1997 | Meathrel et al. |
| 5,666,473 A | 9/1997 | Wallace |
| 5,666,958 A | 9/1997 | Rothenberg et al. |
| 5,669,383 A | 9/1997 | Johnson |
| 5,669,388 A | 9/1997 | Vilkomerson |
| 5,676,159 A | 10/1997 | Navis |
| 5,676,673 A | 10/1997 | Ferre et al. |
| 5,682,890 A | 11/1997 | Kormos et al. |
| 5,691,898 A | 11/1997 | Rosenberg et al. |
| 5,694,945 A | 12/1997 | Ben-Haim |
| 5,695,479 A | 12/1997 | Jagpal |
| 5,697,377 A | 12/1997 | Wittkampf |
| 5,699,801 A | 12/1997 | Atalar et al. |
| 5,700,889 A | 12/1997 | Blair |
| 5,701,898 A | 12/1997 | Adam et al. |
| 5,702,433 A | 12/1997 | Taylor et al. |
| 5,711,299 A | 1/1998 | Manwaring et al. |
| 5,713,362 A | 2/1998 | Vilkomerson |
| 5,713,363 A | 2/1998 | Seward et al. |
| 5,713,858 A | 2/1998 | Heruth et al. |
| 5,713,946 A | 2/1998 | Ben-Haim |
| 5,715,817 A | 2/1998 | Stevens-Wright et al. |
| 5,716,389 A | 2/1998 | Walinsky et al. |
| 5,718,241 A | 2/1998 | Ben-Haim et al. |
| D391,838 S | 3/1998 | Bidwell et al. |
| 5,722,412 A | 3/1998 | Pflugrath et al. |
| 5,727,550 A | 3/1998 | Montecalvo |
| 5,727,552 A | 3/1998 | Ryan |
| 5,727,553 A | 3/1998 | Saad |
| 5,729,055 A | 3/1998 | Manning |
| 5,729,129 A | 3/1998 | Acker |
| 5,729,584 A | 3/1998 | Moorman et al. |
| 5,730,129 A | 3/1998 | Darrow et al. |
| 5,731,996 A | 3/1998 | Gilbert |
| 5,733,323 A | 3/1998 | Buck et al. |
| 5,738,096 A | 4/1998 | Ben-Haim |
| 5,740,808 A | 4/1998 | Panescu et al. |
| 5,742,394 A | 4/1998 | Hansen |
| 5,744,953 A | 4/1998 | Hansen |
| 5,748,767 A | 5/1998 | Raab |
| 5,749,835 A | 5/1998 | Glantz |
| 5,749,938 A | 5/1998 | Coombs |
| 5,751,785 A | 5/1998 | Moorman et al. |
| 5,752,513 A | 5/1998 | Acker et al. |
| 5,758,650 A | 6/1998 | Miller et al. |
| 5,762,064 A | 6/1998 | Polvani |
| 5,767,669 A | 6/1998 | Hansen et al. |
| 5,767,960 A | 6/1998 | Orman |
| 5,769,786 A | 6/1998 | Wiegel |
| 5,769,843 A | 6/1998 | Abela et al. |
| 5,769,881 A | 6/1998 | Schroeppel et al. |
| 5,771,896 A | 6/1998 | Sliwa, Jr. et al. |
| 5,775,322 A | 7/1998 | Silverstein et al. |
| 5,775,332 A | 7/1998 | Goldman |
| 5,776,064 A | 7/1998 | Kalfas et al. |
| 5,776,080 A | 7/1998 | Thome et al. |
| 5,779,638 A | 7/1998 | Vesely et al. |
| 5,782,767 A | 7/1998 | Pretlow, III |
| 5,782,773 A | 7/1998 | Kuo et al. |
| 5,785,657 A | 7/1998 | Breyer et al. |
| 5,792,055 A | 8/1998 | McKinnon |
| 5,795,297 A | 8/1998 | Daigle |
| 5,795,298 A | 8/1998 | Vesely et al. |
| 5,795,632 A | 8/1998 | Buchalter |
| 5,797,849 A | 8/1998 | Vesely et al. |
| 5,800,352 A | 9/1998 | Ferre et al. |
| 5,800,410 A | 9/1998 | Gawreluk |
| 5,800,497 A | 9/1998 | Bakels et al. |
| 5,803,089 A | 9/1998 | Ferre et al. |
| 5,810,733 A | 9/1998 | Van Creveld et al. |
| RE35,924 E | 10/1998 | Winkler |
| 5,817,022 A | 10/1998 | Vesely |
| 5,817,024 A | 10/1998 | Ogle et al. |
| 5,820,549 A | 10/1998 | Marian, Jr. |
| 5,820,560 A | 10/1998 | Sinderby et al. |
| 5,824,031 A | 10/1998 | Cookston et al. |
| 5,827,192 A | 10/1998 | Gopakumaran et al. |
| 5,829,444 A | 11/1998 | Ferre et al. |
| 5,830,145 A | 11/1998 | Tenhoff |
| 5,831,260 A | 11/1998 | Hansen |
| 5,833,608 A | 11/1998 | Acker |
| 5,833,622 A | 11/1998 | Meathrel et al. |
| 5,835,561 A | 11/1998 | Moorman et al. |
| 5,836,882 A | 11/1998 | Frazin |
| 5,836,990 A | 11/1998 | Li |
| 5,840,024 A | 11/1998 | Taniguchi et al. |
| 5,840,025 A | 11/1998 | Ben-Haim |
| 5,840,030 A | 11/1998 | Ferek-Petric et al. |
| 5,840,031 A | 11/1998 | Crowley |
| 5,842,986 A | 12/1998 | Avrin et al. |
| 5,842,998 A | 12/1998 | Gopakumaran et al. |
| 5,843,076 A | 12/1998 | Webster, Jr. et al. |
| 5,843,153 A | 12/1998 | Johnston et al. |
| 5,844,140 A | 12/1998 | Seale |
| 5,846,198 A | 12/1998 | Killmann |
| 5,855,553 A | 1/1999 | Tajima et al. |
| 5,859,893 A | 1/1999 | Moorman et al. |
| 5,865,748 A | 2/1999 | Co et al. |
| 5,868,673 A | 2/1999 | Vesely |
| 5,873,822 A | 2/1999 | Ferre et al. |
| 5,876,328 A | 3/1999 | Fox et al. |
| 5,879,297 A | 3/1999 | Haynor et al. |
| 5,893,363 A | 4/1999 | Little et al. |
| 5,897,495 A | 4/1999 | Aida et al. |
| 5,899,860 A | 5/1999 | Pfeiffer et al. |
| 5,902,238 A | 5/1999 | Golden et al. |
| 5,907,487 A | 5/1999 | Rosenberg et al. |
| 5,908,385 A | 6/1999 | Chechelski et al. |
| 5,910,113 A | 6/1999 | Pruter |
| 5,910,120 A | 6/1999 | Kim et al. |
| 5,913,820 A | 6/1999 | Bladen et al. |
| 5,913,830 A | 6/1999 | Miles |
| 5,919,141 A | 7/1999 | Money et al. |
| 5,919,170 A | 7/1999 | Woessner |
| 5,928,145 A | 7/1999 | Ocali et al. |
| 5,929,607 A | 7/1999 | Rosenberg et al. |
| 5,931,788 A | 8/1999 | Keen et al. |
| 5,931,818 A | 8/1999 | Werp et al. |
| 5,931,863 A | 8/1999 | Griffin, III et al. |

(56) References Cited

U.S. PATENT DOCUMENTS

| | | |
|---|---|---|
| 5,935,160 A | 8/1999 | Auricchio et al. |
| 5,941,858 A | 8/1999 | Johnson |
| 5,941,889 A | 8/1999 | Cermak |
| 5,941,904 A | 8/1999 | Johnston et al. |
| 5,944,022 A | 8/1999 | Nardella et al. |
| 5,944,023 A | 8/1999 | Johnson et al. |
| 5,951,472 A | 9/1999 | Van Vaals et al. |
| 5,951,598 A | 9/1999 | Bishay et al. |
| 5,953,683 A | 9/1999 | Hansen et al. |
| 5,957,857 A | 9/1999 | Hartley |
| 5,961,923 A | 10/1999 | Nova et al. |
| 5,967,978 A | 10/1999 | Littmann et al. |
| 5,967,980 A | 10/1999 | Ferre et al. |
| 5,967,991 A | 10/1999 | Gardineer et al. |
| 5,969,722 A | 10/1999 | Palm |
| 5,971,933 A | 10/1999 | Gopakumaran et al. |
| 5,971,983 A | 10/1999 | Lesh |
| 5,978,705 A | 11/1999 | KenKnight et al. |
| 5,983,126 A | 11/1999 | Wittkampf |
| 5,984,908 A | 11/1999 | Davis et al. |
| 5,991,693 A | 11/1999 | Zalewski |
| 5,997,473 A | 12/1999 | Taniguchi et al. |
| 5,997,481 A | 12/1999 | Adams et al. |
| 6,006,123 A | 12/1999 | Nguyen et al. |
| 6,011,988 A | 1/2000 | Lynch et al. |
| 6,014,473 A | 1/2000 | Hossack et al. |
| 6,014,580 A | 1/2000 | Blume et al. |
| 6,015,414 A | 1/2000 | Werp et al. |
| 6,017,496 A | 1/2000 | Nova et al. |
| 6,019,724 A | 2/2000 | Gronningsaeter et al. |
| 6,019,725 A | 2/2000 | Vesely et al. |
| 6,022,342 A | 2/2000 | Mukherjee |
| 6,023,638 A | 2/2000 | Swanson |
| 6,026,312 A | 2/2000 | Shemwell et al. |
| 6,031,765 A | 2/2000 | Lee et al. |
| 6,032,070 A | 2/2000 | Flock et al. |
| 6,039,694 A | 3/2000 | Larson et al. |
| 6,050,718 A | 4/2000 | Schena et al. |
| 6,052,610 A | 4/2000 | Koch |
| 6,052,618 A | 4/2000 | Dahlke et al. |
| D424,693 S | 5/2000 | Pruter |
| 6,058,323 A | 5/2000 | Lemelson |
| 6,059,718 A | 5/2000 | Taniguchi et al. |
| 6,063,032 A | 5/2000 | Grunwald |
| 6,064,905 A | 5/2000 | Webster, Jr. et al. |
| 6,066,094 A | 5/2000 | Ben-Haim |
| 6,068,599 A | 5/2000 | Saito et al. |
| 6,073,043 A | 6/2000 | Schneider |
| 6,074,367 A | 6/2000 | Hubbell |
| 6,075,442 A | 6/2000 | Welch |
| 6,076,007 A | 6/2000 | England et al. |
| 6,081,737 A | 6/2000 | Shah |
| 6,082,366 A | 7/2000 | Andra et al. |
| 6,083,170 A | 7/2000 | Ben-Haim |
| 6,099,524 A | 8/2000 | Lipson et al. |
| 6,100,026 A | 8/2000 | Nova et al. |
| 6,102,044 A | 8/2000 | Naidyhorski |
| 6,102,862 A | 8/2000 | Grunwald et al. |
| 6,107,699 A | 8/2000 | Swanson |
| 6,112,111 A | 8/2000 | Glantz |
| 6,112,115 A | 8/2000 | Feldman et al. |
| 6,113,504 A | 9/2000 | Kuesters |
| 6,115,624 A | 9/2000 | Lewis et al. |
| 6,120,445 A | 9/2000 | Grunwald |
| 6,122,538 A | 9/2000 | Sliwa, Jr. et al. |
| 6,128,174 A | 10/2000 | Ritter et al. |
| 6,129,668 A | 10/2000 | Haynor et al. |
| 6,129,724 A | 10/2000 | Fleischman et al. |
| 6,132,378 A | 10/2000 | Marino |
| 6,132,379 A | 10/2000 | Patacsil et al. |
| 6,135,961 A | 10/2000 | Pflugrath et al. |
| 6,136,274 A | 10/2000 | Nova et al. |
| 6,138,681 A | 10/2000 | Chen et al. |
| 6,139,496 A | 10/2000 | Chen et al. |
| 6,139,502 A | 10/2000 | Fredriksen |
| 6,139,540 A | 10/2000 | Rost et al. |
| 6,144,300 A | 11/2000 | Dames |
| 6,148,823 A | 11/2000 | Hastings |
| 6,152,933 A | 11/2000 | Werp et al. |
| 6,157,853 A | 12/2000 | Blume et al. |
| 6,165,144 A | 12/2000 | Talish et al. |
| 6,165,977 A | 12/2000 | Mochly-Rosen |
| 6,166,496 A | 12/2000 | Lys et al. |
| 6,166,806 A | 12/2000 | Tjin |
| 6,167,765 B1 | 1/2001 | Weitzel |
| 6,172,499 B1 | 1/2001 | Ashe |
| 6,173,199 B1 | 1/2001 | Gabriel |
| 6,173,715 B1 | 1/2001 | Sinanan et al. |
| 6,175,756 B1 | 1/2001 | Ferre et al. |
| 6,176,829 B1 | 1/2001 | Vilkomerson |
| 6,187,744 B1 | 2/2001 | Rooney |
| 6,190,370 B1 | 2/2001 | Tsui |
| 6,191,136 B1 | 2/2001 | Marban |
| 6,193,743 B1 | 2/2001 | Brayton et al. |
| 6,197,001 B1 | 3/2001 | Wilson et al. |
| 6,200,305 B1 | 3/2001 | Berthiaume et al. |
| 6,203,499 B1 | 3/2001 | Imling et al. |
| 6,208,884 B1 | 3/2001 | Kumar et al. |
| 6,211,626 B1 | 4/2001 | Lys et al. |
| 6,211,666 B1 | 4/2001 | Acker |
| 6,212,426 B1 | 4/2001 | Swanson |
| 6,212,430 B1 | 4/2001 | Kung |
| 6,216,027 B1 | 4/2001 | Willis et al. |
| 6,216,028 B1 | 4/2001 | Haynor et al. |
| 6,216,029 B1 | 4/2001 | Paltieli |
| 6,217,517 B1 | 4/2001 | Grunwald |
| 6,223,087 B1 | 4/2001 | Williams |
| 6,226,547 B1 | 5/2001 | Lockhart et al. |
| 6,230,042 B1 | 5/2001 | Slettenmark |
| 6,230,046 B1 | 5/2001 | Crane et al. |
| 6,231,518 B1 | 5/2001 | Grabek et al. |
| 6,233,476 B1 | 5/2001 | Strommer et al. |
| 6,233,994 B1 | 5/2001 | Roy et al. |
| 6,236,883 B1 | 5/2001 | Ciaccio et al. |
| 6,238,344 B1 | 5/2001 | Gamelsky et al. |
| 6,241,673 B1 | 6/2001 | Williams |
| 6,246,231 B1 | 6/2001 | Ashe |
| 6,246,898 B1 | 6/2001 | Vesely et al. |
| 6,248,072 B1 | 6/2001 | Murkin |
| 6,248,074 B1 | 6/2001 | Ohno et al. |
| 6,248,075 B1 | 6/2001 | McGee et al. |
| 6,249,234 B1 | 6/2001 | Ely et al. |
| 6,253,770 B1 | 7/2001 | Acker et al. |
| 6,254,543 B1 | 7/2001 | Grunwald et al. |
| 6,258,035 B1 | 7/2001 | Hoeksel et al. |
| 6,259,938 B1 | 7/2001 | Zarychta et al. |
| 6,259,941 B1 | 7/2001 | Chia et al. |
| 6,261,231 B1 | 7/2001 | Damphousse et al. |
| 6,263,230 B1 | 7/2001 | Haynor et al. |
| 6,266,550 B1 | 7/2001 | Selmon et al. |
| 6,266,551 B1 | 7/2001 | Osadchy et al. |
| 6,266,552 B1 | 7/2001 | Slettenmark |
| 6,266,563 B1 | 7/2001 | KenKnight et al. |
| 6,270,493 B1 | 8/2001 | Lalonde et al. |
| 6,271,833 B1 | 8/2001 | Rosenberg et al. |
| 6,272,371 B1 | 8/2001 | Shlomo |
| 6,272,374 B1 | 8/2001 | Flock et al. |
| 6,275,258 B1 | 8/2001 | Chim |
| 6,275,724 B1 | 8/2001 | Dickinson et al. |
| 6,277,077 B1 | 8/2001 | Brisken et al. |
| 6,284,459 B1 | 9/2001 | Nova et al. |
| 6,285,898 B1 | 9/2001 | Ben-Haim |
| 6,287,259 B1 | 9/2001 | Grunwald |
| 6,287,260 B1 | 9/2001 | Hascoet et al. |
| 6,288,704 B1 | 9/2001 | Flack et al. |
| 6,292,678 B1 | 9/2001 | Hall et al. |
| 6,292,680 B1 | 9/2001 | Somogyi et al. |
| 6,292,901 B1 | 9/2001 | Lys et al. |
| 6,293,955 B1 | 9/2001 | Houser et al. |
| 6,296,604 B1 | 10/2001 | Garibaldi et al. |
| 6,298,261 B1 | 10/2001 | Rex |
| 6,304,768 B1 | 10/2001 | Blume et al. |
| 6,306,097 B1 | 10/2001 | Park et al. |
| 6,306,105 B1 | 10/2001 | Rooney et al. |

(56) References Cited

U.S. PATENT DOCUMENTS

| | | |
|---|---|---|
| 6,311,082 B1 | 10/2001 | Creighton, IV et al. |
| 6,315,709 B1 | 11/2001 | Garibaldi et al. |
| 6,315,727 B1 | 11/2001 | Coleman et al. |
| 6,319,668 B1 | 11/2001 | Nova et al. |
| 6,323,769 B1 | 11/2001 | Dames |
| 6,323,770 B1 | 11/2001 | Dames |
| 6,324,416 B1 | 11/2001 | Seibert |
| 6,325,540 B1 | 12/2001 | Lounsberry et al. |
| 6,325,762 B1 | 12/2001 | Tjin |
| 6,329,139 B1 | 12/2001 | Nova et al. |
| 6,329,916 B1 | 12/2001 | Dames |
| 6,330,467 B1 | 12/2001 | Creighton, IV et al. |
| 6,332,089 B1 | 12/2001 | Acker et al. |
| 6,332,874 B1 | 12/2001 | Eliasen et al. |
| 6,340,588 B1 | 1/2002 | Nova et al. |
| 6,340,868 B1 | 1/2002 | Lys et al. |
| 6,341,231 B1 | 1/2002 | Ferre et al. |
| 6,346,081 B1 | 2/2002 | Vilkomerson |
| 6,348,911 B1 | 2/2002 | Rosenberg et al. |
| 6,350,160 B1 | 2/2002 | Feuersanger et al. |
| 6,352,363 B1 | 3/2002 | Munger et al. |
| 6,354,999 B1 | 3/2002 | Dgany et al. |
| 6,355,026 B1 | 3/2002 | Mick |
| 6,356,791 B1 | 3/2002 | Westlund et al. |
| 6,360,123 B1 | 3/2002 | Kimchi et al. |
| 6,361,499 B1 | 3/2002 | Bates et al. |
| 6,364,823 B1 | 4/2002 | Garibaldi et al. |
| 6,364,839 B1 | 4/2002 | Little et al. |
| 6,366,804 B1 | 4/2002 | Mejia |
| 6,368,285 B1 | 4/2002 | Osadchy et al. |
| 6,370,411 B1 | 4/2002 | Osadchy et al. |
| 6,373,240 B1 | 4/2002 | Govari |
| 6,373,388 B1 | 4/2002 | Dames |
| 6,374,134 B1 | 4/2002 | Bladen et al. |
| 6,374,670 B1 | 4/2002 | Spelman et al. |
| 6,375,606 B1 | 4/2002 | Garibaldi et al. |
| 6,375,639 B1 | 4/2002 | Duplessie et al. |
| 6,377,857 B1 | 4/2002 | Brayton et al. |
| 6,379,302 B1 | 4/2002 | Kessman et al. |
| 6,379,303 B1 | 4/2002 | Seitz et al. |
| 6,379,307 B1 | 4/2002 | Filly et al. |
| 6,381,485 B1 | 4/2002 | Hunter et al. |
| 6,385,472 B1 | 5/2002 | Hall et al. |
| 6,385,476 B1 | 5/2002 | Osadchy et al. |
| 6,398,736 B1 | 6/2002 | Seward |
| 6,398,738 B1 | 6/2002 | Millar |
| 6,401,723 B1 | 6/2002 | Garibaldi et al. |
| 6,406,422 B1 | 6/2002 | Landesberg |
| 6,406,442 B1 | 6/2002 | McFann et al. |
| 6,412,978 B1 | 7/2002 | Watanabe et al. |
| 6,412,980 B1 | 7/2002 | Lounsberry et al. |
| 6,417,839 B1 | 7/2002 | Odell |
| 6,418,332 B1 | 7/2002 | Mastrototaro et al. |
| 6,418,335 B2 | 7/2002 | Avrin et al. |
| 6,423,002 B1 | 7/2002 | Hossack |
| 6,423,050 B1 | 7/2002 | Twardowski |
| 6,427,079 B1 | 7/2002 | Schneider et al. |
| 6,428,551 B1 | 8/2002 | Hall et al. |
| 6,430,315 B1 | 8/2002 | Makram-Ebeid |
| 6,432,069 B1 | 8/2002 | Godo et al. |
| 6,438,411 B1 | 8/2002 | Guttman et al. |
| 6,442,416 B1 | 8/2002 | Schultz |
| 6,445,943 B1 | 9/2002 | Ferre et al. |
| 6,456,874 B1 | 9/2002 | Hafer et al. |
| 6,459,919 B1 | 10/2002 | Lys et al. |
| 6,463,121 B1 | 10/2002 | Milnes |
| 6,466,815 B1 | 10/2002 | Saito et al. |
| 6,471,656 B1 | 10/2002 | Shalman et al. |
| 6,471,658 B1 | 10/2002 | Daniels et al. |
| 6,471,700 B1 | 10/2002 | Burbank et al. |
| 6,473,167 B1 | 10/2002 | Odell |
| 6,474,341 B1 | 11/2002 | Hunter et al. |
| 6,475,152 B1 | 11/2002 | Kelly, Jr. et al. |
| 6,475,223 B1 | 11/2002 | Werp et al. |
| 6,477,402 B1 | 11/2002 | Lynch et al. |
| 6,484,118 B1 | 11/2002 | Govari |
| 6,487,916 B1 | 12/2002 | Gomm et al. |
| 6,491,671 B1 | 12/2002 | Larson, III et al. |
| 6,493,573 B1 | 12/2002 | Martinelli et al. |
| 6,494,832 B1 | 12/2002 | Feldman et al. |
| 6,496,715 B1 | 12/2002 | Lee et al. |
| 6,498,944 B1 | 12/2002 | Ben-Haim et al. |
| 6,500,141 B1 | 12/2002 | Irion et al. |
| 6,505,062 B1 | 1/2003 | Ritter et al. |
| 6,506,159 B2 | 1/2003 | Hascoet et al. |
| 6,507,751 B2 | 1/2003 | Blume et al. |
| 6,508,802 B1 | 1/2003 | Rosengart et al. |
| 6,511,413 B2 | 1/2003 | Landesberg |
| 6,512,958 B1 | 1/2003 | Swoyer et al. |
| 6,514,202 B2 | 2/2003 | Grunwald |
| 6,514,226 B1 | 2/2003 | Levin et al. |
| 6,514,249 B1 | 2/2003 | Maguire et al. |
| 6,515,657 B1 | 2/2003 | Lanelli |
| 6,516,212 B1 | 2/2003 | Bladen et al. |
| 6,516,231 B1 | 2/2003 | Flammang |
| 6,516,807 B2 | 2/2003 | Panescu et al. |
| 6,517,520 B2 | 2/2003 | Chang et al. |
| 6,522,906 B1 | 2/2003 | Salisbury, Jr. et al. |
| 6,522,907 B1 | 2/2003 | Bladen et al. |
| 6,522,909 B1 | 2/2003 | Garibaldi et al. |
| 6,524,303 B1 | 2/2003 | Garibaldi |
| 6,528,954 B1 | 3/2003 | Lys et al. |
| 6,528,991 B2 | 3/2003 | Ashe |
| 6,529,761 B2 | 3/2003 | Creighton, IV et al. |
| 6,529,766 B1 | 3/2003 | Guendel |
| 6,534,982 B1 | 3/2003 | Jakab |
| 6,535,625 B1 | 3/2003 | Chang et al. |
| 6,537,192 B1 | 3/2003 | Elliott et al. |
| 6,537,196 B1 | 3/2003 | Creighton, IV et al. |
| 6,538,634 B1 | 3/2003 | Chui et al. |
| 6,540,699 B1 | 4/2003 | Smith |
| 6,542,766 B2 | 4/2003 | Hall et al. |
| 6,544,251 B1 | 4/2003 | Crawford |
| 6,545,678 B1 | 4/2003 | Ohazama |
| 6,546,270 B1 | 4/2003 | Goldin et al. |
| 6,546,279 B1 | 4/2003 | Bova et al. |
| 6,546,787 B1 | 4/2003 | Schiller et al. |
| 6,552,841 B1 | 4/2003 | Lasser et al. |
| 6,556,858 B1 | 4/2003 | Zeman |
| 6,562,019 B1 | 5/2003 | Sell |
| 6,564,087 B1 | 5/2003 | Pitris et al. |
| 6,569,101 B2 | 5/2003 | Quistgaard et al. |
| 6,569,103 B2 | 5/2003 | Hoeksel et al. |
| 6,569,160 B1 | 5/2003 | Goldin et al. |
| 6,569,862 B1 | 5/2003 | Marban |
| 6,571,004 B1 | 5/2003 | Florent et al. |
| 6,574,518 B1 | 6/2003 | Lounsberry et al. |
| 6,575,908 B2 | 6/2003 | Barnes et al. |
| 6,577,080 B2 | 6/2003 | Lys et al. |
| 6,577,896 B2 | 6/2003 | Werner et al. |
| 6,584,343 B1 | 6/2003 | Ransbury et al. |
| 6,589,181 B2 | 7/2003 | Grunwald et al. |
| 6,593,754 B1 | 7/2003 | Steber et al. |
| 6,593,884 B1 | 7/2003 | Gilboa et al. |
| 6,597,943 B2 | 7/2003 | Taha et al. |
| 6,599,249 B1 | 7/2003 | Nordgren et al. |
| 6,607,488 B1 | 8/2003 | Jackson et al. |
| 6,610,058 B2 | 8/2003 | Flores |
| 6,611,141 B1 | 8/2003 | Schulz et al. |
| 6,615,071 B1 | 9/2003 | Casscells, III et al. |
| 6,615,155 B2 | 9/2003 | Gilboa |
| 6,616,610 B2 | 9/2003 | Steininger et al. |
| 6,618,612 B1 | 9/2003 | Acker et al. |
| 6,626,832 B1 | 9/2003 | Paltieli et al. |
| 6,626,834 B2 | 9/2003 | Dunne et al. |
| 6,626,902 B1 | 9/2003 | Kucharczyk et al. |
| 6,630,879 B1 | 10/2003 | Creighton, IV et al. |
| 6,635,027 B1 | 10/2003 | Cragg et al. |
| 6,645,148 B2 | 11/2003 | Nguyen-Dinh et al. |
| 6,648,875 B2 | 11/2003 | Simpson et al. |
| 6,649,914 B1 | 11/2003 | Moorman et al. |
| 6,652,505 B1 | 11/2003 | Tsugita |
| 6,652,506 B2 | 11/2003 | Bowe et al. |
| 6,660,024 B1 | 12/2003 | Flaherty et al. |

(56) References Cited

U.S. PATENT DOCUMENTS

| | | |
|---|---|---|
| 6,662,034 B2 | 12/2003 | Segner et al. |
| 6,663,661 B2 | 12/2003 | Boneau |
| 6,666,828 B2 | 12/2003 | Greco et al. |
| 6,672,308 B1 | 1/2004 | Gaspari |
| 6,677,752 B1 | 1/2004 | Creighton, IV et al. |
| 6,679,857 B1 | 1/2004 | Bastia et al. |
| 6,684,176 B2 | 1/2004 | Willins et al. |
| 6,685,644 B2 | 2/2004 | Seo et al. |
| 6,687,531 B1 | 2/2004 | Ferre et al. |
| 6,689,119 B1 | 2/2004 | Di Caprio et al. |
| 6,690,963 B2 | 2/2004 | Ben-Haim et al. |
| 6,690,964 B2 | 2/2004 | Bieger et al. |
| 6,690,968 B2 | 2/2004 | Mejia |
| 6,694,167 B1 | 2/2004 | Ferre et al. |
| 6,695,786 B2 | 2/2004 | Wang et al. |
| 6,701,179 B1 | 3/2004 | Martinelli et al. |
| 6,701,918 B2 | 3/2004 | Fariss et al. |
| 6,702,804 B1 | 3/2004 | Ritter et al. |
| 6,704,590 B2 | 3/2004 | Haldeman |
| 6,709,390 B1 | 3/2004 | Marie Pop |
| 6,711,429 B1 | 3/2004 | Gilboa et al. |
| 6,711,431 B2 | 3/2004 | Sarin et al. |
| 6,719,699 B2 | 4/2004 | Smith |
| 6,719,724 B1 | 4/2004 | Walker et al. |
| 6,719,756 B1 | 4/2004 | Muntermann |
| 6,720,745 B2 | 4/2004 | Lys et al. |
| 6,733,458 B1 | 5/2004 | Steins et al. |
| 6,733,473 B1 | 5/2004 | Reifart et al. |
| 6,733,511 B2 | 5/2004 | Hall et al. |
| 6,736,782 B2 | 5/2004 | Pfeiffer et al. |
| 6,738,656 B1 | 5/2004 | Ferre et al. |
| 6,740,103 B2 | 5/2004 | Hall et al. |
| 6,743,177 B2 | 6/2004 | Ito |
| 6,754,596 B2 | 6/2004 | Ashe |
| 6,755,789 B2 | 6/2004 | Stringer et al. |
| 6,755,816 B2 | 6/2004 | Ritter et al. |
| 6,755,822 B2 | 6/2004 | Reu et al. |
| 6,757,557 B1 | 6/2004 | Bladen et al. |
| 6,763,261 B2 | 7/2004 | Casscells, III et al. |
| 6,764,449 B2 | 7/2004 | Lee et al. |
| 6,768,496 B2 | 7/2004 | Bieger et al. |
| 6,772,001 B2 | 8/2004 | Maschke |
| 6,774,624 B2 | 8/2004 | Anderson et al. |
| 6,783,536 B2 | 8/2004 | Vilsmeier et al. |
| 6,784,660 B2 | 8/2004 | Ashe |
| 6,785,571 B2 | 8/2004 | Glossop |
| 6,786,219 B2 | 9/2004 | Garibaldi et al. |
| 6,786,870 B2 | 9/2004 | Miyaki et al. |
| 6,788,967 B2 | 9/2004 | Ben-Haim et al. |
| 6,794,667 B2 | 9/2004 | Noshi |
| 6,799,066 B2 | 9/2004 | Steines et al. |
| 6,815,651 B2 | 11/2004 | Odell |
| 6,816,266 B2 | 11/2004 | Varshneya et al. |
| 6,817,364 B2 | 11/2004 | Garibaldi et al. |
| 6,834,201 B2 | 12/2004 | Gillies et al. |
| 6,844,713 B2 | 1/2005 | Steber et al. |
| 6,845,142 B2 | 1/2005 | Ohishi |
| 6,856,823 B2 | 2/2005 | Ashe |
| 6,860,422 B2 | 3/2005 | Hull et al. |
| 6,862,467 B2 | 3/2005 | Moore et al. |
| 6,869,390 B2 | 3/2005 | Elliott et al. |
| 6,875,179 B2 | 4/2005 | Ferguson et al. |
| 6,879,160 B2 | 4/2005 | Jakab |
| 6,887,206 B2 | 5/2005 | Hoeksel et al. |
| 6,889,091 B2 | 5/2005 | Hine et al. |
| 6,895,268 B1 | 5/2005 | Rahn et al. |
| 6,902,528 B1 | 6/2005 | Garibaldi et al. |
| 6,905,469 B2 | 6/2005 | Hascoet et al. |
| 6,908,433 B1 | 6/2005 | Pruter |
| 6,911,026 B1 | 6/2005 | Hall et al. |
| 6,923,782 B2 | 8/2005 | O'Mahony et al. |
| 6,926,673 B2 | 8/2005 | Roberts et al. |
| 6,926,674 B2 | 8/2005 | Tenerz et al. |
| 6,934,575 B2 | 8/2005 | Ferre et al. |
| 6,936,010 B2 | 8/2005 | Fang et al. |
| 6,939,313 B2 | 9/2005 | Saadat et al. |
| 6,940,379 B2 | 9/2005 | Creighton |
| 6,941,166 B2 | 9/2005 | MacAdam et al. |
| 6,945,938 B2 | 9/2005 | Grunwald |
| 6,947,788 B2 | 9/2005 | Gilboa et al. |
| 6,950,689 B1 | 9/2005 | Willis et al. |
| 6,953,754 B2 | 10/2005 | Machida et al. |
| 6,958,677 B1 | 10/2005 | Carter |
| 6,959,214 B2 | 10/2005 | Pape et al. |
| 6,962,566 B2 | 11/2005 | Quistgaard et al. |
| 6,968,846 B2 | 11/2005 | Viswanathan |
| 6,975,197 B2 | 12/2005 | Creighton, IV |
| 6,976,962 B2 | 12/2005 | Bullis |
| 6,976,987 B2 | 12/2005 | Flores |
| 6,980,843 B2 | 12/2005 | Eng et al. |
| 6,980,852 B2 | 12/2005 | Jersey-Willuhn et al. |
| 6,980,921 B2 | 12/2005 | Anderson et al. |
| 6,986,739 B2 | 1/2006 | Warren et al. |
| 6,986,744 B1 | 1/2006 | Krivitski |
| 6,999,821 B2 | 2/2006 | Jenney et al. |
| 7,001,355 B2 | 2/2006 | Nunomura et al. |
| 7,008,418 B2 | 3/2006 | Hall et al. |
| 7,010,338 B2 | 3/2006 | Ritter et al. |
| 7,015,393 B2 | 3/2006 | Weiner et al. |
| 7,017,584 B2 | 3/2006 | Garibaldi et al. |
| 7,019,610 B2 | 3/2006 | Creighton, IV et al. |
| 7,020,512 B2 | 3/2006 | Ritter et al. |
| D518,574 S | 4/2006 | Chaggares |
| 7,022,075 B2 | 4/2006 | Grunwald et al. |
| 7,022,082 B2 | 4/2006 | Sonek |
| 7,026,927 B2 | 4/2006 | Wright et al. |
| 7,027,634 B2 | 4/2006 | Odell |
| 7,028,387 B1 | 4/2006 | Huynh et al. |
| 7,029,446 B2 | 4/2006 | Wendelken et al. |
| 7,033,603 B2 | 4/2006 | Nelson et al. |
| D520,139 S | 5/2006 | Chaggares |
| D520,140 S | 5/2006 | Chaggares |
| 7,038,398 B1 | 5/2006 | Lys et al. |
| 7,038,657 B2 | 5/2006 | Rosenberg et al. |
| 7,043,293 B1 | 5/2006 | Baura |
| 7,048,733 B2 | 5/2006 | Hartley et al. |
| 7,054,228 B1 | 5/2006 | Hickling |
| 7,065,403 B1 | 6/2006 | Mouchawar et al. |
| 7,066,914 B2 | 6/2006 | Andersen |
| 7,066,924 B1 | 6/2006 | Garibaldi et al. |
| 7,069,072 B2 | 6/2006 | Jansen et al. |
| D525,363 S | 7/2006 | Chaggares |
| 7,070,565 B2 | 7/2006 | Vaezy et al. |
| 7,072,704 B2 | 7/2006 | Bucholz |
| 7,082,325 B2 | 7/2006 | Hashimshony et al. |
| 7,090,639 B2 | 8/2006 | Govari |
| 7,096,059 B2 | 8/2006 | Geddes et al. |
| 7,096,148 B2 | 8/2006 | Anderson et al. |
| 7,096,870 B2 | 8/2006 | Lamprich et al. |
| 7,098,907 B2 | 8/2006 | Houston et al. |
| 7,103,205 B2 | 9/2006 | Wang et al. |
| 7,104,980 B1 | 9/2006 | Laherty et al. |
| 7,106,043 B1 | 9/2006 | Da Silva et al. |
| 7,106,431 B2 | 9/2006 | Odell |
| 7,106,479 B2 | 9/2006 | Roy et al. |
| 7,107,105 B2 | 9/2006 | Bjorklund et al. |
| 7,112,197 B2 | 9/2006 | Hartley et al. |
| 7,128,734 B1 | 10/2006 | Wilson et al. |
| 7,132,804 B2 | 11/2006 | Lys et al. |
| 7,137,976 B2 | 11/2006 | Ritter et al. |
| 7,141,019 B2 | 11/2006 | Pearlman |
| 7,141,812 B2 | 11/2006 | Appleby et al. |
| 7,142,905 B2 | 11/2006 | Slayton et al. |
| 7,148,970 B2 | 12/2006 | de Boer |
| 7,153,291 B2 | 12/2006 | Bierman |
| 7,161,453 B2 | 1/2007 | Creighton, IV |
| 7,162,291 B1 | 1/2007 | Nachaliel |
| 7,167,738 B2 | 1/2007 | Schweikard et al. |
| 7,169,107 B2 | 1/2007 | Jersey-Willuhn et al. |
| 7,169,109 B2 | 1/2007 | Jansen et al. |
| 7,174,201 B2 | 2/2007 | Govari et al. |
| 7,175,646 B2 | 2/2007 | Brenneman et al. |
| 7,180,252 B2 | 2/2007 | Lys et al. |
| 7,184,820 B2 | 2/2007 | Jersey-Willuhn et al. |

(56) References Cited

U.S. PATENT DOCUMENTS

| | | |
|---|---|---|
| 7,189,198 B2 | 3/2007 | Harburn et al. |
| 7,189,205 B2 | 3/2007 | McMorrow et al. |
| 7,189,208 B1 | 3/2007 | Beatty et al. |
| 7,190,819 B2 | 3/2007 | Viswanathan |
| 7,194,295 B2 | 3/2007 | Vilsmeier |
| 7,204,798 B2 | 4/2007 | Zdeblick et al. |
| 7,206,064 B2 | 4/2007 | Rogers et al. |
| 7,207,941 B2 | 4/2007 | Sharf |
| 7,211,082 B2 | 5/2007 | Hall et al. |
| 7,214,191 B2 | 5/2007 | Stringer et al. |
| 7,215,326 B2 | 5/2007 | Rosenberg |
| 7,221,104 B2 | 5/2007 | Lys et al. |
| 7,223,256 B2 | 5/2007 | Bierman |
| 7,229,400 B2 | 6/2007 | Elliott et al. |
| 7,231,243 B2 | 6/2007 | Tearney et al. |
| 7,236,157 B2 | 6/2007 | Schena et al. |
| 7,236,816 B2 | 6/2007 | Kumar et al. |
| 7,236,820 B2 | 6/2007 | Mabary et al. |
| 7,237,313 B2 | 7/2007 | Skujins et al. |
| 7,241,267 B2 | 7/2007 | Furia |
| 7,244,234 B2 | 7/2007 | Ridley et al. |
| 7,248,032 B1 | 7/2007 | Hular et al. |
| 7,248,914 B2 | 7/2007 | Hastings et al. |
| 7,252,633 B2 | 8/2007 | Obata et al. |
| 7,261,691 B1 | 8/2007 | Asomani |
| 7,264,584 B2 | 9/2007 | Ritter et al. |
| 7,270,662 B2 | 9/2007 | Visram et al. |
| 7,276,044 B2 | 10/2007 | Ferry et al. |
| 7,286,034 B2 | 10/2007 | Creighton |
| 7,291,146 B2 | 11/2007 | Steinke et al. |
| 7,297,140 B2 | 11/2007 | Orlu et al. |
| 7,299,085 B2 | 11/2007 | Bergelson et al. |
| 7,300,430 B2 | 11/2007 | Wilson et al. |
| 7,302,288 B1 | 11/2007 | Schellenberg |
| 7,308,296 B2 | 12/2007 | Lys et al. |
| 7,310,150 B2 | 12/2007 | Guillermo et al. |
| 7,311,702 B2 | 12/2007 | Tallarida et al. |
| 7,321,228 B2 | 1/2008 | Govari |
| 7,326,241 B2 | 2/2008 | Jang |
| 7,327,872 B2 | 2/2008 | Vaillant et al. |
| 7,331,462 B2 | 2/2008 | Steppe |
| 7,342,058 B2 | 3/2008 | Peppmoller et al. |
| 7,349,732 B1 | 3/2008 | Kil et al. |
| 7,355,716 B2 | 4/2008 | de Boer et al. |
| 7,360,427 B2 | 4/2008 | Drinkwater et al. |
| 7,366,376 B2 | 4/2008 | Shishkov et al. |
| 7,366,562 B2 | 4/2008 | Dukesherer et al. |
| 7,366,563 B2 | 4/2008 | Kleen et al. |
| 7,373,271 B1 | 5/2008 | Schneider |
| 7,381,204 B2 | 6/2008 | Wilson et al. |
| 7,382,949 B2 | 6/2008 | Bouma et al. |
| 7,384,407 B2 | 6/2008 | Rodriguez et al. |
| 7,418,169 B2 | 8/2008 | Tearney et al. |
| 7,447,408 B2 | 11/2008 | Bouma et al. |
| 7,452,331 B1 | 11/2008 | Pruter |
| 7,452,358 B2 | 11/2008 | Stern et al. |
| 7,454,244 B2 | 11/2008 | Kassab et al. |
| D585,556 S | 1/2009 | Kosaku |
| 7,479,141 B2 | 1/2009 | Kleen et al. |
| 7,519,424 B2 | 4/2009 | Dennis et al. |
| 7,529,584 B2 | 5/2009 | Laske et al. |
| 7,534,223 B2 | 5/2009 | Boutilette et al. |
| 7,538,859 B2 | 5/2009 | Tearney et al. |
| 7,543,239 B2 | 6/2009 | Viswanathan et al. |
| 7,546,158 B2 | 6/2009 | Allison et al. |
| 7,547,282 B2 | 6/2009 | Lo et al. |
| 7,551,293 B2 | 6/2009 | Yelin et al. |
| D603,050 S | 10/2009 | Chen |
| 7,599,730 B2 | 10/2009 | Hunter et al. |
| 7,606,615 B2 | 10/2009 | Makower et al. |
| 7,613,478 B2 | 11/2009 | Jabri et al. |
| 7,616,992 B2 | 11/2009 | Dennis et al. |
| 7,627,376 B2 | 12/2009 | Dennis et al. |
| 7,635,336 B1 | 12/2009 | Pruter |
| 7,637,163 B2 | 12/2009 | Fetzer et al. |
| 7,640,053 B2 | 12/2009 | Verin |
| 7,651,469 B2 | 1/2010 | Osborne et al. |
| 7,652,080 B2 | 1/2010 | Peppmoller et al. |
| 7,660,623 B2 | 2/2010 | Hunter et al. |
| 7,665,893 B2 | 2/2010 | Buchalter |
| 7,666,191 B2 | 2/2010 | Orban, III et al. |
| 7,668,583 B2 | 2/2010 | Fegert et al. |
| 7,697,972 B2 | 4/2010 | Verard et al. |
| 7,699,782 B2 | 4/2010 | Angelsen et al. |
| 7,699,829 B2 | 4/2010 | Harris et al. |
| 7,715,925 B2 | 5/2010 | Hafer et al. |
| 7,727,192 B2 | 6/2010 | Tokumoto et al. |
| 7,729,743 B2 | 6/2010 | Sabczynski et al. |
| 7,751,865 B2 | 7/2010 | Jascob et al. |
| 7,766,839 B2 | 8/2010 | Rogers et al. |
| 7,771,437 B2 | 8/2010 | Hogg et al. |
| 7,774,051 B2 | 8/2010 | Voth |
| 7,774,055 B1 | 8/2010 | Min |
| 7,794,407 B2 | 9/2010 | Rothenberg |
| 7,798,970 B2 | 9/2010 | Lo et al. |
| 7,819,810 B2 | 10/2010 | Stringer et al. |
| 7,822,464 B2 | 10/2010 | Maschke et al. |
| 7,828,528 B2 | 11/2010 | Estes et al. |
| 7,831,294 B2 | 11/2010 | Viswanathan |
| 7,833,168 B2 | 11/2010 | Taylor et al. |
| 7,833,214 B2 | 11/2010 | Wilson et al. |
| 7,840,252 B2 | 11/2010 | Strommer et al. |
| D629,526 S | 12/2010 | Ladwig et al. |
| D629,527 S | 12/2010 | Crunkilton |
| 7,846,157 B2 | 12/2010 | Kozel |
| 7,850,613 B2 | 12/2010 | Stribling |
| D630,756 S | 1/2011 | Kitayama |
| D630,757 S | 1/2011 | Kitayama |
| 7,869,854 B2 | 1/2011 | Shachar et al. |
| 7,869,865 B2 | 1/2011 | Govari et al. |
| 7,873,402 B2 | 1/2011 | Shachar |
| 7,909,815 B2 | 3/2011 | Whitmore, III et al. |
| 7,931,596 B2 | 4/2011 | Rachlin et al. |
| 7,947,040 B2 | 5/2011 | Davies et al. |
| 7,969,142 B2 | 6/2011 | Krueger et al. |
| 7,976,469 B2 | 7/2011 | Bonde et al. |
| 7,976,518 B2 | 7/2011 | Shaughnessy et al. |
| 7,981,038 B2 | 7/2011 | Kanade et al. |
| 7,988,633 B2 | 8/2011 | Hossack et al. |
| 8,016,814 B2 | 9/2011 | Blakstvedt et al. |
| 8,046,052 B2 | 10/2011 | Verard et al. |
| 8,055,327 B2 | 11/2011 | Strommer et al. |
| 8,057,394 B2 | 11/2011 | Dala-Krishna |
| 8,060,185 B2 | 11/2011 | Hunter et al. |
| 8,078,274 B2 | 12/2011 | Kassab |
| 8,078,279 B2 | 12/2011 | Dennis et al. |
| 8,082,025 B2 | 12/2011 | Amitai et al. |
| 8,082,032 B2 | 12/2011 | Kassab et al. |
| 8,088,072 B2 | 1/2012 | Munrow et al. |
| 8,090,430 B2 | 1/2012 | Makower et al. |
| 8,099,161 B2 | 1/2012 | Kassab |
| 8,105,338 B2 | 1/2012 | Anderson et al. |
| 8,114,143 B2 | 2/2012 | Kassab et al. |
| 8,118,743 B2 | 2/2012 | Park et al. |
| 8,123,691 B2 | 2/2012 | Mine et al. |
| 8,133,698 B2 | 3/2012 | Silver |
| 8,142,417 B2 | 3/2012 | Pajunk et al. |
| 8,150,522 B2 | 4/2012 | Echauz et al. |
| 8,152,724 B2 | 4/2012 | Ridley et al. |
| 8,155,732 B2 | 4/2012 | Scholz et al. |
| 8,204,582 B2 | 6/2012 | Zantos et al. |
| 8,214,018 B2 | 7/2012 | Markowitz et al. |
| 8,221,402 B2 | 7/2012 | Francischelli et al. |
| 8,240,211 B2 | 8/2012 | Zeitner et al. |
| 8,241,274 B2 | 8/2012 | Keogh et al. |
| 8,244,339 B2 | 8/2012 | Shen et al. |
| 8,255,035 B2 | 8/2012 | Cao et al. |
| 8,260,395 B2 | 9/2012 | Markowitz et al. |
| 8,262,577 B2 | 9/2012 | Munrow et al. |
| 8,298,149 B2 | 10/2012 | Hastings et al. |
| 8,303,502 B2 | 11/2012 | Washburn et al. |
| 8,303,505 B2 | 11/2012 | Webler et al. |
| 8,326,419 B2 | 12/2012 | Rosenberg et al. |
| 8,326,651 B2 | 12/2012 | McLaren et al. |

(56) References Cited

U.S. PATENT DOCUMENTS

| | | |
|---|---|---|
| 8,340,751 B2 | 12/2012 | Markowitz et al. |
| 8,346,343 B2 | 1/2013 | Kimura et al. |
| 8,369,922 B2 | 2/2013 | Paul et al. |
| 8,388,541 B2 | 3/2013 | Messerly et al. |
| 8,388,546 B2 | 3/2013 | Rothenberg |
| 8,391,956 B2 | 3/2013 | Zellers et al. |
| 8,400,164 B2 | 3/2013 | Osadchy et al. |
| 8,401,616 B2 | 3/2013 | Verard et al. |
| 8,409,103 B2 | 4/2013 | Grunwald et al. |
| 8,412,313 B2 | 4/2013 | Amitai et al. |
| 8,425,425 B2 | 4/2013 | Hagy et al. |
| 8,437,833 B2 | 5/2013 | Silverstein |
| 8,439,873 B1 | 5/2013 | Donovan |
| 8,442,621 B2 | 5/2013 | Gorek et al. |
| 8,447,384 B2 | 5/2013 | Xu et al. |
| D684,265 S | 6/2013 | Cadera |
| 8,456,182 B2 | 6/2013 | Bar-Tal et al. |
| 8,478,382 B2 | 7/2013 | Burnside et al. |
| 8,478,388 B2 | 7/2013 | Nguyen et al. |
| 8,485,980 B2 | 7/2013 | Sinderby et al. |
| 8,494,608 B2 | 7/2013 | Markowitz et al. |
| 8,496,592 B2 | 7/2013 | Ridley et al. |
| 8,504,139 B2 | 8/2013 | Jacobsen et al. |
| 8,512,256 B2 | 8/2013 | Rothenberg |
| 8,521,122 B2 | 8/2013 | Scott et al. |
| 8,527,036 B2 | 9/2013 | Jalde et al. |
| 8,538,509 B2 | 9/2013 | Harlev et al. |
| 8,597,193 B2 | 12/2013 | Grunwald et al. |
| 8,620,412 B2 | 12/2013 | Griffiths et al. |
| 8,644,907 B2 | 2/2014 | Hartmann et al. |
| 8,663,116 B2 | 3/2014 | Hamilton, Jr. |
| 8,690,776 B2 | 4/2014 | Razzaque et al. |
| 8,700,137 B2 | 4/2014 | Albert |
| 8,715,195 B2 | 5/2014 | Ziv |
| 8,721,655 B2 | 5/2014 | Viswanathan et al. |
| 8,734,440 B2 | 5/2014 | Wu |
| 8,761,862 B2 | 6/2014 | Ridley et al. |
| 8,774,907 B2 | 7/2014 | Rothenberg |
| 8,781,555 B2 | 7/2014 | Burnside et al. |
| 8,784,336 B2 | 7/2014 | Bown et al. |
| 8,801,693 B2 | 8/2014 | He et al. |
| 8,849,382 B2 | 9/2014 | Cox et al. |
| 8,858,455 B2 | 10/2014 | Rothenberg |
| 8,934,961 B2 | 1/2015 | Lakin et al. |
| 8,942,784 B2 | 1/2015 | Neidert et al. |
| 8,965,490 B2 | 2/2015 | Lee et al. |
| 8,971,994 B2 | 3/2015 | Burnside et al. |
| 9,014,794 B2 | 4/2015 | Brodnick et al. |
| 9,033,889 B2 | 5/2015 | Hamilton, Jr. |
| 9,125,578 B2 | 9/2015 | Grunwald |
| 9,179,860 B2 | 11/2015 | Markowitz et al. |
| 9,198,600 B2 | 12/2015 | Grunwald et al. |
| 9,339,206 B2 | 5/2016 | Grunwald |
| 9,415,188 B2 | 8/2016 | He et al. |
| 9,456,766 B2 | 10/2016 | Cox et al. |
| 9,492,097 B2 | 11/2016 | Wilkes et al. |
| 9,521,961 B2 | 12/2016 | Silverstein et al. |
| 9,526,440 B2 | 12/2016 | Burnside et al. |
| 9,532,724 B2 | 1/2017 | Grunwald |
| 9,554,716 B2 | 1/2017 | Burnside et al. |
| 9,636,031 B2 | 5/2017 | Cox |
| 9,642,986 B2 | 5/2017 | Beasley |
| 9,649,048 B2 | 5/2017 | Cox et al. |
| 9,681,823 B2 | 6/2017 | Messerly et al. |
| 9,833,169 B2 | 12/2017 | Rothenberg |
| 9,839,372 B2 | 12/2017 | Bukhman et al. |
| 9,901,714 B2 | 2/2018 | Lemon et al. |
| 9,907,513 B2 | 3/2018 | Silverstein |
| 9,999,371 B2 | 6/2018 | Messerly et al. |
| 10,004,875 B2 | 6/2018 | Bown et al. |
| 10,046,139 B2 | 8/2018 | Powers et al. |
| 10,105,121 B2 | 10/2018 | Burnside et al. |
| 10,165,962 B2 | 1/2019 | Messerly et al. |
| 10,231,643 B2 | 3/2019 | Grunwald |
| 10,231,753 B2 | 3/2019 | Burnside et al. |
| 10,238,418 B2 | 3/2019 | Cox et al. |
| 10,271,762 B2 | 4/2019 | Grunwald |
| 10,349,857 B2 | 7/2019 | Grunwald |
| 10,349,890 B2 | 7/2019 | Misener et al. |
| 10,449,330 B2 | 10/2019 | Newman et al. |
| 10,524,691 B2 | 1/2020 | Newman et al. |
| 10,602,958 B2 | 3/2020 | Silverstein et al. |
| 2001/0014774 A1 | 8/2001 | Grunwald |
| 2001/0027332 A1 | 10/2001 | Grunwald et al. |
| 2002/0010392 A1 | 1/2002 | Desai |
| 2002/0016549 A1 | 2/2002 | Mejia |
| 2002/0019447 A1 | 2/2002 | Renn et al. |
| 2002/0022777 A1 | 2/2002 | Crieghton et al. |
| 2002/0032391 A1 | 3/2002 | McFann et al. |
| 2002/0045810 A1 | 4/2002 | Ben-Haim |
| 2002/0049488 A1 | 4/2002 | Boneau |
| 2002/0055680 A1 | 5/2002 | Miele et al. |
| 2002/0082559 A1 | 6/2002 | Chang et al. |
| 2002/0113555 A1 | 8/2002 | Lys et al. |
| 2002/0123679 A1 | 9/2002 | Dominguez |
| 2002/0128554 A1 | 9/2002 | Seward |
| 2002/0129952 A1 | 9/2002 | Matsudate et al. |
| 2002/0133079 A1 | 9/2002 | Sandhu |
| 2002/0156363 A1 | 10/2002 | Hunter et al. |
| 2002/0156376 A1 | 10/2002 | Wang et al. |
| 2002/0165448 A1 | 11/2002 | Ben-Haim et al. |
| 2002/0165534 A1 | 11/2002 | Hayzelden et al. |
| 2002/0165537 A1 | 11/2002 | Kelley et al. |
| 2002/0173721 A1 | 11/2002 | Grunwald et al. |
| 2002/0193756 A1 | 12/2002 | Prindle |
| 2002/0198568 A1 | 12/2002 | Hafer et al. |
| 2003/0009132 A1 | 1/2003 | Schwartz et al. |
| 2003/0011359 A1 | 1/2003 | Ashe |
| 2003/0013959 A1 | 1/2003 | Grunwald et al. |
| 2003/0013966 A1 | 1/2003 | Barnes et al. |
| 2003/0013986 A1 | 1/2003 | Saadat |
| 2003/0018251 A1 | 1/2003 | Solomon |
| 2003/0036696 A1 | 2/2003 | Willis et al. |
| 2003/0040671 A1 | 2/2003 | Somogyi et al. |
| 2003/0040743 A1 | 2/2003 | Cosman et al. |
| 2003/0072805 A1 | 4/2003 | Miyazawa et al. |
| 2003/0073901 A1 | 4/2003 | Simon et al. |
| 2003/0076281 A1 | 4/2003 | Morgan et al. |
| 2003/0083698 A1 | 5/2003 | Whitehurst et al. |
| 2003/0088195 A1 | 5/2003 | Vardi et al. |
| 2003/0092993 A1 | 5/2003 | Grunwald |
| 2003/0100849 A1 | 5/2003 | Jang |
| 2003/0114742 A1 | 6/2003 | Lewkowicz et al. |
| 2003/0114777 A1 | 6/2003 | Griffin et al. |
| 2003/0120150 A1 | 6/2003 | Govari |
| 2003/0120154 A1 | 6/2003 | Sauer et al. |
| 2003/0139661 A1 | 7/2003 | Kimchy et al. |
| 2003/0149328 A1 | 8/2003 | Elliott et al. |
| 2003/0149368 A1 | 8/2003 | Hennemann et al. |
| 2003/0152290 A1 | 8/2003 | Odell |
| 2003/0160721 A1 | 8/2003 | Gilboa et al. |
| 2003/0162414 A1 | 8/2003 | Schulz et al. |
| 2003/0163037 A1 | 8/2003 | Bladen et al. |
| 2003/0163142 A1 | 8/2003 | Paltieli et al. |
| 2003/0171691 A1 | 9/2003 | Casscells et al. |
| 2003/0173953 A1 | 9/2003 | Ashe |
| 2003/0181892 A1 | 9/2003 | Pajunk et al. |
| 2003/0184544 A1 | 10/2003 | Prudent |
| 2003/0191392 A1 | 10/2003 | Haldeman |
| 2003/0191460 A1 | 10/2003 | Hobbs et al. |
| 2003/0195420 A1 | 10/2003 | Mendlein et al. |
| 2003/0199746 A1 | 10/2003 | Fuimaono et al. |
| 2003/0208142 A1 | 11/2003 | Boudewijn et al. |
| 2003/0216639 A1 | 11/2003 | Gilboa et al. |
| 2003/0216723 A1 | 11/2003 | Shinmura et al. |
| 2003/0220557 A1 | 11/2003 | Cleary et al. |
| 2003/0220578 A1 | 11/2003 | Ho et al. |
| 2003/0229298 A1 | 12/2003 | Iwami et al. |
| 2003/0233042 A1 | 12/2003 | Ashe |
| 2003/0236445 A1 | 12/2003 | Couvillon |
| 2004/0010189 A1 | 1/2004 | van Sloun et al. |
| 2004/0015070 A1 | 1/2004 | Liang et al. |
| 2004/0024301 A1 | 2/2004 | Hockett et al. |
| 2004/0030319 A1 | 2/2004 | Korkor et al. |

(56) References Cited

U.S. PATENT DOCUMENTS

| | | |
|---|---|---|
| 2004/0054278 A1 | 3/2004 | Kimchy et al. |
| 2004/0059217 A1 | 3/2004 | Kessman et al. |
| 2004/0059237 A1 | 3/2004 | Narayan et al. |
| 2004/0082916 A1 | 4/2004 | Jenkins |
| 2004/0087877 A1 | 5/2004 | Besz et al. |
| 2004/0088136 A1 | 5/2004 | Ashe |
| 2004/0092962 A1 | 5/2004 | Thornton et al. |
| 2004/0097803 A1 | 5/2004 | Panescu |
| 2004/0097804 A1 | 5/2004 | Sobe |
| 2004/0097805 A1 | 5/2004 | Verard et al. |
| 2004/0097806 A1 | 5/2004 | Hunter et al. |
| 2004/0116809 A1 | 6/2004 | Chow et al. |
| 2004/0127805 A1 | 7/2004 | MacAdam et al. |
| 2004/0131998 A1 | 7/2004 | Marom et al. |
| 2004/0133111 A1 | 7/2004 | Szczech et al. |
| 2004/0133130 A1 | 7/2004 | Ferry et al. |
| 2004/0135069 A1 | 7/2004 | Odell |
| 2004/0138557 A1 | 7/2004 | Le et al. |
| 2004/0138564 A1 | 7/2004 | Hwang et al. |
| 2004/0138569 A1 | 7/2004 | Grunwald et al. |
| 2004/0138570 A1 | 7/2004 | Nita et al. |
| 2004/0143183 A1 | 7/2004 | Toyoda et al. |
| 2004/0147837 A1 | 7/2004 | Macaulay et al. |
| 2004/0150963 A1 | 8/2004 | Holmberg et al. |
| 2004/0152972 A1 | 8/2004 | Hunter |
| 2004/0155609 A1 | 8/2004 | Lys et al. |
| 2004/0158140 A1 | 8/2004 | Fuimaono et al. |
| 2004/0171924 A1 | 9/2004 | Mire et al. |
| 2004/0176688 A1 | 9/2004 | Haldeman |
| 2004/0186461 A1 | 9/2004 | DiMatteo |
| 2004/0199069 A1 | 10/2004 | Connelly et al. |
| 2004/0210289 A1 | 10/2004 | Wang et al. |
| 2004/0225233 A1 | 11/2004 | Frankowski et al. |
| 2004/0230131 A1 | 11/2004 | Kassab et al. |
| 2004/0230271 A1 | 11/2004 | Wang et al. |
| 2004/0234453 A1 | 11/2004 | Smith |
| 2004/0243018 A1 | 12/2004 | Organ et al. |
| 2004/0243116 A1 | 12/2004 | Joye et al. |
| 2004/0243118 A1 | 12/2004 | Ayers et al. |
| 2004/0253365 A1 | 12/2004 | Warren et al. |
| 2004/0254470 A1 | 12/2004 | Drinkwater et al. |
| 2004/0254495 A1 | 12/2004 | Mabary et al. |
| 2004/0260174 A1 | 12/2004 | Keene |
| 2004/0267086 A1 | 12/2004 | Anstadt et al. |
| 2005/0004450 A1 | 1/2005 | Ben-Haim et al. |
| 2005/0021019 A1 | 1/2005 | Hashimshony et al. |
| 2005/0033150 A1 | 2/2005 | Takahashi et al. |
| 2005/0038355 A1 | 2/2005 | Gellman et al. |
| 2005/0043640 A1 | 2/2005 | Chang |
| 2005/0049486 A1 | 3/2005 | Urquhart et al. |
| 2005/0049510 A1 | 3/2005 | Haldeman et al. |
| 2005/0063194 A1 | 3/2005 | Lys et al. |
| 2005/0070788 A1 | 3/2005 | Wilson et al. |
| 2005/0075561 A1 | 4/2005 | Golden |
| 2005/0085715 A1 | 4/2005 | Dukesherer et al. |
| 2005/0085716 A1 | 4/2005 | Hamm et al. |
| 2005/0085718 A1 | 4/2005 | Shahidi |
| 2005/0085720 A1 | 4/2005 | Jascob et al. |
| 2005/0090746 A1 | 4/2005 | Ohtake |
| 2005/0101868 A1 | 5/2005 | Ridley et al. |
| 2005/0101869 A1 | 5/2005 | Burba et al. |
| 2005/0105081 A1 | 5/2005 | Odell |
| 2005/0105101 A1 | 5/2005 | Duling et al. |
| 2005/0112135 A1 | 5/2005 | Cormier et al. |
| 2005/0113669 A1 | 5/2005 | Helfer et al. |
| 2005/0113676 A1 | 5/2005 | Weiner et al. |
| 2005/0113700 A1 | 5/2005 | Yanagihara et al. |
| 2005/0113873 A1 | 5/2005 | Weiner et al. |
| 2005/0113874 A1 | 5/2005 | Connelly et al. |
| 2005/0113876 A1 | 5/2005 | Weiner et al. |
| 2005/0143689 A1 | 6/2005 | Ramsey |
| 2005/0148836 A1 | 7/2005 | Kleen et al. |
| 2005/0148902 A1 | 7/2005 | Minar et al. |
| 2005/0149002 A1 | 7/2005 | Wang et al. |
| 2005/0151489 A1 | 7/2005 | Lys et al. |
| 2005/0154308 A1 | 7/2005 | Quistgaard et al. |
| 2005/0159644 A1 | 7/2005 | Takano |
| 2005/0159790 A1 | 7/2005 | Shalev |
| 2005/0165301 A1 | 7/2005 | Smith et al. |
| 2005/0165313 A1 | 7/2005 | Byron et al. |
| 2005/0175665 A1 | 8/2005 | Hunter et al. |
| 2005/0175703 A1 | 8/2005 | Hunter et al. |
| 2005/0178395 A1 | 8/2005 | Hunter et al. |
| 2005/0178396 A1 | 8/2005 | Hunter et al. |
| 2005/0182295 A1 | 8/2005 | Soper et al. |
| 2005/0182454 A1 | 8/2005 | Gharib et al. |
| 2005/0197674 A1 | 9/2005 | McCabe et al. |
| 2005/0203368 A1 | 9/2005 | Verin |
| 2005/0203396 A1 | 9/2005 | Angelsen et al. |
| 2005/0205081 A1 | 9/2005 | Barker et al. |
| 2005/0215901 A1 | 9/2005 | Anderson et al. |
| 2005/0215945 A1 | 9/2005 | Harris et al. |
| 2005/0222532 A1 | 10/2005 | Bertolero et al. |
| 2005/0240102 A1 | 10/2005 | Rachlin et al. |
| 2005/0245811 A1 | 11/2005 | Scheffler |
| 2005/0256398 A1 | 11/2005 | Hastings et al. |
| 2005/0256451 A1 | 11/2005 | Adams et al. |
| 2005/0256521 A1 | 11/2005 | Kozel |
| 2005/0256541 A1 | 11/2005 | Stypulkowski |
| 2005/0283210 A1 | 12/2005 | Blischak et al. |
| 2005/0283216 A1 | 12/2005 | Pyles |
| 2005/0288586 A1 | 12/2005 | Ferek-Petric |
| 2005/0288695 A1 | 12/2005 | Jenson et al. |
| 2006/0009759 A1 | 1/2006 | Chrisitian et al. |
| 2006/0015003 A1 | 1/2006 | Moaddes et al. |
| 2006/0025677 A1 | 2/2006 | Verard et al. |
| 2006/0025697 A1 | 2/2006 | Kurzweil et al. |
| 2006/0058633 A1 | 3/2006 | Hoshino et al. |
| 2006/0065275 A1* | 3/2006 | Lamprich ............ A61B 46/23 128/849 |
| 2006/0068074 A1 | 3/2006 | Stefandl |
| 2006/0084867 A1 | 4/2006 | Tremblay et al. |
| 2006/0106306 A1 | 5/2006 | Essner et al. |
| 2006/0116571 A1 | 6/2006 | Maschke et al. |
| 2006/0116576 A1 | 6/2006 | McGee et al. |
| 2006/0116578 A1 | 6/2006 | Grunwald et al. |
| 2006/0122514 A1 | 6/2006 | Byrd et al. |
| 2006/0142656 A1 | 6/2006 | Malackowski et al. |
| 2006/0149134 A1 | 7/2006 | Soper et al. |
| 2006/0173251 A1 | 8/2006 | Govari et al. |
| 2006/0173329 A1 | 8/2006 | Irioka et al. |
| 2006/0173407 A1 | 8/2006 | Shaughnessy et al. |
| 2006/0176242 A1 | 8/2006 | Jaramaz et al. |
| 2006/0184074 A1 | 8/2006 | Vaezy et al. |
| 2006/0206037 A1 | 9/2006 | Braxton |
| 2006/0211944 A1 | 9/2006 | Mauge et al. |
| 2006/0217655 A1 | 9/2006 | Vitullo et al. |
| 2006/0217755 A1 | 9/2006 | Eversull et al. |
| 2006/0224188 A1 | 10/2006 | Libbus et al. |
| 2006/0241432 A1 | 10/2006 | Herline et al. |
| 2006/0247746 A1 | 11/2006 | Danek et al. |
| 2006/0253029 A1 | 11/2006 | Altmann et al. |
| 2006/0253115 A1 | 11/2006 | Avitall et al. |
| 2006/0258895 A1 | 11/2006 | Maschke |
| 2006/0276867 A1 | 12/2006 | Viswanathan |
| 2006/0287595 A1 | 12/2006 | Maschke |
| 2007/0010753 A1 | 1/2007 | MacAdam |
| 2007/0016007 A1 | 1/2007 | Govari et al. |
| 2007/0016013 A1 | 1/2007 | Camus |
| 2007/0016068 A1 | 1/2007 | Grunwald et al. |
| 2007/0016069 A1 | 1/2007 | Grunwald et al. |
| 2007/0016070 A1 | 1/2007 | Grunwald et al. |
| 2007/0016072 A1 | 1/2007 | Grunwald et al. |
| 2007/0032746 A1 | 2/2007 | Sell |
| 2007/0038113 A1 | 2/2007 | Oonuki et al. |
| 2007/0049817 A1 | 3/2007 | Preiss et al. |
| 2007/0049822 A1 | 3/2007 | Bunce et al. |
| 2007/0049846 A1 | 3/2007 | Bown et al. |
| 2007/0055141 A1 | 3/2007 | Kruger et al. |
| 2007/0055142 A1 | 3/2007 | Webler |
| 2007/0055294 A1 | 3/2007 | Giap |
| 2007/0060992 A1 | 3/2007 | Pappone |
| 2007/0062544 A1 | 3/2007 | Rauk Bergstrom et al. |
| 2007/0066888 A1 | 3/2007 | Maschke |

(56) References Cited

U.S. PATENT DOCUMENTS

| | | |
|---|---|---|
| 2007/0073155 A1 | 3/2007 | Park et al. |
| 2007/0078343 A1 | 4/2007 | Kawashima et al. |
| 2007/0087038 A1 | 4/2007 | Richardson et al. |
| 2007/0093710 A1 | 4/2007 | Maschke |
| 2007/0100236 A1 | 5/2007 | McMorrow et al. |
| 2007/0100285 A1 | 5/2007 | Griffin et al. |
| 2007/0112282 A1 | 5/2007 | Skujins et al. |
| 2007/0123805 A1 | 5/2007 | Shireman et al. |
| 2007/0129770 A1 | 6/2007 | Younis |
| 2007/0135803 A1 | 6/2007 | Belson |
| 2007/0135886 A1 | 6/2007 | Maschke |
| 2007/0156205 A1 | 7/2007 | Larson et al. |
| 2007/0161853 A1 | 7/2007 | Yagi et al. |
| 2007/0161914 A1 | 7/2007 | Zdeblick et al. |
| 2007/0161915 A1 | 7/2007 | Desai |
| 2007/0167738 A1 | 7/2007 | Timinger et al. |
| 2007/0167762 A1 | 7/2007 | Kim et al. |
| 2007/0167769 A1 | 7/2007 | Ikuma et al. |
| 2007/0167801 A1 | 7/2007 | Webler et al. |
| 2007/0167997 A1 | 7/2007 | Forsberg et al. |
| 2007/0197891 A1 | 8/2007 | Shachar et al. |
| 2007/0197905 A1 | 8/2007 | Timinger et al. |
| 2007/0197926 A1 | 8/2007 | Danehorn et al. |
| 2007/0208255 A1 | 9/2007 | Ridley et al. |
| 2007/0219453 A1 | 9/2007 | Kremliovsky et al. |
| 2007/0225589 A1 | 9/2007 | Viswanathan |
| 2007/0225610 A1 | 9/2007 | Mickley et al. |
| 2007/0232882 A1 | 10/2007 | Glossop et al. |
| 2007/0232896 A1 | 10/2007 | Gilboa et al. |
| 2007/0238984 A1 | 10/2007 | Maschke et al. |
| 2007/0239004 A1 | 10/2007 | Kakee et al. |
| 2007/0239018 A1 | 10/2007 | Fetzer et al. |
| 2007/0244413 A1 | 10/2007 | Biggins |
| 2007/0247454 A1 | 10/2007 | Rahn et al. |
| 2007/0249911 A1 | 10/2007 | Simon |
| 2007/0250150 A1 | 10/2007 | Pal et al. |
| 2007/0255270 A1 | 11/2007 | Carney |
| 2007/0265526 A1 | 11/2007 | Govari et al. |
| 2007/0280974 A1 | 12/2007 | Son et al. |
| 2007/0282196 A1 | 12/2007 | Birk et al. |
| 2007/0282197 A1 | 12/2007 | Bill et al. |
| 2007/0299352 A1 | 12/2007 | Harlev et al. |
| 2007/0299353 A1 | 12/2007 | Harlev et al. |
| 2008/0004652 A1 | 1/2008 | Abboud et al. |
| 2008/0008745 A1 | 1/2008 | Stinchcomb et al. |
| 2008/0009720 A1 | 1/2008 | Schefelker et al. |
| 2008/0015442 A1 | 1/2008 | Watson et al. |
| 2008/0021283 A1 | 1/2008 | Kuranda |
| 2008/0027320 A1 | 1/2008 | Bolorforosh et al. |
| 2008/0033282 A1 | 2/2008 | Bar-Tal et al. |
| 2008/0033283 A1 | 2/2008 | Dellaca et al. |
| 2008/0033316 A1 | 2/2008 | Kassab et al. |
| 2008/0033350 A1 | 2/2008 | Wilson et al. |
| 2008/0045908 A1 | 2/2008 | Gould et al. |
| 2008/0051626 A1 | 2/2008 | Sato et al. |
| 2008/0077158 A1 | 3/2008 | Haider et al. |
| 2008/0081958 A1 | 4/2008 | Denison et al. |
| 2008/0082136 A1 | 4/2008 | Gaudiani |
| 2008/0097232 A1 | 4/2008 | Rothenberg |
| 2008/0108949 A1 | 5/2008 | Beasley et al. |
| 2008/0114095 A1 | 5/2008 | Peppmoller et al. |
| 2008/0119697 A1 | 5/2008 | Vadodaria et al. |
| 2008/0125772 A1 | 5/2008 | Stone et al. |
| 2008/0137927 A1 | 6/2008 | Altmann et al. |
| 2008/0139944 A1 | 6/2008 | Weymer et al. |
| 2008/0146939 A1 | 6/2008 | McMorrow et al. |
| 2008/0146940 A1 | 6/2008 | Jenkins et al. |
| 2008/0146941 A1 | 6/2008 | Dala-Krishna |
| 2008/0146942 A1 | 6/2008 | Dala-Krishna |
| 2008/0154100 A1 | 6/2008 | Thalmeier et al. |
| 2008/0166453 A1 | 7/2008 | Steele et al. |
| 2008/0171934 A1 | 7/2008 | Greenan et al. |
| 2008/0183075 A1 | 7/2008 | Govari et al. |
| 2008/0188830 A1 | 8/2008 | Rosenblatt et al. |
| 2008/0190438 A1 | 8/2008 | Harlev et al. |
| 2008/0195169 A1 | 8/2008 | Pinter et al. |
| 2008/0200754 A1 | 8/2008 | Buchalter |
| 2008/0200801 A1 | 8/2008 | Wildes et al. |
| 2008/0200913 A1 | 8/2008 | Viswanathan |
| 2008/0228082 A1 | 9/2008 | Scheirer et al. |
| 2008/0236598 A1 | 10/2008 | Gobel |
| 2008/0255404 A1 | 10/2008 | Nogawa et al. |
| 2008/0255475 A1 | 10/2008 | Kondrosky et al. |
| 2008/0269581 A1 | 10/2008 | Wood et al. |
| 2008/0269611 A1 | 10/2008 | Pedrizzetti et al. |
| 2008/0275465 A1 | 11/2008 | Paul et al. |
| 2008/0275765 A1 | 11/2008 | Kuchar |
| 2008/0288038 A1 | 11/2008 | Paul et al. |
| 2008/0294041 A1 | 11/2008 | Kassab |
| 2008/0319350 A1 | 12/2008 | Wallace et al. |
| 2009/0005674 A1 | 1/2009 | Saadat et al. |
| 2009/0005675 A1 | 1/2009 | Grunwald et al. |
| 2009/0005679 A1 | 1/2009 | Dala-Krishna |
| 2009/0018497 A1 | 1/2009 | Birchard et al. |
| 2009/0024018 A1 | 1/2009 | Boyden et al. |
| 2009/0030380 A1 | 1/2009 | Binmoeller |
| 2009/0043205 A1 | 2/2009 | Pelissier et al. |
| 2009/0062646 A1 | 3/2009 | Creighton, IV et al. |
| 2009/0062684 A1 | 3/2009 | Gregersen et al. |
| 2009/0062772 A1 | 3/2009 | Wakeford et al. |
| 2009/0080738 A1 | 3/2009 | Zur et al. |
| 2009/0082661 A1 | 3/2009 | Saladin et al. |
| 2009/0084382 A1 | 4/2009 | Jalde et al. |
| 2009/0099468 A1 | 4/2009 | Thiagalingam et al. |
| 2009/0101577 A1 | 4/2009 | Fulkerson et al. |
| 2009/0115406 A1 | 5/2009 | Anderson et al. |
| 2009/0118612 A1 | 5/2009 | Grunwald et al. |
| 2009/0118637 A1 | 5/2009 | Kassab et al. |
| 2009/0118706 A1 | 5/2009 | Schweikert et al. |
| 2009/0124901 A1 | 5/2009 | Fink et al. |
| 2009/0143736 A1 | 6/2009 | Mittermeyer et al. |
| 2009/0156926 A1 | 6/2009 | Messerly et al. |
| 2009/0163810 A1 | 6/2009 | Kanade et al. |
| 2009/0171217 A1 | 7/2009 | Kim et al. |
| 2009/0177083 A1 | 7/2009 | Matsumura |
| 2009/0177090 A1 | 7/2009 | Grunwald et al. |
| 2009/0182224 A1 | 7/2009 | Shmarak et al. |
| 2009/0203989 A1 | 8/2009 | Burnside et al. |
| 2009/0204113 A1 | 8/2009 | MacAdam et al. |
| 2009/0209872 A1 | 8/2009 | Pop |
| 2009/0209950 A1 | 8/2009 | Starksen |
| 2009/0221908 A1 | 9/2009 | Glossop |
| 2009/0227952 A1 | 9/2009 | Blakstvedt et al. |
| 2009/0234328 A1 | 9/2009 | Cox et al. |
| 2009/0253976 A1 | 10/2009 | Harlev et al. |
| 2009/0258171 A1 | 10/2009 | Uang |
| 2009/0259124 A1 | 10/2009 | Rothenberg |
| 2009/0262982 A1 | 10/2009 | Markowitz et al. |
| 2009/0270729 A1 | 10/2009 | Corbucci et al. |
| 2009/0270746 A1 | 10/2009 | Min |
| 2009/0275828 A1 | 11/2009 | Shachar et al. |
| 2009/0281419 A1 | 11/2009 | Troesken et al. |
| 2009/0297441 A1 | 12/2009 | Canham et al. |
| 2009/0312629 A1 | 12/2009 | Razzaque et al. |
| 2010/0004543 A1 | 1/2010 | Ahlund et al. |
| 2010/0004547 A1 | 1/2010 | Scholz et al. |
| 2010/0010355 A1 | 1/2010 | Kassab |
| 2010/0010444 A1 | 1/2010 | Bettuchi |
| 2010/0010612 A1 | 1/2010 | Gelbart et al. |
| 2010/0016726 A1 | 1/2010 | Meier |
| 2010/0036227 A1 | 2/2010 | Cox et al. |
| 2010/0036284 A1 | 2/2010 | Laynes et al. |
| 2010/0041973 A1 | 2/2010 | Vu et al. |
| 2010/0041984 A1 | 2/2010 | Shapland et al. |
| 2010/0049062 A1 | 2/2010 | Liv |
| 2010/0055153 A1 | 3/2010 | Majmudar |
| 2010/0055184 A1 | 3/2010 | Zeitels et al. |
| 2010/0057157 A1 | 3/2010 | Govari et al. |
| 2010/0060472 A1 | 3/2010 | Kimura et al. |
| 2010/0063401 A1 | 3/2010 | Nishina et al. |
| 2010/0076305 A1 | 3/2010 | Maier-Hein et al. |
| 2010/0076328 A1 | 3/2010 | Matsumura et al. |
| 2010/0081934 A1 | 4/2010 | Soltani et al. |
| 2010/0083719 A1 | 4/2010 | Peppmoller et al. |

(56) References Cited

U.S. PATENT DOCUMENTS

| | | |
|---|---|---|
| 2010/0094116 A1 | 4/2010 | Silverstein |
| 2010/0106011 A1 | 4/2010 | Byrd et al. |
| 2010/0113917 A1 | 5/2010 | Anderson |
| 2010/0114573 A1 | 5/2010 | Huang et al. |
| 2010/0117659 A1 | 5/2010 | Osadchy et al. |
| 2010/0130858 A1 | 5/2010 | Arai et al. |
| 2010/0143119 A1 | 6/2010 | Kooijman et al. |
| 2010/0152596 A1 | 6/2010 | Griffiths et al. |
| 2010/0152604 A1 | 6/2010 | Kaula et al. |
| 2010/0160772 A1 | 6/2010 | Gardeski et al. |
| 2010/0168557 A1 | 7/2010 | Deno et al. |
| 2010/0185097 A1 | 7/2010 | Hall |
| 2010/0198048 A1 | 8/2010 | Togawa |
| 2010/0198346 A1 | 8/2010 | Keogh et al. |
| 2010/0204569 A1 | 8/2010 | Burnside et al. |
| 2010/0204614 A1 | 8/2010 | Lindquist et al. |
| 2010/0210938 A1 | 8/2010 | Verard et al. |
| 2010/0210950 A1 | 8/2010 | Dunbar et al. |
| 2010/0217116 A1 | 8/2010 | Eck et al. |
| 2010/0222664 A1 | 9/2010 | Lemon et al. |
| 2010/0222786 A1 | 9/2010 | Kassab |
| 2010/0234724 A1 | 9/2010 | Jacobsen et al. |
| 2010/0234733 A1 | 9/2010 | Wahlheim |
| 2010/0249598 A1 | 9/2010 | Smith et al. |
| 2010/0258033 A1 | 10/2010 | Yang et al. |
| 2010/0268059 A1 | 10/2010 | Ryu et al. |
| 2010/0273895 A1 | 10/2010 | Stinchcomb et al. |
| 2010/0274150 A1 | 10/2010 | Harlev et al. |
| 2010/0291521 A1 | 11/2010 | Simon |
| 2010/0298702 A1 | 11/2010 | Rogers et al. |
| 2010/0298704 A1 | 11/2010 | Pelissier et al. |
| 2010/0298705 A1 | 11/2010 | Pelissier et al. |
| 2010/0298712 A1 | 11/2010 | Pelissier et al. |
| 2010/0312086 A9 | 12/2010 | Beatty et al. |
| 2010/0317981 A1 | 12/2010 | Grunwald |
| 2010/0318026 A1 | 12/2010 | Grunwald |
| 2010/0331712 A1 | 12/2010 | Rothenberg |
| 2011/0015496 A1 | 1/2011 | Sherman et al. |
| 2011/0015527 A1 | 1/2011 | Heasty et al. |
| 2011/0015533 A1 | 1/2011 | Cox et al. |
| 2011/0034823 A1 | 2/2011 | Gelbart et al. |
| 2011/0034940 A1 | 2/2011 | Payner |
| 2011/0040212 A1 | 2/2011 | Dietz et al. |
| 2011/0052694 A1 | 3/2011 | Stinchcomb et al. |
| 2011/0087105 A1 | 4/2011 | Ridley et al. |
| 2011/0087106 A1 | 4/2011 | Ridley et al. |
| 2011/0087107 A1 | 4/2011 | Lindekugel et al. |
| 2011/0106101 A1 | 5/2011 | Tortonese et al. |
| 2011/0112396 A1 | 5/2011 | Shachar et al. |
| 2011/0136242 A1 | 6/2011 | Marx et al. |
| 2011/0137156 A1 | 6/2011 | Razzaque et al. |
| 2011/0196235 A1 | 8/2011 | Dunbar et al. |
| 2011/0196248 A1* | 8/2011 | Grunwald ............. A61B 5/06 600/509 |
| 2011/0196255 A1 | 8/2011 | Kassab |
| 2011/0237935 A1 | 9/2011 | Kalpin et al. |
| 2011/0245659 A1 | 10/2011 | Ma et al. |
| 2011/0282187 A1 | 11/2011 | Harlev et al. |
| 2011/0282188 A1 | 11/2011 | Burnside et al. |
| 2011/0282285 A1 | 11/2011 | Blanchard et al. |
| 2011/0282686 A1 | 11/2011 | Venon et al. |
| 2011/0295108 A1 | 12/2011 | Cox et al. |
| 2011/0306859 A1 | 12/2011 | Saldivar et al. |
| 2011/0306867 A1 | 12/2011 | Gopinathan et al. |
| 2011/0313293 A1 | 12/2011 | Lindekugel et al. |
| 2012/0004564 A1 | 1/2012 | Dobak, III |
| 2012/0035460 A1 | 2/2012 | Stangenes et al. |
| 2012/0046562 A1 | 2/2012 | Powers et al. |
| 2012/0059249 A1 | 3/2012 | Verard et al. |
| 2012/0059270 A1* | 3/2012 | Grunwald ............. A61B 5/042 600/509 |
| 2012/0059271 A1 | 3/2012 | Amitai et al. |
| 2012/0071751 A1 | 3/2012 | Sra et al. |
| 2012/0071759 A1 | 3/2012 | Hagy et al. |
| 2012/0071782 A1 | 3/2012 | Patil et al. |
| 2012/0078342 A1 | 3/2012 | Vollkron et al. |
| 2012/0095319 A1 | 4/2012 | Kondrosky et al. |
| 2012/0108950 A1 | 5/2012 | He et al. |
| 2012/0115007 A1 | 5/2012 | Felder et al. |
| 2012/0136242 A1* | 5/2012 | Qi ............. A61B 8/0841 600/424 |
| 2012/0143029 A1 | 6/2012 | Silverstein et al. |
| 2012/0143078 A1 | 6/2012 | Kassab et al. |
| 2012/0172727 A1 | 7/2012 | Hastings et al. |
| 2012/0220854 A1 | 8/2012 | Messerly et al. |
| 2012/0265084 A1 | 10/2012 | Stewart et al. |
| 2012/0283582 A1 | 11/2012 | Mahapatra et al. |
| 2012/0296200 A1 | 11/2012 | Shachar et al. |
| 2012/0310052 A1 | 12/2012 | Mahapatra et al. |
| 2012/0310066 A1 | 12/2012 | Shachar et al. |
| 2012/0310660 A1 | 12/2012 | Liu et al. |
| 2012/0316440 A1 | 12/2012 | Munrow et al. |
| 2013/0006100 A1 | 1/2013 | Shachar et al. |
| 2013/0006102 A1 | 1/2013 | Wilkes et al. |
| 2013/0018248 A1 | 1/2013 | Hurezan |
| 2013/0035590 A1 | 2/2013 | Ma et al. |
| 2013/0041254 A1 | 2/2013 | Hagy et al. |
| 2013/0041269 A1 | 2/2013 | Stahmann et al. |
| 2013/0060116 A1 | 3/2013 | Messerly et al. |
| 2013/0079628 A1 | 3/2013 | Groszmann et al. |
| 2013/0085416 A1 | 4/2013 | Mest |
| 2013/0090938 A1 | 4/2013 | Fishman et al. |
| 2013/0102890 A1 | 4/2013 | Dib |
| 2013/0123597 A1 | 5/2013 | Rothenberg |
| 2013/0131503 A1 | 5/2013 | Schneider et al. |
| 2013/0169272 A1 | 7/2013 | Eichler et al. |
| 2013/0217999 A1 | 8/2013 | Burnside et al. |
| 2013/0245434 A1 | 9/2013 | Messerly et al. |
| 2013/0281837 A1 | 10/2013 | Ridley et al. |
| 2013/0289417 A1 | 10/2013 | Grunwald et al. |
| 2013/0296691 A1 | 11/2013 | Ashe |
| 2013/0296693 A1 | 11/2013 | Wenzel et al. |
| 2013/0303878 A1 | 11/2013 | Nevo et al. |
| 2013/0303896 A1 | 11/2013 | Kalpin et al. |
| 2013/0303945 A1 | 11/2013 | Blumenkranz et al. |
| 2013/0317338 A1 | 11/2013 | Silverstein |
| 2013/0324841 A1 | 12/2013 | Kamen et al. |
| 2013/0338503 A1 | 12/2013 | Cohen et al. |
| 2013/0338517 A1 | 12/2013 | Rothenberg |
| 2013/0345555 A1 | 12/2013 | Kanade et al. |
| 2014/0031674 A1 | 1/2014 | Newman et al. |
| 2014/0046261 A1 | 2/2014 | Newman et al. |
| 2014/0089836 A1 | 3/2014 | Damani et al. |
| 2014/0094694 A1 | 4/2014 | Moctezuma de la Barrera |
| 2014/0094768 A1 | 4/2014 | Stangenes et al. |
| 2014/0107475 A1 | 4/2014 | Cox et al. |
| 2014/0128712 A1 | 5/2014 | Banet et al. |
| 2014/0163356 A2 | 6/2014 | Burnside et al. |
| 2014/0180074 A1 | 6/2014 | Green et al. |
| 2014/0187917 A1 | 7/2014 | Clark et al. |
| 2014/0187990 A1 | 7/2014 | Banet et al. |
| 2014/0188133 A1 | 7/2014 | Misener |
| 2014/0221862 A1 | 8/2014 | Tambe |
| 2014/0228689 A1 | 8/2014 | Ishikawa et al. |
| 2014/0243659 A1 | 8/2014 | Rothenberg |
| 2014/0249428 A1 | 9/2014 | Ingold, Jr. et al. |
| 2014/0249505 A1 | 9/2014 | Bukhman |
| 2014/0253270 A1 | 9/2014 | Nicholls et al. |
| 2014/0257080 A1 | 9/2014 | Dunbar et al. |
| 2014/0275957 A1 | 9/2014 | Lupotti |
| 2014/0275990 A1 | 9/2014 | Hagy et al. |
| 2014/0276010 A1 | 9/2014 | Anderson |
| 2014/0303492 A1 | 10/2014 | Burnside et al. |
| 2014/0309624 A1 | 10/2014 | Bown et al. |
| 2014/0343398 A1 | 11/2014 | He et al. |
| 2015/0005621 A1 | 1/2015 | Liu |
| 2015/0018701 A1 | 1/2015 | Cox et al. |
| 2015/0025365 A1 | 1/2015 | Esguerra Wilczynski et al. |
| 2015/0025402 A1 | 1/2015 | Rothenberg |
| 2015/0051489 A1 | 2/2015 | Caluser et al. |
| 2015/0073285 A1 | 3/2015 | Albert et al. |
| 2015/0080716 A1 | 3/2015 | Powers et al. |
| 2015/0209008 A1 | 7/2015 | Ridley et al. |
| 2015/0216445 A1 | 8/2015 | Carmeli et al. |

(56) References Cited

U.S. PATENT DOCUMENTS

| | | | |
|---|---|---|---|
| 2015/0216446 A1* | 8/2015 | Bukhman | A61B 5/061 600/409 |
| 2015/0223775 A1 | 8/2015 | Hamilton, Jr. | |
| 2015/0245809 A1 | 9/2015 | Hagy et al. | |
| 2015/0245872 A1 | 9/2015 | Hagy et al. | |
| 2015/0246247 A1 | 9/2015 | Binnekamp et al. | |
| 2015/0282734 A1 | 10/2015 | Schweikert et al. | |
| 2015/0289781 A1 | 10/2015 | Grunwald et al. | |
| 2015/0297114 A1 | 10/2015 | Cox et al. | |
| 2015/0317810 A1 | 11/2015 | Grunwald et al. | |
| 2015/0335310 A1 | 11/2015 | Bernstein et al. | |
| 2015/0335383 A9 | 11/2015 | Cohen | |
| 2016/0067449 A1 | 3/2016 | Misener et al. | |
| 2016/0278869 A1 | 9/2016 | Grunwald | |
| 2016/0374589 A1 | 12/2016 | Misener et al. | |
| 2017/0000367 A1 | 1/2017 | Grunwald | |
| 2017/0020561 A1 | 1/2017 | Cox et al. | |
| 2017/0079548 A1 | 3/2017 | Silverstein et al. | |
| 2017/0079552 A1 | 3/2017 | Grunwald | |
| 2017/0079615 A1 | 3/2017 | Burnside et al. | |
| 2017/0079681 A1 | 3/2017 | Burnside et al. | |
| 2017/0086782 A1 | 3/2017 | Hagy et al. | |
| 2017/0151022 A1 | 6/2017 | Jascob et al. | |
| 2017/0215762 A1 | 8/2017 | Burnside et al. | |
| 2017/0231700 A1 | 8/2017 | Cox et al. | |
| 2017/0281029 A1 | 10/2017 | Messerly et al. | |
| 2018/0070856 A1 | 3/2018 | Grunwald | |
| 2018/0116551 A1 | 5/2018 | Newman et al. | |
| 2018/0145443 A1 | 5/2018 | Andreason et al. | |
| 2018/0169389 A1 | 6/2018 | Lemon et al. | |
| 2018/0296122 A1* | 10/2018 | Messerly | A61B 5/042 |
| 2019/0069877 A1 | 3/2019 | Burnside et al. | |
| 2019/0099108 A1 | 4/2019 | Messerly et al. | |
| 2019/0246945 A1 | 8/2019 | Grunwald | |
| 2019/0290208 A1* | 9/2019 | Toth | A61B 5/0402 |
| 2019/0320982 A1 | 10/2019 | Misener et al. | |
| 2020/0054858 A1 | 2/2020 | Newman et al. | |
| 2020/0119488 A1 | 4/2020 | Stats et al. | |
| 2020/0138332 A1 | 5/2020 | Newman et al. | |
| 2020/0237255 A1 | 7/2020 | Silverstein et al. | |
| 2020/0237403 A1 | 7/2020 | Southard et al. | |

FOREIGN PATENT DOCUMENTS

| | | |
|---|---|---|
| AU | 20009592 | 9/2000 |
| AU | 20015250 | 6/2001 |
| AU | 768362 B2 | 12/2003 |
| AU | 2001229024 B2 | 9/2005 |
| AU | 2001283703 B2 | 5/2006 |
| AU | 2006904933 | 9/2006 |
| AU | 2006202149 B2 | 3/2009 |
| AU | 2006283022 B2 | 2/2012 |
| CA | 1197745 A | 12/1985 |
| CA | 2420676 C | 7/2010 |
| CA | 2619909 C | 1/2014 |
| CN | 2031655 U | 2/1989 |
| CN | 1672649 A | 9/2005 |
| CN | 1913833 A | 2/2007 |
| CN | 101854853 A | 10/2010 |
| CN | 102209490 A | 10/2011 |
| CN | 102802514 A | 11/2012 |
| CN | 102821679 A | 12/2012 |
| CN | 103037761 A | 4/2013 |
| CN | 103037762 A | 4/2013 |
| CN | 103118591 A | 5/2013 |
| CN | 103189009 A | 7/2013 |
| DE | 4319033 C1 | 6/1994 |
| EP | 0362821 A1 | 4/1990 |
| EP | 0399536 A1 | 11/1990 |
| EP | 0359697 B1 | 11/1994 |
| EP | 0823261 A2 | 2/1998 |
| EP | 0928976 A2 | 7/1999 |
| EP | 1025805 A1 | 8/2000 |
| EP | 1015967 B1 | 4/2002 |
| EP | 1311226 A1 | 5/2003 |
| EP | 1504713 A1 | 2/2005 |
| EP | 1117331 B1 | 5/2005 |
| EP | 1117332 B1 | 8/2005 |
| EP | 1118019 B1 | 5/2006 |
| EP | 1717601 A2 | 11/2006 |
| EP | 1887940 A2 | 2/2008 |
| EP | 1932477 A1 | 6/2008 |
| EP | 2337491 A1 | 6/2011 |
| EP | 2440122 A1 | 4/2012 |
| EP | 2464407 A2 | 6/2012 |
| EP | 2482719 A1 | 8/2012 |
| EP | 2531098 A1 | 12/2012 |
| EP | 2575610 A1 | 4/2013 |
| EP | 2575611 A1 | 4/2013 |
| EP | 2603145 A2 | 6/2013 |
| EP | 2605699 A2 | 6/2013 |
| EP | 2474268 B1 | 7/2013 |
| EP | 2618727 A1 | 7/2013 |
| EP | 2632360 A1 | 9/2013 |
| EP | 2219526 B1 | 3/2014 |
| EP | 2712547 A1 | 4/2014 |
| EP | 2313143 B1 | 9/2014 |
| EP | 2992825 B1 | 5/2017 |
| EP | 2170162 B1 | 8/2017 |
| EP | 2265175 B1 | 8/2017 |
| FR | 2545349 B1 | 9/1986 |
| JP | 01097440 | 4/1989 |
| JP | 03173542 A | 7/1991 |
| JP | 9-503054 | 3/1997 |
| JP | 09-094298 A | 4/1997 |
| JP | 10043310 | 2/1998 |
| JP | 10290839 A | 11/1998 |
| JP | 11128237 A | 5/1999 |
| JP | 2001-145630 A | 5/2001 |
| JP | 2001161683 A | 6/2001 |
| JP | 2001-514533 A | 9/2001 |
| JP | 2001-524339 A | 12/2001 |
| JP | 2001340334 A | 12/2001 |
| JP | 2002520893 A | 7/2002 |
| JP | 2002-224069 A | 8/2002 |
| JP | 2002-529133 A | 9/2002 |
| JP | 2002-541947 A | 12/2002 |
| JP | 2003-010138 A | 1/2003 |
| JP | 2003501127 A | 1/2003 |
| JP | 2003061752 A | 3/2003 |
| JP | 2003299654 A | 10/2003 |
| JP | 2003334191 A | 11/2003 |
| JP | 2004505748 T | 2/2004 |
| JP | 2004515298 A | 5/2004 |
| JP | 2006508744 A | 3/2006 |
| JP | 2006-338526 A | 12/2006 |
| JP | 2007-000226 A | 1/2007 |
| JP | 2007-068989 A | 3/2007 |
| JP | 2007-105450 A | 4/2007 |
| JP | 2007-313122 A | 12/2007 |
| JP | 4090741 B2 | 5/2008 |
| JP | 2009/271123 A | 11/2009 |
| JP | 5010604 B2 | 8/2012 |
| JP | 2012-529929 A | 11/2012 |
| JP | 2013-518676 A | 5/2013 |
| JP | 2013-526959 A | 6/2013 |
| JP | 2013-526961 A | 6/2013 |
| RU | 2009101949 A | 7/2010 |
| WO | 1980002376 A1 | 11/1980 |
| WO | 1991012836 A1 | 9/1991 |
| WO | 1992003090 A1 | 3/1992 |
| WO | 1994003159 A1 | 2/1994 |
| WO | 1994004938 A1 | 3/1994 |
| WO | 1996005768 A1 | 2/1996 |
| WO | 1996007352 A1 | 3/1996 |
| WO | 1996041119 A1 | 12/1996 |
| WO | 1997/22395 A1 | 6/1997 |
| WO | 1997029683 A1 | 8/1997 |
| WO | 1997043989 A1 | 11/1997 |
| WO | 97/48438 A2 | 12/1997 |
| WO | 1998025159 A1 | 6/1998 |
| WO | 98/29032 A1 | 7/1998 |
| WO | 1998035611 A1 | 8/1998 |

(56) References Cited

FOREIGN PATENT DOCUMENTS

| | | |
|---|---|---|
| WO | 1999016495 A1 | 4/1999 |
| WO | 1999027837 A2 | 6/1999 |
| WO | 1999049407 A1 | 9/1999 |
| WO | 2000019906 A1 | 4/2000 |
| WO | 2000027281 A1 | 5/2000 |
| WO | 2000040155 A1 | 7/2000 |
| WO | 2000063658 A2 | 10/2000 |
| WO | 2000074775 A1 | 12/2000 |
| WO | 2001013792 A1 | 3/2001 |
| WO | 2001039683 A1 | 6/2001 |
| WO | 2001076479 A1 | 10/2001 |
| WO | 02/07794 A2 | 1/2002 |
| WO | 2002015973 A1 | 2/2002 |
| WO | 2002019905 A1 | 3/2002 |
| WO | 2002025277 A1 | 3/2002 |
| WO | 2002085442 A1 | 10/2002 |
| WO | 2003061752 A1 | 7/2003 |
| WO | 2003077759 A1 | 9/2003 |
| WO | 03/088833 A1 | 10/2003 |
| WO | 2003091495 A1 | 11/2003 |
| WO | 2004002303 A1 | 1/2004 |
| WO | 2004049970 A2 | 6/2004 |
| WO | 2005033524 A1 | 4/2005 |
| WO | 2005033574 A1 | 4/2005 |
| WO | 2005/089851 A1 | 9/2005 |
| WO | 2005117690 A1 | 12/2005 |
| WO | 2005117733 A2 | 12/2005 |
| WO | 2006074509 A1 | 7/2006 |
| WO | 2006074510 A1 | 7/2006 |
| WO | 2006078677 A2 | 7/2006 |
| WO | 2006103661 A2 | 10/2006 |
| WO | 2006111056 A1 | 10/2006 |
| WO | 2007002541 A2 | 1/2007 |
| WO | 2007005976 A1 | 1/2007 |
| WO | 2007014447 A1 | 2/2007 |
| WO | 2007034196 A2 | 3/2007 |
| WO | 2007067324 A1 | 6/2007 |
| WO | 2007069168 A2 | 6/2007 |
| WO | 2007109123 A2 | 9/2007 |
| WO | 2007126536 A2 | 11/2007 |
| WO | 2007144894 A1 | 12/2007 |
| WO | 2008005480 A1 | 1/2008 |
| WO | 2008024596 A2 | 2/2008 |
| WO | 2008028253 A1 | 3/2008 |
| WO | 2008083111 A1 | 7/2008 |
| WO | 2008097767 A2 | 8/2008 |
| WO | 2008118992 A1 | 10/2008 |
| WO | 2008126074 A2 | 10/2008 |
| WO | 2008129326 A1 | 10/2008 |
| WO | 2008131017 A2 | 10/2008 |
| WO | 2008136008 A2 | 11/2008 |
| WO | 2009000439 A1 | 12/2008 |
| WO | 2009002514 A2 | 12/2008 |
| WO | 2009003138 A1 | 12/2008 |
| WO | 2009009064 A1 | 1/2009 |
| WO | 2009057774 A1 | 5/2009 |
| WO | 2009063166 A1 | 5/2009 |
| WO | 2009067654 A1 | 5/2009 |
| WO | 2009070616 A2 | 6/2009 |
| WO | 2009100158 A1 | 8/2009 |
| WO | 2009123819 A2 | 10/2009 |
| WO | 2009126340 A1 | 10/2009 |
| WO | 2009129475 A1 | 10/2009 |
| WO | 2009129477 A1 | 10/2009 |
| WO | 2009134605 A2 | 11/2009 |
| WO | 2009137262 A2 | 11/2009 |
| WO | 2010002313 A1 | 1/2010 |
| WO | 2010018500 A1 | 2/2010 |
| WO | 2010022370 A1 | 2/2010 |
| WO | 2010027349 A1 | 3/2010 |
| WO | 2010027471 A2 | 3/2010 |
| WO | 2010029906 A1 | 3/2010 |
| WO | 2010030820 A1 | 3/2010 |
| WO | 2010132857 A1 | 11/2010 |
| WO | 2010132985 A1 | 11/2010 |
| WO | 2010/144922 A1 | 12/2010 |
| WO | 2010143196 A1 | 12/2010 |
| WO | 2011019760 A2 | 2/2011 |
| WO | 2011041450 A1 | 4/2011 |
| WO | 2011044421 A1 | 4/2011 |
| WO | 2011057289 A2 | 5/2011 |
| WO | 2011064209 A1 | 6/2011 |
| WO | 2011084593 A2 | 7/2011 |
| WO | 2011097312 A1 | 8/2011 |
| WO | 2011128052 A2 | 10/2011 |
| WO | 2011150358 A1 | 12/2011 |
| WO | 2011150376 A1 | 12/2011 |
| WO | 2012021542 A2 | 2/2012 |
| WO | 2012024577 A2 | 2/2012 |
| WO | 2012039866 A1 | 3/2012 |
| WO | 2012040487 A1 | 3/2012 |
| WO | 2012058461 A1 | 5/2012 |
| WO | 2012083245 A1 | 6/2012 |
| WO | 2012088535 A1 | 6/2012 |
| WO | 2012110955 A1 | 8/2012 |
| WO | 2012173697 A1 | 12/2012 |
| WO | 2013006713 A2 | 1/2013 |
| WO | 2013006817 A1 | 1/2013 |
| WO | 2013034175 A1 | 3/2013 |
| WO | 2014042329 A1 | 3/2014 |
| WO | 2014052894 A2 | 4/2014 |
| WO | 2014062728 A1 | 4/2014 |
| WO | 2014138652 A1 | 9/2014 |
| WO | 2014138918 A1 | 9/2014 |
| WO | 2015/055797 A1 | 4/2015 |
| WO | 2015048514 A1 | 4/2015 |
| WO | 2015073962 A1 | 5/2015 |
| WO | 2015/120256 A2 | 8/2015 |
| WO | 2016/210325 A1 | 12/2016 |
| WO | 2018/112252 A1 | 6/2018 |
| WO | 2020/160315 A1 | 8/2020 |

OTHER PUBLICATIONS

Palesty, JA et al, Routine Chest Radiographs Following Central Venous Recatherization over a Wire are not Justified, Am J Surg, pp. 618-621, vol. 176 No. 6, Dec. 1998.

Paliotti, Roberta P. et al, Intravascular Doppler Technique for Monitoring Renal Venous Blood Flow in Man, J Nephrol, pp. 57-62, 2003.

Parker, K.H. et al, Cardiovascular Fluid Dynamics, Department of Bioengineering, National Heart and Lung Institute, Imperial College of Science, Technology and Medicine, Cardiovascular Haemodynamics, pp. 1-28, Sep. 26, 2005.

Pawlik, et al., "Central Venous Catheter Placement: Comparison of the Intravascular Guidewire and the Fluid Column Electrocardiograms." European Journal of Anaesthesiology, vol. 41, pp. 594-599, 2004.

PCT/US13/62409 filed Sep. 27, 2013 International Search Report and Written Opinion dated Feb. 24, 2014.

PCT/US2006/033079 filed Aug. 24, 2006 International Preliminary Report on Patentability dated Feb. 26, 2008.

PCT/US2006/033079 filed Aug. 24, 2006 Search Report dated Dec. 19, 2006.

PCT/US2006/033079 filed Aug. 24, 2006 Written Opinion dated Dec. 19, 2006.

PCT/US2008/060502 filed Apr. 16, 2008 International Search Report and Written Opinion dated Oct. 16, 2008.

PCT/US2008/084751 filed Nov. 25, 2008 International Preliminary Report on Patentability dated Jun. 1, 2010.

PCT/US2008/084751 filed Nov. 25, 2008 Search Report dated May 20, 2009.

PCT/US2008/084751 filed Nov. 25, 2008 Written Opinion dated May 20, 2009.

PCT/US2009/033116 filed Feb. 4, 2009 International Preliminary Report on Patentability dated Aug. 10, 2010.

PCT/US2009/033116 filed Feb. 4, 2009 Search Report dated Mar. 13, 2009.

PCT/US2009/033116 filed Feb. 4, 2009 Written Opinion dated Mar. 13, 2009.

(56) References Cited

OTHER PUBLICATIONS

PCT/US2009/041051 filed Apr. 17, 2009 International Preliminary Report on Patentability dated Apr. 8, 2014.
PCT/US2009/041051 filed Apr. 17, 2009 Search Report dated Jul. 28, 2009.
PCT/US2009/041051 filed Apr. 17, 2009 Written Opinion dated Jul. 28, 2009.
PCT/US2009/054687 filed Aug. 21, 2009 International Preliminary Report on Patentability dated Feb. 22, 2011.
PCT/US2009/054687 filed Aug. 21, 2009 Search Report dated Oct. 6, 2009.
PCT/US2009/054687 filed Aug. 21, 2009 Written Opinion dated Oct. 6, 2009.
PCT/US2009/056567 filed Sep. 10, 2009 International Preliminary Report on Patentability dated Mar. 15, 2011.
PCT/US2009/056567 filed Sep. 10, 2009 Search Report dated Nov. 6, 2009.
PCT/US2009/056567 filed Sep. 10, 2009 Written Opinion dated Nov. 6, 2009.
PCT/US2010/038555 filed Jun. 14, 2010 Search Report dated Oct. 5, 2010.
PCT/US2010/038555 filed Jun. 14, 2010 Written Opinion dated Oct. 5, 2010.
PCT/US2010/045084 filed Aug. 10, 2010 International Preliminary Report on Patentability dated Feb. 23, 2012.
PCT/US2010/045084 filed Aug. 10, 2010 Search Report dated Apr. 14, 2011.
PCT/US2010/045084 filed Aug. 10, 2010 Written Opinion dated Apr. 14, 2011.
PCT/US2010/050773 filed Sep. 29, 2010 Search Report dated Jan. 24, 2011.
PCT/US2010/050773 filed Sep. 29, 2010 Written Opinion dated Jan. 24, 2011.
PCT/US2010/051917 filed Oct. 8, 2010 Search Report dated Nov. 29, 2010.
PCT/US2010/051917 filed Oct. 8, 2010 Written Opinion dated Nov. 29, 2010.
PCT/US2011/023497 filed Feb. 2, 2011 Search Report dated Jun. 6, 2011.
PCT/US2011/023497 filed Feb. 2, 2011 Written Opinion dated Jun. 6, 2011.
PCT/US2011/038391 filed May 27, 2011 International Preliminary Report on Patentability and Written Opinion dated Dec. 4, 2012.
PCT/US2011/038391 filed May 27, 2011 International Search Report dated Sep. 21, 2011.
PCT/US2011/038415 filed May 27, 2011 International Preliminary Report on Patentability dated Dec. 13, 2012.
PCT/US2011/038415 filed May 27, 2011 International Search Report dated Sep. 28, 2011.
PCT/US2011/038415 filed May 27, 2011 Written Opinion dated Sep. 28, 2011.
PCT/US2011/047127 filed Aug. 9, 2011 International Preliminary Report on Patentability dated Apr. 18, 2013.
PCT/US2011/047127 filed Aug. 9, 2011 International Search Report dated Feb. 29, 2012.
PCT/US2011/047127 filed Aug. 9, 2011 Written Opinion dated Feb. 29, 2012.
PCT/US2011/048403 filed Aug. 19, 2011 International Preliminary Report on Patentability dated Jul. 30, 2013.
PCT/US2011/048403 filed Aug. 19, 2011 International Search Report dated Dec. 15, 2011.
PCT/US2011/048403 filed Aug. 19, 2011 Written Opinion dated Dec. 15, 2011.
PCT/US2011/052793 filed Sep. 22, 2011 International Preliminary Report on Patentability dated Apr. 4, 2013.
PCT/US2011/052793 filed Sep. 22, 2011 International Search Report dated Jan. 6, 2012.
PCT/US2011/052793 filed Sep. 22, 2011 Written Opinion dated Jan. 6, 2012.
AZoMaterials. Nickel-Based Super Alloy Inconel 625—Properties and Applications by United Pertormance Alloys. Oct. 27, 2015. Last accessed Mar. 23, 2018. <URL:https:I/web.archive.org/web/20151027202821/https://www.azom.com/article.aspx?ArticleID=4461>.
CA 2800810 filed Nov. 26, 2012 Office Action dated Mar. 13, 2018.
CA 2800813 filed Nov. 26, 2012 Office Action dated Mar. 5, 2018.
CN 201380051172.5 filed Mar. 30, 2015 Office Action dated Jan. 16, 2018.
CN 201480010988.8 filed Aug. 27, 2015 Office Action dated Dec. 13, 2017.
CN 201610127217.8 filed Mar. 7, 2016 Office Action dated Dec. 28, 2017.
CN 201610166569.4 filed Dec. 23, 2010, Office Action dated Nov. 1, 2017.
EP 14197137.4 filed Dec. 10, 2014 Office Action dated Apr. 5, 2018.
EP 15179061.5 filed Jul. 30, 2015 Partial European Search Report dated Jan. 17, 2018.
EP 17186624.7 filed Aug. 17, 2017 Extended European Search Report dated Jan. 17, 2018.
EP 17186624.7 filed Aug. 17, 2017 Partial European Search Report dated Jan. 17, 2018.
JP 2013-530322 filed Mar. 18, 2013, Office Action dated Nov. 6, 2017.
JP 2015-534770 filed Mar. 26, 2015 Office Action dated Feb. 21, 2018.
Mx/a/2015/004864 filed Apr. 16, 2015 Office Action dated Apr. 24, 2018.
Mx/a/2015/004864 filed Apr. 16, 2015 Office Action dated Dec. 18, 2017.
Not Resource Center. Magnetic Permeability. Oct. 18, 2014. Last accessed Mar. 23, 2018. <URL:https://web.archive.org/web/20141018213902/https://www.nde-ed.org/EducationResources/CommunityCollege/Materials/Physical_Chemical/Permeability.htm>.
PCT/US2017/066503 filed Dec. 14, 2017 International Search Report and Written Opinion dated Feb. 20, 2018.
RU 2015111669 filed Apr. 1, 2015 Office Action dated Jan. 25, 2018.
RU 2015111669 filed Apr. 1, 2015 Office Action dated May 18, 2018.
U.S. Appl. No. 13/665,420, filed Oct. 31, 2012 Notice of Allowance dated Feb. 7, 2018.
U.S. Appl. No. 13/890,158, filed May 8, 2013 Advisory Action dated Feb. 13, 2018.
U.S. Appl. No. 13/890,158, filed May 8, 2013 Notice of Allowance dated May 30, 2018.
U.S. Appl. No. 14/141,046, filed Dec. 26, 2013 Final Office Action dated Dec. 11, 2017.
U.S. Appl. No. 14/201,300, filed Mar. 7, 2014 Examiner's Answer dated Apr. 19, 2018.
U.S. Appl. No. 14/317,501, filed Jun. 27, 2014 Notice of Allowance dated Feb. 9, 2018.
U.S. Appl. No. 14/788,305, filed Jun. 30, 2015 Non-Final Office Action dated Jan. 10, 2018.
U.S. Appl. No. 15/192,561, filed Jun. 24, 2016 Non-Final Office Action dated Apr. 6, 2018.
U.S. Appl. No. 15/284,355, filed Oct. 3, 2016 Final Office Action dated May 24, 2018.
U.S. Appl. No. 15/365,698, filed Nov. 30, 2016 Non-Final Office Action dated Dec. 14, 2017.
U.S. Appl. No. 15/365,734, filed Nov. 30, 2016 Non-Final Office Action dated Feb. 23, 2018.
U.S. Appl. No. 15/365,734, filed Nov. 30, 2016 Notice of Allowance dated Jun. 4, 2018.
U.S. Appl. No. 15/365,752, filed Nov. 30, 2016 Non-Final Office Action dated Dec. 13, 2017.
U.S. Appl. No. 15/365,872, filed Nov. 30, 2016 Restriction Requirement dated Apr. 5, 2018.
U.S. Appl. No. 15/585,051, filed May 2, 2017 Final Office Action dated Feb. 28, 2018.
U.S. Appl. No. 15/585,051, filed May 2, 2017 Final Office Action dated Mar. 15, 2018.

(56) References Cited

OTHER PUBLICATIONS

U.S. Appl. No. 15/900,623, filed Feb. 20, 2018 Non-Final Office Action dated May 3, 2018.
U.S. Appl. No. 14/040,205, filed Sep. 27, 2013 Notice of Allowance dated Aug. 21, 2019.
U.S. Appl. No. 14/201,300, filed Mar. 7, 2014 Board Decision dated Jul. 23, 2019.
U.S. Appl. No. 14/996,247, filed Jan. 15, 2016 Non-Final Office Action dated Jul. 18, 2019.
U.S. Appl. No. 15/418,475, filed Jan. 27, 2017 Restriction Requirement dated Jul. 23, 2019.
U.S. Appl. No. 15/816,932, filed Nov. 17, 2017 Non-Final Office Action dated Aug. 22, 2019.
U.S. Appl. No. 15/900,623, filed Feb. 20, 2018 Non-Final Office Action dated Jul. 16, 2019.
U.S. Appl. No. 13/336,919, filed Dec. 23, 2011 Non-Final Office Action dated Dec. 27, 2013.
U.S. Appl. No. 13/336,919, filed Dec. 23, 2011 Non-Final Office Action dated Jul. 9, 2015.
U.S. Appl. No. 13/336,919, filed Dec. 23, 2011 Non-Final Office Action dated Oct. 16, 2012.
U.S. Appl. No. 13/336,919 filed Dec. 23, 2011 Notice of Allowance dated Jul. 26, 2016.
U.S. Appl. No. 13/337,987, filed Dec. 27, 2011 Examiner's Answer dated Jul. 2, 2014.
U.S. Appl. No. 13/337,987, filed Dec. 27, 2011 Final Office Action dated Sep. 19, 2013.
U.S. Appl. No. 13/337,987, filed Dec. 27, 2011 Non-Final Office Action dated Mar. 15, 2013.
U.S. Appl. No. 13/469,932, filed May 11, 2012 Advisory Action dated Jun. 27, 2016.
U.S. Appl. No. 13/469,932, filed May 11, 2012 Non-Final Office Action dated Jan. 3, 2014.
U.S. Appl. No. 13/469,932, filed May 11, 2012 Non-Final Office Action dated Jul. 31, 2014.
U.S. Appl. No. 13/469,932, filed May 11, 2012 Non-Final Office Action dated Sep. 4, 2015.
U.S. Appl. No. 13/469,932, filed May 11, 2012 Notice of Allowance dated Jan. 31, 2017.
U.S. Appl. No. 13/469,932, filed May 11, 2012 Final Office Action dated Apr. 7, 2016.
U.S. Appl. No. 13/665,420, filed Oct. 31, 2012 Final Office Action dated Apr. 8, 2016.
U.S. Appl. No. 13/665,420, filed Oct. 31, 2012 Non-Final Office Action dated Jan. 6, 2014.
U.S. Appl. No. 13/665,420, filed Oct. 31, 2012 Non-Final Office Action dated Jul. 9, 2015.
U.S. Appl. No. 13/665,420, filed Oct. 31, 2012 Non-Final Office Action dated Mar. 15, 2017.
U.S. Appl. No. 13/665,420, filed Oct. 31, 2012 Non-Final Office Action dated Oct. 9, 2014.
U.S. Appl. No. 13/737,806, filed Jan. 9, 2013 Notice of Allowance dated Oct. 31, 2013.
U.S. Appl. No. 13/858,782, filed Apr. 8, 2013 Notice of Allowance dated Oct. 9, 2014.
U.S. Appl. No. 13/887,166, filed May 3, 2013 Advisory Action dated Aug. 27, 2014.
U.S. Appl. No. 13/887,166, filed May 3, 2013 Appeal Decision dated Aug. 17, 2017.
U.S. Appl. No. 13/887,166, filed May 3, 2013 Examiner's Answer dated Jul. 16, 2015.
U.S. Appl. No. 13/887,166, filed May 3, 2013 Final Office Action dated Jun. 23, 2014.
U.S. Appl. No. 13/887,166, filed May 3, 2013 Non-Final Office Action dated Jan. 7, 2014.
U.S. Appl. No. 13/887,166, filed May 3, 2013 Notice of Allowance dated Nov. 6, 2017.
U.S. Appl. No. 13/890,158, filed May 8, 2013 Advisory Action dated Jul. 26, 2016.
U.S. Appl. No. 13/890,158, filed May 8, 2013 Final Office Action dated Nov. 21, 2017.
U.S. Appl. No. 13/890,158, filed May 8, 2013 Non-Final Office Action dated Apr. 7, 2017.
U.S. Appl. No. 13/890,158, filed May 8, 2013 Non-Final Office Action dated Aug. 15, 2014.
U.S. Appl. No. 13/890,158, filed May 8, 2013 Non-Final Office Action dated Jul. 9, 2015.
U.S. Appl. No. 13/969,265, filed Aug. 16, 2013 Non-Final Office Action dated Dec. 19, 2013.
U.S. Appl. No. 13/969,265, filed Aug. 16, 2013 Notice of Allowance dated Jun. 23, 2014.
U.S. Appl. No. 14/040,205, filed Sep. 27, 2013 Advisory Action dated Dec. 15, 2016.
U.S. Appl. No. 14/040,205, filed Sep. 27, 2013 Examiner's Answer dated Jul. 20, 2017.
U.S. Appl. No. 14/040,205, filed Sep. 27, 2013 Final Office Action dated Oct. 19, 2016.
U.S. Appl. No. 14/040,205, filed Sep. 27, 2013 Non-Final Office Action dated Mar. 10, 2016.
U.S. Appl. No. 14/054,700, filed Oct. 15, 2013 Advisory Action dated Dec. 15, 2016.
U.S. Appl. No. 14/054,700, filed Oct. 15, 2013 Examiner's Answer dated Jul. 3, 2017.
U.S. Appl. No. 14/054,700, filed Oct. 15, 2013 Final Office Action dated Oct. 19, 2016.
U.S. Appl. No. 14/141,046, filed Dec. 26, 2013 Advisory Action dated Aug. 4, 2016.
U.S. Appl. No. 14/141,046, filed Dec. 26, 2013 Final Office Action dated May 11, 2016.
U.S. Appl. No. 14/141,046, filed Dec. 26, 2013 Non-Final Office Action dated Apr. 7, 2017.
U.S. Appl. No. 14/141,046, filed Dec. 26, 2013 Non-Final Office Action dated Feb. 11, 2015.
U.S. Appl. No. 14/141,046, filed Dec. 26, 2013 Non-Final Office Action dated Jun. 20, 2014.
U.S. Appl. No. 14/141,046, filed Dec. 26, 2013 Non-Final Office Action dated Nov. 5, 2015.
U.S. Appl. No. 14/201,300, filed Mar. 7, 2014 Advisory Action dated Jul. 18, 2016.
U.S. Appl. No. 14/201,300, filed Mar. 7, 2014 Advisory Action dated Mar. 2, 2017.
U.S. Appl. No. 14/201,300, filed Mar. 7, 2014 Final Office Action dated Dec. 19, 2016.
U.S. Appl. No. 14/201,300, filed Mar. 7, 2014 Final Office Action dated Jul. 10, 2017.
U.S. Appl. No. 14/201,300, filed Mar. 7, 2014 Final Office Action dated May 5, 2016.
U.S. Appl. No. 14/201,300, filed Mar. 7, 2014 Non-Final Office Action dated Aug. 24, 2016.
U.S. Appl. No. 14/201,300, filed Mar. 7, 2014 Non-Final Office Action dated Jan. 6, 2016.
U.S. Appl. No. 14/201,300, filed Mar. 7, 2014 Non-Final Office Action dated Mar. 30, 2017.
U.S. Appl. No. 14/270,241, filed May 5, 2014 Non-Final Office Action dated Apr. 23, 2015.
U.S. Appl. No. 14/270,241, filed May 5, 2014 Notice of Allowance dated Oct. 7, 2015.
U.S. Appl. No. 14/309,511, filed Jun. 19, 2014 Non-Final Office Action, dated Sep. 24, 2015.
U.S. Appl. No. 14/309,511, filed Jun. 19, 2014 Notice of Allowance, dated Jul. 26, 2016.
U.S. Appl. No. 14/317,501, filed Jun. 27, 2014 Advisory Action dated Sep. 16, 2015.
U.S. Appl. No. 14/317,501, filed Jun. 27, 2014 Decision on Appeal dated Nov. 17, 2017.
U.S. Appl. No. 14/317,501, filed Jun. 27, 2014 Examiners Answer dated Jun. 30, 2016.
U.S. Appl. No. 14/317,501, filed Jun. 27, 2014 Final Office Action dated Jul. 1, 2015.
U.S. Appl. No. 14/317,501, filed Jun. 27, 2014 Non-Final Office Action dated Mar. 3, 2015.

(56) References Cited

OTHER PUBLICATIONS

U.S. Appl. No. 14/317,501, filed Jun. 27, 2014 Non-Final Office Action dated Sep. 12, 2014.
U.S. Appl. No. 14/449,061, filed Jul. 31, 2014 Final Office Action dated Nov. 6, 2015.
U.S. Appl. No. 14/449,061, filed Jul. 31, 2014 Non-Final Office Action dated Apr. 27, 2015.
U.S. Appl. No. 14/449,061, filed Jul. 31, 2014 Notice of Allowance dated Apr. 13, 2016.
U.S. Appl. No. 14/498,887, filed Sep. 26, 2014 Advisory Action dated Aug. 22, 2016.
U.S. Appl. No. 14/498,887, filed Sep. 26, 2014 Final Office Action dated Jun. 15, 2016.
U.S. Appl. No. 14/498,887, filed Sep. 26, 2014 Non-Final Office Action dated Feb. 19, 2016.
U.S. Appl. No. 14/506,552, filed Oct. 3, 2014 Non-Final Office Action dated Oct. 1, 2015.
U.S. Appl. No. 14/548,151, filed Nov. 19, 2014 Advisory Action dated Aug. 1, 2017.
U.S. Appl. No. 14/548,151, filed Nov. 19, 2014 Advisory Action dated Jul. 22, 2016.
U.S. Appl. No. 14/548,151, filed Nov. 19, 2014 Final Office Action dated Apr. 19, 2017.
U.S. Appl. No. 14/548,151, filed Nov. 19, 2014 Non-Final Office Action dated Jun. 5, 2015.
U.S. Appl. No. 14/548,151, filed Nov. 19, 2014 Non-Final Office Action dated Sep. 21, 2017.
U.S. Appl. No. 14/548,151, filed Nov. 19, 2014 Non-Final Office Action dated Sep. 28, 2016.
U.S. Appl. No. 14/615,932, filed Feb. 6, 2015 Non-Final Office dated Dec. 29, 2016.
U.S. Appl. No. 14/788,305, filed Jun. 30, 2015 Restriction Requirement dated Aug. 25, 2017.
U.S. Appl. No. 14/846,496, filed Sep. 4, 2015 Non-Final Office Action dated Nov. 25, 2016.
U.S. Appl. No. 15/160,958, filed May 20, 2016 Advisory Action dated Jul. 10, 2017.
U.S. Appl. No. 15/160,958, filed May 20, 2016 Final Office Action dated Apr. 21, 2017.
U.S. Appl. No. 15/160,958, filed May 20, 2016 Non-Final Office Action dated Dec. 15, 2016.
U.S. Appl. No. 15/160,958, filed May 20, 2016 Notice of Allowance dated Jul. 26, 2017.
U.S. Appl. No. 15/284,355, filed Oct. 3, 2016 Non-Final Office Action dated Apr. 24, 2017.
U.S. Appl. No. 15/284,355, filed Oct. 3, 2016 Non-Final Office Action dated Nov. 17, 2017.
U.S. Appl. No. 15/585,051, filed May 2, 2017 Non-Final Office Action dated Jul. 14, 2017.
U.S. Appl. No. 29/428,649, filed Aug. 1, 2012 Notice of Allowance dated Jul. 5, 2013.
Valdivieso, J.R. Perez, et al., Evaluation of a formula for optimal positioning of a central venous catheter inserted trough the right internal jugular vein, Rev. Esp. Anestesiol. Reanim. 2003; 50: 77-79.
VasoNova Inc, Vascular navigation system for accurate placement of PICCs, Start-Up Emerging Medical Ventures, pp. 44-45, vol. 14 No. 7, Jul.-Aug. 2009.
Vesely, Thomas M. et al., Central Venous Catheter Tip Position: A Continuing Controversy, J Vasc Intery Radiol 2003; 14:527-534.
VIASYS Health Care Inc. Cortrak © Fact Sheet, 2005.
VIASYS Healthcare MedSystems, Navigator® Benefits, 2008.
VIASYS Healthcare MedSystems, Navigator® Research in Cost Justification, 2008.
VIASYS MedSystems, Cortrak™ Systems Brochure, 2005.
Volcano ComboMap Features and Benefits/Technical Specifications, 2 pages, 2011.
Watters, et al. "Use of Electrocardiogram to Position Right Atrial Catheters During Surgery." Annals of Surgery, vol. 225, No. 2, pp. 165-171, 1997.
Welch Allyn Cardioperfect® PC-Based Resting ECG, 2003.
Wilson, R. G. et al, Right Atrial Electrocardiography in Placement of Central Venous Catheters, The Lancet, pp. 462-463, Feb. 27, 1988.
Wong, Jeffrey J. et al., Azygos Tip Placement for Hemodialysis Catheters in Patients with Superior Vena Cava Occlusion, Cardiovasc Intervent Radiol (2006) 29:143-146.
JP 2012-552060 filed Aug. 1, 2012 Second Office Action dated Nov. 6, 2015.
JP 2013-512046 filed Nov. 26, 2012 First Office Action dated Mar. 23, 2015.
JP 2013-512046 filed Nov. 26, 2012 Office Action dated Dec. 8, 2015.
JP 2013-512046 filed Nov. 26, 2012 Office Action dated May 16, 2016.
JP 2013-512051 filed Nov. 26, 2012 First Office Action dated Mar. 23, 2015.
JP 2013-524999 filed Jan. 22, 2013 First Office Action dated Jun. 1, 2015.
JP 2013-530322 filed Mar. 18, 2013, Office Action dated Mar. 2, 2017.
JP 2014-519081 filed Dec. 27, 2013 First Office Action dated Apr. 26, 2016.
JP 2015-534770 filed Mar. 26, 2015 Office Action dated Jun. 12, 2017.
JP2013-530322 filed Mar. 18, 2013, Office Action dated May 2, 2016.
JP2013-530322 filed Mar. 18, 2013, First Office Action dated Jul. 31, 2015.
Kim, Ko et al, Positioning Internal Jugular Venous Catheters using the Right Third Intercostal Space in Children, Acta Anaesthesiol Scand, pp. 1284-1286, vol. 47 No. 10, Nov. 2003.
Kjelstrup T et al, Positioning of Central Venous Catheters using ECG, Tidssk Nor Laegeforen, pp. 599-601, vol. 111 No. 5, Feb. 1999 (Abstract only).
Kofler, Julia, et al., Epinephrine application via an endotracheal airway and via the Combitube in esophageal position, Critical Care Medicine: May 2000, vol. 28: Issue 5, pp. 1445-1449.
Konings, MK, et al., Development of an intravascular impedance catheter for detection of fatty lesions in arteries, IEEE Trans Med Imaging Aug. 1997; 16(4):439-46.
Kowalski, CM et al, Migration of Central Venous Catheters: Implications for Initial Catheter Tip Positioning, J Vasc Interv Radiol, pp. 443-447, vol. 8 No. 3, May-Jun. 1997.
KR 10-2012-7000866 filed Jan. 11, 2012 First Office Action dated Jun. 16, 2016.
KR 10-2012-7000866 filed Jan. 11, 2012 Second Office Action dated Nov. 3, 2016.
KR 10-2013-7006933 filed Mar. 19, 2013 Office Action dated Aug. 7, 2017.
Leowenthal, MR et al, The Peripherally Inserted Central Catheter (PICC): A Prospective Study of its Natural History after Fossa Insertion, Anaesth Intensive Care, pp. 21-24; vol. 30 No. 1, Feb. 2002.
Lepage Ronan et al. ECG Segmentation and P-wave Feature Extraction: Application to Patients Prone to Atrial Fibrillation, IEEE/EMBS Proceedings, 23rd Annual Conference, Istanbul, Turkey, Oct. 25-28, 2001.
Liu , Ji-Bin et al, Catheter-Based Intraluminal Sonography, J Ultrasound Med, pp. 145-160, vol. 23, 2004.
Lucey, B et al, Routine Chest Radiographs after Central Line Insertion: Mandatory Postprocedural Evaluation or Unnecessary Waste of Resources?, Cardiovasc Intervent Radiol, pp. 381-384, vol. 22 No. 5, Sep.-Oct. 1999.
Lum, Phillip, A New Formula-Based Measurement Guide for Optimal Positioning of Central Venous Catheters, JAVA, vol. 9, No. 2, pp. 80-85, 2004.
Lynch, RE et al, A Procedure for Placing Pediatric Femoral Venous Catheter Tips near the Right Atrium, Pediatr Emerg Care, pp. 130-132, vol. 18 No. 2, Apr. 2002.

(56) References Cited

OTHER PUBLICATIONS

Madan, et al. "Right Atrial Electrocardiography: A Technique for the Placement of Central Venous Catheters for Chemotherapy or Intravenous Nutrition." British Journal of Surgery, vol. B1, pp. 1604-1605, 1994.

Madias, John E, Intracardiac (Superior Vena Cava/Right Atrial) ECGs using Saline Solution as the Conductive Medium for the Proper Positioning of the Shiley Hemodialysis Catheter: Is it Not Time to Forego the Postinsertion Chest Radiograph?, pp. 2363-2367, Chest, 2003.

Markovich, Mary B., Central Venous Catheter Tip Placement: Determination of Posterior Malposition—A Case Study, JAVA, vol. 11, No. 2, pp. 85-89, 2006.

Martin, Roy W, An Ultrasoundic Catheter for Intravascular Measurement of Blood Flow: Technical Details, IEEE Transactions on Sonics and Ultrasonics, vol. SU-27, No. 6, pp. 277-286, Nov. 1980.

McDonnall, "Intra-Atrial Electrocardiography (ECG) for Catheter Placement." Literature review prepared for Bard Access Systems, Oct. 2007.

McGee et al., "Accurate Placement of Central Venous Catheters: A Prospective, Randomize, Multicenter Trail." Critical Care Medicine, vol. 21 No. 8, Aug. 1993.

MedGraphics, CardioPerfect® Resting/Stress ECG System, 3 pages, 2001.

Michenfelder, John et al, Air Embolism During Neurosurgery—An Evaluation of Right-Atrial Catheters for Diagnosis and Treatment, JAMA, pp. 1353-1358, vol. 208, No. 8, May 26, 1969.

Michenfelder, John et al, Air Embolism During Neurosurgery. A New Method of Treatment, Anesthesia and Analgesia. Current Researches, pp. 390-395, vol. 45, No. 4, Jul.-Aug. 1966.

Microbird™ Miniaturized DC Magnetic Sensors for Intra-body Navigation and Localization, Specifications, 2005.

Micronix CathRite™ Cardiac Access Device Brochure. Jun. 2004.

Micronix Pty Ltd "CathRite" Guiding Styled Core Manufacturing, Jun. 15, 2006.

Moureau, Nancy L. et al., "Electrocardiogram (EKG) Guided Peripherally Inserted Central Catheter Placement and Tip Position: Results of a Trial to Replace Radiological Confirmation," Journal of the Association for Vascular Access, pp. 8-14, vol. 15, No. 1, 2010.

Murthy, Vrudhula et al, Analysis of Power Spectral Densities of Electrocardiograms, Mathematical Biosciences, pp. 41-51, vol. 12 No. 1-2, Oct. 1971.

MX/a/2012/013672 filed Nov. 23, 2012 First Office Action dated Aug. 10, 2015.

MX/a/2012/013858 filed Nov. 28, 2012 First Office Action dated Sep. 26, 2014.

MX/a/2012/013858 filed Nov. 28, 2012 Second Office Action dated Jun. 10, 2015.

MX/a/2013/001317 filed Jan. 31, 2013 First Office Action dated Nov. 26, 2015.

Nadroo, AM et al, Changes in Upper Extremity Position Cause Migration of Peripherally Inserted Central Catheters in Neonates, Pediatrics, pp. 131-136, vol. 110, Jul. 2002.

Nakatani, K et al, Accurate Placement of Central Venous Catheters—ECG-guided method vs Patient Height Method, MASUI, pp. 34-38, vol. 51 No. 1, Jan. 2002.

Nazarian, GK et al, Changes in Tunneled Catheter Tip Position when a patient is Upright, J Vasc Interv Radiol, pp. 437-441, vol. 8 No. 3, May-Jun. 1997.

Neurometer® CPT, Clinical Applications. Neurotron, Inc. website: www.neurotron.com/CLINAPS.html, last accessed Oct. 23, 2006.

Neurometer® CPT, Frequently Asked Questions. Neurotron, Inc. website: www.neurotron.com/CPTFAQ/html, last accessed Oct. 23, 2006.

Neurometer® CPT, Products Page Neurotron, Inc. website: www.neurotron.com/products.html, last accessed Oct. 23, 2006.

Neurometer® Electrodiagnostic Neuroselective Sensory Nerve Evaluation: Charts, Tables, Documents & Downloads. Neurotron, Inc. website: www.neurotron.com/downloads.html, last accessed Oct. 23, 2006.

Worley, Seth J. "Use of a Real-Time Three-Dimensional Magenetic Navigation System for Radiofrequency Ablation of Accessory Pathways." PACE, vol. 21 pp. 1636-1643, Aug. 1998.

Yilmazlar A et al, Complications of 1303 Central Venous Cannulations, J R Soc Med, pp. 319-321, vol. 90 No. 6, Jun. 1997 (Abstract only).

Yoon, SZ et al, Usefulness of the Carina as a Radiographic Landmark for Central Venous Catheter Placement in Paediatric Patients, Br J Anaesth, Jul. 2005.

Yoshida, Teruhisa et al, Detection of Concealed Left Sided Accessory Atrioventricular Pathway by P Wave Signal Averaged Electrocardiogram, J Am Coll Cardiol, pp. 55-62, 1999.

Zaaroor, et al. "Novel Magnetic Technology for Intraoperative Intracranial Frameless Navigation: In Vivo and in Vitro Results." Neurosurgery, vol. 48, No. 5. pp. 1100-1107, May 2001.

Zachariou, Zacharias et al., Intra-atrial ECG recording: a new and safe method for implantation of Broviac catheters in children, Pediatr Surg Int (1994) 9: 457-458.

Zaidi, Naveed A., et al. "Room temperature magnetic order in an organic magnet derived from polyaniline." 2004, Polymer, vol. 45, pp. 5683-5689.

PCT/US20111058138 filed Oct. 27, 2011 International Preliminary Report on Patentability dated May 10, 2013.

PCT/US2011/058138 filed Oct. 27, 2011 International Search Report dated Feb. 7, 2012.

PCT/US2011/058138 filed Oct. 27, 2011 Written Opinion dated Feb. 7, 2012.

PCT/US2011/067268 filed Dec. 23, 2011 International Preliminary Report on Patentability dated Jul. 4, 2013.

PCT/US2011/067268 filed Dec. 23, 2011 International Search Report and Written Opinion dated Apr. 27, 2012.

PCT/US2012/045814 filed Jul. 6, 2012 International Search Report and Written Opinion dated Oct. 1, 2012.

PCT/US2013/065121 filed Oct. 15, 2013 International Search Report and Written Opinion dated Jan. 16, 2014.

PCT/US2014/022019 filed Mar. 7, 2014 International Search Report and Written Opinion dated Jun. 11, 2014.

PCT/US2015/014795 filed Feb. 6, 2015 International Search Report and Written Opinion dated May 14, 2015.

PCT/US2016/039356 filed Jun. 24, 2016 International Search Report and Written Opinion dated Sep. 16, 2016.

Pennington, C.R., Right Atrial Thrombus: a Complication of Total Parenteral Nutrition, British Medical Journal, pp. 446-447, vol. 295, Aug. 15, 1987.

Petersen, J et al, Silicone Venous Access Devices Positioned with their Tip High in the Superior Vena Cava are More Likely to Malfunction, Am J Surg, pp. 38-41, vol. 178 No. 1, Jul. 1999.

Pittiruti, et al, "The intracavitary ECG method for positioning the tip of central venous catheters: results of an Italian multicenter study," J Vasc Access, pp. 1-9, Nov. 21, 2011.

Pittiruti, et al, Intracavitary EKG Monitoring: A reliable method for controlling tip position during and after PICC Insertion presentation in Catholic University, Rome, Italy in 2008.

Pittiruti, et al. "The EKG Method for Positioning the Tip of PICCs: Results from Two Preliminary Studies." JAVA, vol. 13, No. 4, pp. 179-185, 2008.

Pittiruti, et al. "The electrocardiographic method for positioning the tip of central venous catheters" JAVA, pp. 1-12, Feb. 12, 2011.

Polos, PG et al, Tips for Monitoring the Position of a Central Venous Catheter—How Placement can go awry—even when the anatomy is normal, J Crit Illn, pp. 660-674, vol. 8 No. 6, Jun. 1993 (Abstract only).

Pop, Gheorghe A. et al., Catheter-based impedance measurements in the right atrium for continuously monitoring hematocrit and estimating blood viscosity changes; an in vivo feasibility study in swine, Biosensors and Bioelectronics 19 (2004) 1685-1693.

Popp, M. B. et al., Accuracy of implanted port placement with the use of the electromagnetic CathTrack® catheter locator system, The Journal of Vascular Access 2005; 6: 9-12.

Randolph AG et al, Ultrasound guidance for placement of central venous catheters: a meta-analysis of the literature, Critcal Care Medicine, pp. 2053-2058, vol. 24, Dec. 1996.

(56) References Cited

OTHER PUBLICATIONS

Reece, A et al, Posititioning Long Lines: Contrast Versus Plain Radiography, Arch Dis Child Fetal Neonatal Ed, pp. 129-130, vol. 84 No. 2, Mar. 2001.

Reynolds, N et al, Assessment of Distal Tip Position of Long Term Central Venous Feeding Catheters using Transesophageal Echocardiology, JPEN J Parenter Enteral Nutr, pp. 39-41, vol. 25 No. 1, Jan.-Feb. 2001.

RU 2011150917 filed Dec. 15, 2011 First Office Action dated Apr. 24, 2014.

RU 2011150917 filed Dec. 15, 2011 Second Office Action dated Aug. 28, 2014.

RU 2013158008 filed Dec. 26, 2013 First Office Action dated May 27, 2016.

RU 2015111669 filed Apr. 1, 2015 Office Action dated Sep. 5, 2017.

Ruschulte, Heiner et al, Prevention of Central Venous Catheter related infections with chlorhex idine gluconate impregnated wound dressings: A randomized controlled trial, presented as an abstract at the Annual meeting of the European Society of Anaesthesiologists (ESA) in Madrid, Spain in Jun. 2006, 12 pages, Annals of Hematology, Jul. 14, 2008.

Rutherford, J. S. et al., Depth of Central Venous Catheterization: An Audit of Practice in a Cardiac Surgical Unit, Anaesth Intens Care 1994; 22: 267-271.

Sacolick, et al. "Electromagnetically Tracked Placement of a Peripherally Inserted Central Catheter." SPIE Medical Imaging, 2004 Proceedings.

Salem, et al. "A New Peripherally Implanted Subcutaneous Permanent Central Venous Access Device for Patients Requiring Chemotherapy." Journal of Clinical Oncology, vol. 11, No. 11, pp. 2181-2185, Nov. 1993.

Savary, D et al, Intra-atrial Monitoring to Add Insertion of a Central Venous Line in Pre-Hospital Emergency Care Journal Europeen des Urgences, pp. 75-78, vol. 17 No. 2, 2004.

Schafer et al. "Incorrect placement of a vena cava catheter and its prevention by intra-atrial ECG." Anaesthesist. Jan. 1988;37(1):49-51.

Schummer, et al. "Central Venous Catheters—The inability of 'intra-atrial ECG' to prove adequate positioning." British Journal of Anaesthesia, vol. 93, No. 2, pp. 193-198, 2004.

Schummer, W et al, ECG-guided Central Venous Catheter Positioning: Does it detect the Pericardial Reflection rather than the Right Atrium?, Eur J Anaesthesiol, pp. 600-605, vol. 21 No. 8, Aug. 2004 (Abstract only).

Schummer, W et al, Intra-Atrial ECG is not a Reliable Method for Positioning Left Internal Jugular Vein Catheters, Br J Anaesth, pp. 481-486, vol. 91 No. 4, Oct. 2003.

Schummer, W, Central Venous Catheter—the Inability of "Intra-Atrial ECG" to prove Adequate Positioning, Br J Anaesth, pp. 193-198, vol. 93 No. 2, Aug. 2004.

Schuster, M. et al., The carina as a landmark in central venous catheter placement, British Journal of Anaesthesia 85 (2): 192-4 (2000).

Siela, Debra, Using Chest Radiography in the Intensive Care Unit, Crit Care Nurse Aug. 1, 2002 vol. 22 No. 4, pp. 18-27.

Simon, et al., "Central Venous Catheter Placement in Children: Evaluation of Electrocardiography Using J-Wire." Paediatric Anaesthesia vol. 9, pp. 501-504, 1999.

Smith, Brigham, et al., Intravenous electrocardiographic guidance for placement of peripherally inserted central catheters, Journal of Electrocardiology 43 (2010) 274-278.

Stark, DD et al, Radiographic Assessment of Venous Catheter Position in Children: Value of the Lateral View, Pediatric Radiology, pp. 76-80, vol. 14 No. 2, 1984.

Starkhammar et al. "Cath-Finder Catheter Tracking System: A New Device for Positioning of Central Venous Catheters. Early Experience from Implantation of Brachial portal Systems." Acta Anaesthesiol Scandinavia, vol. 34, No. 4 pp. 296-300, May 1990.

Starkhammer, H et al, Central Venous Catheter Placement using Electromagnetic Position Sensing: A Clinical Evaluation, Biomed. Instrum Technol, vol. 30 No. 2, pp. 164-170; Mar.-Apr. 1996.

Starr, David S et al, EKG Guided Placement of Subclavian CVP Catheters Using J-Wire, pp. 673-676, Ann. Surg, Dec. 1986.

Stas, M et al, Peroperative Intravasal Electrographic Control of Catheter Tip Position in Access Ports Placed by Venous Cut-Down Technique, EJSO, pp. 316-320, vol. 27, 2001.

Stereotaxis Magetic Navigation System with Navigan™ User Interface, 2005 Brochure.

Stereotaxis, Expanding the Possibilites of Interventional Medicine: Remote Navigation and Automation, pp. 1-8, Apr. 2011.

Tepa® Health Innovation PC based ECG System Introduction and Technical Specifications, EKG Master USB, 2 pages, Nov. 2003.

The FloWire Doppler Guide Wire located <http://www.volcanocorp.com/products/flowire-doppler-guide-wire.php>, 2011.

Traxal Technologies, Tracking Technology website overview: www.traxal.com/rd/rd_classroom_trackingtechnology.htm, last accessed Dec. 1, 2006.

Chen, Zhongping et al, Optical Doppler Tomography: Imaging in vivo Blood Flow Dynamics Following Pharmacological Intervention and Photodynamic Therapy, 7 pages, vol. 67, Photochemistry and Photobiology, 1998.

Cheng, KI et al, A Novel Approach of Intravenous Electrocardiograph Technique in Correct Position the Long-Term Central Venous Catheter, Kaohsiung J Med Sci, pp. 241-247, vol. 16 No. 5, May 2000 (Abstract only).

Cheung, P., et al., The Effect of a Disposable Probe Cover on Pulse Oximetry, Anaesth Intensive Care 2002; 30: 211-214.

Chu, et al., "Accurate Central Venous Port-A Catheter Placement: Intravenous Electrocardiography and Surface Landmark Techniques Compared by Using Transesophageal Echocardiography." The International Anesthesia Research Society, vol. 98, pp. 910-914, 2004.

Claasz, Antonia et al, A Study of the Relationship of the Superior Vena Cava to the Bony Landmarks of the Sternum in the Supine Adult: Implications for Magnetic Guidance Systems, Journal, vol. 12 No. 3, JAVA, Jul. 24, 2007.

Clifford, et al. "Assessment of Hepatic Motion Secondary to Respiration for Computer Assisted Interventions." Computer Aided Surgery, vol. 7, pp. 291-299, 2002.

CN 200880012117.4 filed Apr. 16, 2008 First Office Action dated Dec. 23, 2011.

CN 200880012117.4 filed Apr. 16, 2008 Fourth Office Action dated Sep. 4, 2013.

CN 200880012117.4 filed Apr. 16, 2008 Second Office Action dated Oct. 8, 2012.

CN 200880012117.4 filed Apr. 16, 2008 Third Office Action dated Apr. 27, 2013.

CN 200880125528.4 filed Nov. 25, 2008 First Office Action dated Jun. 5, 2012.

CN 200880125528.4 filed Nov. 25, 2008 Second Office Action dated Mar. 6, 2013.

CN 200880125528.4 filed Nov. 25, 2008 Third Office Action dated Jul. 1, 2013.

CN 200980123021.X filed Dec. 17, 2010 First Office Action dated Nov. 19, 2012.

CN 200980123021.X filed Dec. 17, 2010 Second Office Action dated Aug. 13, 2013.

CN 200980123021.X filed Dec. 17, 2010 Third Office Action dated Apr. 22, 2014.

CN 200980144663.8 filed May 9, 2011 Decision of Re-Examination dated Feb. 21, 2017.

CN 200980144663.8 filed May 9, 2011 Fifth Office Action dated May 26, 2015.

CN 200980144663.8 filed May 9, 2011 First Office Action dated Dec. 5, 2012.

CN 200980144663.8 filed May 9, 2011 Fourth Office Action dated Nov. 15, 2014.

CN 200980144663.8 filed May 9, 2011 Notice of Reexamination dated Aug. 5, 2016.

CN 200980144663.8 filed May 9, 2011 Second Office Action dated Aug. 22, 2013.

(56) References Cited

OTHER PUBLICATIONS

CN 200980144663.8 filed May 9, 2011 Third Office Action dated May 4, 2014.
CN 201080035659.0 filed Feb. 10, 2012 First Office Action dated Jan. 26, 2014.
CN 201080035659.0 filed Feb. 10, 2012 Second Office Action dated Oct. 9, 2014.
CN 201080035659.0 filed Feb. 10, 2012 Third Office Action dated Mar. 19, 2015.
CN 201080053838.7 filed May 28, 2012 First Office Action dated Jan. 6, 2014.
CN 201080053838.7 filed May 28, 2012 Fourth Office Action dated Jun. 2, 2015.
CN 201080053838.7 filed May 28, 2012 Second Office Action dated Jun. 17, 2014.
CN 201080053838.7 filed May 28, 2012 Third Office Action dated Dec. 4, 2014.
CN 201180016462.7 filed Sep. 27, 2012 First Office Action dated Mar. 21, 2014.
CN 201180016462.7 filed Sep. 27, 2012 Second Office Action dated Dec. 9, 2014.
CN 201180016462.7 filed Sep. 27, 2012 Third Office Action dated Jun. 10, 2015.
CN 201180037065.8 filed Jan. 28, 2013 First Office Action dated Sep. 28, 2014.
CN 201180037065.8 filed Jan. 28, 2013 Fourth Office Action dated May 5, 2016.
CN 201180037065.8 filed Jan. 28, 2013 Notice of Grant dated Aug. 30, 2016.
CN 201180037065.8 filed Jan. 28, 2013 Second Office Action dated Jun. 2, 2015.
CN 201180037065.8 filed Jan. 28, 2013 Third Office Action dated Nov. 24, 2015.
CN 201180037068.1 filed Jan. 28, 2013 First Office Action dated Apr. 20, 2015.
CN 201180037068.1 filed Jan. 28, 2013 First Office Action dated Sep. 9, 2014.
CN 201180037068.1 filed Jan. 28, 2013 Third Office Action dated Oct. 19, 2015.
CN 201180040151.4 filed Feb. 19, 2013 First Office Action dated Oct. 28, 2014.
CN 201180040151.4 filed Feb. 19, 2013 Office Action dated Dec. 10, 2015.
CN 201180040151.4 filed Feb. 19, 2013 Second Office Action dated Jun. 19, 2015.
CN 201180043512.0 filed Mar. 8, 2013 First Office Action dated Jul. 31, 2014.
CN 201180043512.0 filed Mar. 8, 2013 Second Office Action dated Apr. 14, 2015.
CN 201180052587.5 filed Apr. 28, 2013 First Office Action dated Jan. 26, 2015.
CN 201180052587.5 filed Apr. 28, 2013 Office Action dated Feb. 24, 2016.
CN 201180052587.5 filed Apr. 28, 2013 Second Office Action dated Aug. 19, 2015.
CN 201180068309.9 filed Aug. 22, 2013 First Office Action dated Oct. 16, 2014.
PCT/US2019/055716 filed Oct. 10, 2019 International Search Report and Written Opinion dated Feb. 4, 2020.
U.S. Appl. No. 14/141,046, filed Dec. 26, 2013 Board Decision dated Nov. 26, 2019.
U.S. Appl. No. 14/201,300, filed Mar. 7, 2014 Final Office Action dated Mar. 9, 2020.
U.S. Appl. No. 14/201,300, filed Mar. 7, 2014 Non-Final Office Action dated Nov. 27, 2019.
U.S. Appl. No. 14/996,247, filed Jan. 15, 2016 Advisory Action dated Feb. 20, 2020.
U.S. Appl. No. 14/996,247, filed Jan. 15, 2016 Final Office Action dated Dec. 11, 2019.
U.S. Appl. No. 15/365,698, filed Nov. 30, 2016 Notice of Allowance dated Nov. 4, 2019.
U.S. Appl. No. 15/418,475, filed Jan. 27, 2017 Final Office Action dated Apr. 2, 2020.
U.S. Appl. No. 15/418,475, filed Jan. 27, 2017 Non-Final Office Action dated Oct. 18, 2019.
U.S. Appl. No. 15/816,932, filed Nov. 17, 2017 Final Office Action dated Feb. 28, 2020.
U.S. Appl. No. 15/900,623, filed Feb. 20, 2018 Non-Final Office Action dated Dec. 30, 2019.
UAB Health Systems, Arrhythmias, retrieved from http://www.health,uab.edu/14564/ on Nov. 15, 2007, 12 pages.
U.S. Appl. No. 11/466,602, filed Aug. 23, 2006 Advisory Action dated Jun. 22, 2009.
U.S. Appl. No. 11/466,602, filed Aug. 23, 2006 Appeal Board Decision dated Sep. 17, 2012.
U.S. Appl. No. 11/466,602, filed Aug. 23, 2006 Final Office Action dated Apr. 8, 2010.
U.S. Appl. No. 11/466,602, filed Aug. 23, 2006 Final Office Action dated Jan. 30, 2009.
U.S. Appl. No. 11/466,602, filed Aug. 23, 2006 Final Office Action dated Oct. 28, 2013.
U.S. Appl. No. 11/466,602, filed Aug. 23, 2006 Non-Final Office Action dated Mar. 28, 2013.
U.S. Appl. No. 11/466,602, filed Aug. 23, 2006 Non-Final Office Action dated Sep. 25, 2009.
U.S. Appl. No. 11/466,602, filed Aug. 23, 2006 Notice of Allowance dated Dec. 3, 2012.
U.S. Appl. No. 11/466,602, filed Aug. 23, 2006 Notice of Allowance dated Mar. 14, 2014.
U.S. Appl. No. 11/552,094, filed Oct. 23, 2006 Notice of Allowability dated Apr. 2, 2010.
U.S. Appl. No. 11/552,094, filed Oct. 23, 2006 Non-Final Office Action dated Apr. 27, 2009.
U.S. Appl. No. 11/552,094, filed Oct. 23, 2006 Notice of Allowance dated May 20, 2010.
U.S. Appl. No. 12/104,253, filed Apr. 16, 2008 Final Office Action dated Jul. 27, 2011.
U.S. Appl. No. 12/104,253, filed Apr. 16, 2008 Non-Final Office Action dated Nov. 29, 2010.
U.S. Appl. No. 12/323,273, filed Nov. 25, 2008 Non-Final Office Action dated Jun. 8, 2012.
U.S. Appl. No. 12/369,625, filed Feb. 11, 2009 Final Office Action dated Feb. 23, 2012.
U.S. Appl. No. 12/369,625, filed Feb. 11, 2009 Notice of Allowance dated Oct. 5, 2012.
U.S. Appl. No. 12/369,625, filed Feb. 11, 2009 Notice of Panel Decision dated Aug. 1, 2012.
U.S. Appl. No. 12/369,625, filed Feb. 11, 2009 Non-Final Office Action dated Jul. 20, 2011.
U.S. Appl. No. 12/426,175, filed Apr. 17, 2009 Advisory Action dated Nov. 26, 2013.
U.S. Appl. No. 12/426,175, filed Apr. 17, 2009 Decision on Appeal dated Nov. 7, 2016.
U.S. Appl. No. 12/426,175, filed Apr. 17, 2009 Examiner's Answer dated Oct. 7, 2014.
U.S. Appl. No. 12/426,175, filed Apr. 17, 2009 Final Office Action dated Aug. 2, 2013.
U.S. Appl. No. 12/426,175, filed Apr. 17, 2009 Final Office Action dated Jan. 31, 2014.
U.S. Appl. No. 12/426,175, filed Apr. 17, 2009 Non-Final Office Action dated Dec. 3, 2012.
U.S. Appl. No. 12/426,175, filed Apr. 17, 2009 Notice of Allowance dated Dec. 13, 2016.
U.S. Appl. No. 12/427,244, filed Apr. 21, 2009 Non-Final Office Action dated Jan. 19, 2012.
U.S. Appl. No. 12/545,762, filed Aug. 21, 2009 Final Office Action dated Apr. 10, 2017.
U.S. Appl. No. 12/545,762, filed Aug. 21, 2009 Final Office Action dated Mar. 7, 2013.
U.S. Appl. No. 12/545,762, filed Aug. 21, 2009 Non-Final Office Action dated Aug. 1, 2012.

(56) References Cited

OTHER PUBLICATIONS

U.S. Appl. No. 12/545,762, filed Aug. 21, 2009 Non-Final Office Action dated Dec. 13, 2013.
U.S. Appl. No. 12/545,762, filed Aug. 21, 2009 Non-Final Office Action dated Feb. 16, 2016.
U.S. Appl. No. 12/545,762, filed Aug. 21, 2009 Non-Final Office Action dated Nov. 7, 2014.
U.S. Appl. No. 12/545,762, filed Aug. 21, 2009 Non-Final Office Action dated Sep. 11, 2015.
U.S. Appl. No. 12/545,762, filed Aug. 21, 2009 Non-Final Office Action dated Sep. 26, 2016.
U.S. Appl. No. 12/545,762, filed Aug. 21, 2009 Notice of Panel Decision dated Jul. 14, 2017.
U.S. Appl. No. 12/557,401, filed Sep. 10, 2009 Non-Final Office Action dated Apr. 24, 2012.
U.S. Appl. No. 12/557,401, filed Sep. 10, 2009 Non-Final Office Action dated Jan. 6, 2014.
U.S. Appl. No. 12/575,456, filed Oct. 7, 2009 Non-Final Office Action dated Oct. 5, 2012.
U.S. Appl. No. 12/715,556, filed Mar. 2, 2010 Final Office Action dated Oct. 2, 2013.
U.S. Appl. No. 12/715,556, filed Mar. 2, 2010 Non-Final Office Action dated Sep. 13, 2012.
U.S. Appl. No. 12/815,331, filed Jun. 14, 2010 Advisory Action dated Mar. 5, 2015.
U.S. Appl. No. 12/815,331, filed Jun. 14, 2010 Advisory Action dated Oct. 4, 2013.
U.S. Appl. No. 12/815,331, filed Jun. 14, 2010 Final Office Action dated Dec. 23, 2014.
U.S. Appl. No. 12/815,331, filed Jun. 14, 2010 Final Office Action dated Jul. 26, 2013.
U.S. Appl. No. 12/815,331, filed Jun. 14, 2010 Final Office Action dated Nov. 4, 2015.
U.S. Appl. No. 12/815,331, filed Jun. 14, 2010 Non-Final Office Action dated Jan. 22, 2013.
U.S. Appl. No. 12/815,331, filed Jun. 14, 2010 Non-Final Office Action dated Jul. 2, 2014.
U.S. Appl. No. 12/815,331, filed Jun. 14, 2010 Non-Final Office Action dated Jun. 1, 2015.
EP 12177438.4 filed Jul. 23, 2012 Examination Report dated Dec. 5, 2014.
EP 12177438.4 filed Jul. 23, 2012 extended European Search Report dated Mar. 25, 2013.
EP 12807886.2 filed Jan. 15, 2014 Extended European Search Report dated Feb. 6, 2015.
EP 13194818.4 filed Nov. 28, 2013 extended European search report dated Feb. 28, 2014.
EP 13840356.3 filed Apr. 27, 2015 Extended European Search Report dated Mar. 22, 2017.
EP 13840356.3 filed Apr. 27, 2015 Partial European Search Report dated Oct. 19, 2016.
EP 13846380.7 filed May 15, 2015 Extended European Search Report dated Sep. 30, 2016.
EP 13846380.7 filed May 15, 2015 Partial European Search Report dated Sep. 30, 2016.
EP 14151268.1 filed Jan. 15, 2014 European Search Report dated Feb. 21, 2014.
EP 14197137.4 filed Dec. 10, 2014 Extended European Search Report dated Nov. 4, 2015.
EP 14197137.4 filed Dec. 10, 2014 Office Action dated Sep. 20, 2017.
EP 14197137.4 filed Dec. 10, 2014, Partial European Search Report dated May 29, 2015.
EP 14761249.3 Filed Sep. 3, 2015 Extended European Search Report dated Sep. 19, 2016.
EP 14761249.3 Filed Sep. 3, 2015 Office Action dated Sep. 28, 2017.
EP 15179061.5 filed Jul. 30, 2015 Extended European Search Report dated Jan. 14, 2016.
EP 15746326.6 filed Jul. 1, 2016 Extended European Search Report dated Jun. 9, 2017.
EP 17157118.5 filed Feb. 21, 2017 Extended European Search Report Jun. 8, 2017.
EP14197136.6 filed Dec. 10, 2014 Extended European Search Report dated May 26, 2015.
Fearon, William F et al, Evaluating Intermediate Coronary Lesions in the Cardiac Catheterization Laboratory, vol. 4, No. 1, 7 pages, Reviews in Cardiovascular Medicine, 2003.
Felleiter P et al, Use of Electrocardiographic Placement Control of Central Venous Catheters in Austria, Acta Med Austriaca, pp. 109-113, vol. 26 No. 3, 1999 (Abstract only).
Forauer, AR et al, Change in Peripherally Inserted Central Catheter Tip Location with Abduction and Adduction of the Upper Extremity, J Vasc Interv Radiol, pp. 1315-1318, vol. 11 No. 10, Nov.-Dec. 2000.
Frassinelli, P et al, Utility of Chest Radiographs after Guidewire Exchanges of Central Venous Catheters, Crit Care Med, pp. 611-615, vol. 26 No. 3, Mar. 1998.
Frazin L et al, A Doppler Guided Retrograde Catheterization System, Cathet. Cardiovasc Diagn, pp. 41-50, May 1992.
French, PJ et al, Sensors for Catheter Applications, Sensors Update, vol. 13 Issue 1 pp. 107-153, Dec. 2003.
GB Application 0800474.9 filed Aug. 24, 2006 Office Action dated Aug. 9, 2010.
GB Application 0800474.9 filed Aug. 24, 2006 Office Action dated Mar. 17, 2010.
Gebauer, B et al, Ultrasound and Fluoroscopy-guided Implantation of Peripherally Inserted Central Venous catheters (PICCs), ROFO, pp. 386-391, vol. 176 No. 3, Mar. 2004 (Abstract only).
Gebhard, et al., "The accuracy of Electrocardiogram-Controlled Central Line Placement." The International Anesthesia Research Society, vol. 104, No. 1 Jan. 2007.
Gjendemsjo, Anders, et al., Energy and Power, The Connexions Project, Version 1.2, Feb. 20, 2004.
Gladwin, MT et al, Cannulation of the Internal Jugular Vein: is postpocedural chest radiography always necessary?, Crit Care Med, 33 pages, Oct. 2000.
Gonzales, et al. "Peripherally Inserted Central Catheter Placement in Swine Using Magnet Detection." Journal of Intravenous Nursing, vol. 22, No. 3, May/Jun. 1999.
Greenall, M.J. et al, Cardiac Tamponade and Central Venous Catheters, British Medical Journal, pp. 595-597, Jun. 14, 1975.
Guillory, "Basic Principles of Technologies for Catheter Localization." C.R. Bard internal paper, Oct. 20, 2004.
Guth, AA, Routine Chest X-rays after Insertion of Implantable Long-Term Venous Catheters: Necessary or Not?, Am Surg, pp. 26-29, vol. 67 No. 1, Jan. 2001 (Abstract only).
Hill, Bradley et al, Abstract of article discussing Vasallova VPS as guide for placement of PICCs. 2009.
Hill, Bradley, Identifying the Caval-Atrial Junction Using Smart-Catheter Technology presentation, 22nd Annual Scientific Meeting of the AVA in Savannah, Georgia, Sep. 13, 2008.
Hoffman, Thomas et al, Simultaneous Measurement of Pulmonary Venous Flow by Intravascular Catheter Doppler Velocimetry and Transesophageal Doppler Echocardiography: Relation to Left Atrial Pressure and Left Atrial and Left Ventricular Function, pp. 239-249, J Am Coll Cardiol, Jul. 1995.
Hoffmann, et al. "New Procedure in Transesophageal Echocardiography: Multiplane Transesophageal Echocardiography and Transesophageal Stress Echocardiography." Herz, vol. 18, No. 5, pp. 269-277, Oct. 1993.
Iacopino, Domenico Gerardo et al, Intraoperative Microvascular Doppler Monitoring of Blood Flow within a Spinal Dural Arteriovenous Fistula: A Precious Surgical Tool, vol. 10, 5 pages, Neurosurg. Focus, Feb. 2001.
Jeon, Yunseok et al., "Transesophageal Echocardiographic Evaluation of ECG-guided Central Venous Catheter Placement," Canadian Journal of Anesthesia, vol. 53, No. 10, Oct. 1, 2006, pp. 978-983.
Joosting, Jean-Pierre, "Dual-interface RFID-compatible EEPROM enables remote access to electronic device parameters," EE Times, Mar. 8, 2010.

(56) References Cited

OTHER PUBLICATIONS

JP 2008-528151 filed Aug 24, 2006 Notice of Grant dated May 6, 2012.
JP 2010-504220 filed Sep. 3, 2009 Final Office Action dated Apr. 18, 2013.
JP 2010-504220 filed Sep. 3, 2009 Office Action dated Apr. 1, 2014.
JP 2010-504220 filed Sep. 3, 2009 Office Action dated Apr. 18, 2013.
JP 2010-504220 filed Sep. 3, 2009 Office Action dated May 21, 2012.
JP 2010-535117 filed May 26, 2011 First Office Action dated Aug. 5, 2013.
JP 2012-515222 filed Dec. 9, 2011 Office Action dated Feb. 23, 2015.
JP 2012-515222 filed Dec. 9, 2011 Office Action dated Mar. 24, 2014.
JP 2012-552060 filed Aug. 1, 2012 Office Action dated Nov. 12, 2014.
"Ascension to Launch New 3D Guidance™ Tracker at TCT 2006." Press Releases from Ascension website: www.ascension-tech.com/news/press_101106.php, last accessed Dec. 1, 2006.
Acuson—The Value of Vision, AcuNav Diagnostic Ultrasound Catheter, 2000.
Advertising flyer for GAVECELT—The Italian Group for Long Term Venous Access Devices, for program on International Meeting on PICC's, Midline Catheters and Long Term Venous Access Devices in Catholic University, Rome, Italy on Dec. 3, 4, 5, 2008.
Alexander, GD et al, The Role of Nitrous Oxide in Postoperative Nausea and Vomiting, Collection of Abstracts Presented at the International Anesthesia Research Society by various speakers, 58th Congress, Mar. 12-14, 1984, Anesthesia and Analgesia, pp. 175-284, vol. 63, 1984.
Allan, P.L. et al, Role of Ultrsound in the Assessment of Chronic Venous Insufficiency, Ultrasound Quarterly, vol. 17, No. 1, pp. 3-10, 2001.
Andropoulos, et al. "A Controlled Study of the Transesophageal Echocardiography to Guide Central Venous Catheter Placement in Congetital Heart Surgery Patients." The International Anesthesia Research Society, vol. 89, pp. 65-70, 1999.
Anonymous author, Correct Catheter Placement with a low-impact, reliable and economical method, <http://www.cvc-partner.com/index.cfm?103A955CC6844BF58ACFE3C9C1471959>, last accessed Dec. 22, 2011.
Arai, J et al, Detection of Peripherally Inserted Central Catheter Occlusion by in-line Pressure Monitoring, Paediatr Anaesth, pp. 621-624, vol. 12 No. 7, Sep. 2002.
Arrow International, Inc., The Arrow-Johans RAECG Adapter-Making Proper Central Venous Catheter Placement More Reliable (Modle No. EG-04900), Technical Report 1987, USA.
Aslamy, et al. "MRI of Central Venous Anatomy: Implications for Central Venous Catheter Insertion." American College of Chest Physicians, Jun. 8, 2009.
AU 2006283022 filed Aug. 24, 2006 Office Action dated Dec. 22, 2010.
AU 2008329807 exam requested Aug. 13, 2012 Examination Report No. 1 dated Feb. 15, 2013.
AU 2008329807 exam requested Aug. 13, 2012 Notice of Acceptance dated Feb. 14, 2014.
AU 2010300677 filed Mar. 12, 2012 First Examination Report dated Mar. 9, 2014.
AU 2011289513 filed Jan. 21, 2013 Examiner's Report dated Jul. 5, 2013.
AU 2012202293 filed Apr. 19, 2012 Examination Report No. 1 dated Apr. 24, 2013.
AU 2012278809 filed Nov. 12, 2013 Notice of Acceptance dated Sep. 13, 2016.
AU 2013201648 filed Mar. 19, 2013 Examiner's Report dated Mar. 5, 2014.
AU 2013201648 filed Mar. 19, 2013 Examiner's Report dated Oct. 14, 2013.
AU 2013202824 filed Apr. 6, 2013 First Examiner's Report dated Mar. 10, 2014.
AU 2013204243 filed Apr. 12, 2013 Examiner's Report dated Jun. 5, 2013.
Aurora® System Technical Specifications, Oct. 2003.
B. Braun Website, "The Optimal Position of the Central Venous Catheter." http://www.cvcpartner.com/index.cfm18F1BDEA1310466194960A39F4E90968 (2009).
B. Braun, Certofix Central Venous Catheter for Placement Using the Seldinger Technique with Simultaneous ECG Lead Option, Feb. 2010.
Bailey, SH et al, Is Immediate Chest Radiograph Necessary after Central Venous Catheter Placement in a Surgical Intensive Care Unit?, Am J Surg, pp. 517-522, vol. 180 No. 6, Dec. 2000.
Bankier, Alexander A., Azygos Arch Cannulation by Central Venous Catheters: Radiographic Detection of Malposition and Subsequent Complications, Journal of Thoracic Imaging 12:64-69 (1997).
Barber, JM et al, A Nurse led Peripherally Inserted Central Catheter Line Insertion Service is Effective with Radiological Support, Clin Radiol, pp. 352-354, vol. 57 No. 5, May 2002.
Bard Access Systems, Sherlock Tip Location System, 5 pages, 2006.
Bard Access Systems, Site Rite Vascular Acess Ultrasound System, 4 pages, 2005.
Benchimol, Alberto at al, Right Atrium and Superior Vena Cava Flow Velocity in Man Measured with the Doppler-Catheter Flowmeter-Telemetry System, The Amer Journal of Medicine, pp. 303-309, vol. 48, Mar. 1970.
Benzadon, M. N. et al: "Comparison of the Amplitude of the P-Wave from Intracardiac Electrocardiogram Obtained by Means of a Central Venous Catheter Filled With Saline Solution to That Obtained Via Esophageal Electrocardiogram", American Journal of Cardiology, Cahners Publishing Co., Newton, MA, US, vol. 98, No. 7, Oct. 1, 2006 (Oct. 1, 2006), pp. 978-981.
BioAdvance Lumen Vu, Greenhouse Fund Feb. 2004 Recipient, www.bioadvance.com <http://www.bioadvance.com>, 2005.
Borgobello, Bridget, App allows users to view electrocardiograms on smartphones dated Oct. 15, 2010; printed from http://www.gizmag.com/app-to-view-electrocardiograms-on-smartphones/16664/ on Feb. 4, 2011.
Buehrle, Douglas, PICC Placement in Humans using Electromagnetic Detection, <http://www.corpakmedsystems.com/supplement_material/supplementpages/navigator/navarticle.html>, 2008.
C.R. Bard, CathTrack™ Catheter Location System at www.bardaccess.com <http://www.bardaccess.com>, last accessed Apr. 28, 2011.
C.R. Bard, Inc., Bard Electrophysiology Product Catalogue, Bard Catheters, pp. 74-75 (2002), USA.
CA 2,619,909 filed Aug. 24, 2006 Examiner's Report dated Oct. 26, 2012.
CA 2,721,715 filed Apr. 17, 2009 Examiner's Report dated Aug. 18, 2015.
CA 2,721,715 filed Apr. 17, 2009 Examiner's Report dated Oct. 25, 2016.
CA 2800810 filed Nov. 26, 2012 Office Action dated Mar. 30, 2017.
Cadman, A et al, To Clot or Not to Clot? That is the question in Central Venous Catheters, Clinical Radiology, pp. 349-355, vol. 59 No. 4, Apr. 2004.
Calvert, N et al, The Effectiveness and Cost-effectiveness of Ultrasound Locating Devices for Central Venous Access: A Systematic Review and Economic Evaluation, Health Technology Assessment, vol. 7, No. 12, 2003.
Cardella, John F. et al., Interventinal Radiologic Placement of Peripherally Inserted Central Catheters, Journal of Vascular and Interventional Radiology 1993; 4:653-660.
Carlon, R et al, Secondary Migration of a Central Venous Catheter—A Case Report, Minerva Anestesiol, pp. 927-931, vol. 69 No. 12, Dec. 2003.
Caruso, LJ et al, A Better Landmark for Positioning a Central Venous Catheter, J Clinical Monitoring and computing, pp. 331-334, vol. 17 No. 6, Aug. 2002.
Cavatorta, et al., "Central Venous Catheter Placement in Hemodialysis: Evaluation of Electrocardiography Using a Guidewire." The Journal of Vascular Access, vol. 2, pp. 45-50, 2001.

(56) References Cited

OTHER PUBLICATIONS

Chalkiadis, GA et al, Depth of Central Venous Catheter Insertion in Adults: An Audit and Assessment of a Technique to Improve Tip Position, Anaesth Intensive Care, pp. 61-66, vol. 26 No. 1, Feb. 1998.
Chamsi-Pasha, Hassan et al, Cardiac Complications of Total Parenteral Nutrition: The Role of Two-Dimensional Echocardiography in Diagnosis, Annals of the Royal College of Surgeons of England, pp. 120-123, vol. 71, 1989.
Chang, Thomas C. et al., Are Routine Ch Ladiographs Necessary Alter Image-Guided Placement of Internal Jugular Central Venous Access Devices?, AJR Feb. 1998;170:335-337.
Chaturvedi et al., "Catheter Malplacement During Central Venous Cannulation Through Arm Veins in Pediatric Patients." Journal of Neurosurgical Anesthesiology, vol. 15, No. 3 pp. 170-175, Jan. 2003.
U.S. Appl. No. 12/854,083, filed Aug. 10, 2010 Advisory Action dated Sep. 8, 2014.
U.S. Appl. No. 12/854,083, filed Aug. 10, 2010 Final Office Action dated Aug. 15, 2013.
U.S. Appl. No. 12/854,083, filed Aug. 10, 2010 Final Office Action dated Aug. 21, 2015.
U.S. Appl. No. 12/854,083, filed Aug. 10, 2010 Final Office Action dated Jul. 1, 2014.
U.S. Appl. No. 12/854,083, filed Aug. 10, 2010 Non-Final Office Action dated Feb. 1, 2016.
U.S. Appl. No. 12/854,083, filed Aug. 10, 2010 Non-Final Office Action dated Jan. 29, 2013.
U.S. Appl. No. 12/854,083, filed Aug. 10, 2010 Non-Final Office Action dated Jan. 29, 2014.
U.S. Appl. No. 12/854,083, filed Aug. 10, 2010 Non-Final Office Action dated Mar. 16, 2015.
U.S. Appl. No. 12/878,915, filed Sep. 9, 2010 Final Office Action dated Sep. 26, 2012.
U.S. Appl. No. 12/878,915, filed Sep. 9, 2010 Non-Final Office Action dated Mar. 15, 2012.
U.S. Appl. No. 12/878,915, filed Sep. 9, 2010 Notice of Allowance dated Jan. 8, 2013.
U.S. Appl. No. 12/893,916, filed Sep. 29, 2010 Advisory Action dated Aug. 15, 2014.
U.S. Appl. No. 12/893,916, filed Sep. 29, 2010 Advisory Action dated Jun. 2, 2016.
U.S. Appl. No. 12/893,916, filed Sep. 29, 2010 Final Office Action dated Jan. 15, 2015.
U.S. Appl. No. 12/893,916, filed Sep. 29, 2010 Final Office Action dated Jun. 18, 2014.
U.S. Appl. No. 12/893,916, filed Sep. 29, 2010 Final Office Action dated Mar. 25, 2016.
U.S. Appl. No. 12/893,916, filed Sep. 29, 2010 Non-Final Office Action dated Aug. 31, 2016.
U.S. Appl. No. 12/893,916, filed Sep. 29, 2010 Non-Final Office Action dated Dec. 24, 2013.
U.S. Appl. No. 12/893,916, filed Sep. 29, 2010 Non-Final Office Action dated Sep. 10, 2015.
U.S. Appl. No. 12/893,916, filed Sep. 29, 2010 Non-Final Office Action dated Sep. 25, 2014.
U.S. Appl. No. 12/900,750, filed Oct. 8, 2010 Non-Final Office Action dated Jun. 3, 2013.
U.S. Appl. No. 13/019,939, filed Feb. 2, 2011 Final Office Action dated Apr. 2, 2014.
U.S. Appl. No. 13/019,939, filed Feb. 2, 2011 Non-Final Office Action dated Feb. 9, 2015.
U.S. Appl. No. 13/019,939, filed Feb. 2, 2011 Non-Final Office Action dated Oct. 11, 2013.
U.S. Appl. No. 13/118,033, filed May 27, 2011 Final Office Action dated Apr. 1, 2016.
U.S. Appl. No. 13/118,033, filed May 27, 2011 Non-Final Office Action dated Aug. 1, 2013.
U.S. Appl. No. 13/118,033, filed May 27, 2011 Non-Final Office Action dated Feb. 3, 2015.
U.S. Appl. No. 13/118,033, filed May 27, 2011 Non-Final Office Action dated Jul. 8, 2015.
U.S. Appl. No. 13/118,033, filed May 27, 2011 Non-Final Office Action dated May 22, 2014.
U.S. Appl. No. 13/118,033, filed May 27, 2011 Notice of Allowance dated Sep. 2, 2016.
U.S. Appl. No. 13/118,138, filed May 27, 2011 Final Office Action dated Apr. 1, 2016.
U.S. Appl. No. 13/118,138, filed May 27, 2011 Final Office Action dated Apr. 3, 2013.
U.S. Appl. No. 13/118,138, filed MAy 27, 2011 Non-Final Office Action dated Jul. 15, 2015.
U.S. Appl. No. 13/118,138, filed May 27, 2011 Non-Final Office Action dated Oct. 3, 2012.
U.S. Appl. No. 13/118,138, filed May 27, 2011 Non-Final Office Action dated Oct. 9, 2014.
U.S. Appl. No. 13/213,622, filed Aug. 19, 2011 Final Office Action dated Feb. 19, 2013.
U.S. Appl. No. 13/213,622, filed Aug. 19, 2011 Non-Final Office Action dated Jul. 31, 2012.
U.S. Appl. No. 13/213,622, filed Aug. 19, 2011 Non-Final Office Action dated May 22, 2014.
U.S. Appl. No. 13/240,171, filed Sep. 22, 2011 Advisory Action dated Aug. 18, 2015.
U.S. Appl. No. 13/240,171, filed Sep. 22, 2011 Advisory Action dated Jul. 22, 2016.
U.S. Appl. No. 13/240,171, filed Sep. 22, 2011 Final Office Action dated Jun. 10, 2015.
U.S. Appl. No. 13/240,171, filed Sep. 22, 2011 Final Office Action dated May 6, 2016.
U.S. Appl. No. 13/240,171, filed Sep. 22, 2011 Non-Final Office Action dated Dec. 1, 2015.
U.S. Appl. No. 13/240,171, filed Sep. 22, 2011 Non-Final Office Action dated Dec. 26, 2014.
U.S. Appl. No. 13/283,395, filed Oct. 27, 2011 Advisory Action dated Jan. 28, 2014.
U.S. Appl. No. 13/283,395, filed Oct. 27, 2011 Final Office Action dated Nov. 14, 2013.
U.S. Appl. No. 13/283,395, filed Oct. 27, 2011 Non-Final Office Action dated Apr. 23, 2013.
U.S. Appl. No. 13/336,919, filed Dec. 23, 2011 Advisory Action dated May 23, 2013.
U.S. Appl. No. 13/336,919, filed Dec. 23, 2011 Final Office Action dated Dec. 19, 2014.
U.S. Appl. No. 13/336,919, filed Dec. 23, 2011 Final Office Action dated Mar. 1, 2013.
CN 201180068309.9 filed Aug. 22, 2013 Second Office Action dated May 6, 2015.
CN 201180068309.9 filed Aug. 22, 2013 Third Office Action dated Sep. 2, 2015.
CN 201280033189.3 filed Jan. 3, 2014 First Office Action dated Apr. 3, 2014.
CN 201280033189.3 filed Jan. 3, 2014 Second Office Action dated Sep. 14, 2015.
CN 201380051172.5 filed Mar. 30, 2015 Office Action dated May 2, 2017.
CN 201380065663.5 filed Jun. 15, 2015 Office Action dated Mar. 15, 2017.
CN 201380065663.5 filed Jun. 15, 2015 Office Action dated Oct. 10, 2017.
CN 201410009216.4 filed Jan. 8, 2014 Office Action dated Jun. 15, 2016.
CN 201410009216.4 filed Jan. 8, 2014 Second Office Action dated Sep. 25, 2015.
CN 201510144728.6 filed Apr. 17, 2015 Office Action dated Aug. 29, 2017.
CN 201510144728.6 filed Apr. 17, 2015 Office Action dated Jan. 23, 2017.
CO 15110530 filed May 14, 2015 Office Action dated May 8, 2017.
CO 15110530 filed May 14, 2015 Office Action dated Nov. 25, 2016.

(56) References Cited

OTHER PUBLICATIONS

Colley, Peter S et al, ECG-Guided Placement of Sorenson CVP Catheters via Arm Veins, Anesthesia and Analgesia, pp. 953-956, vol. 63, 1984.
Collier, PE et al, Cardiac Tamponade from Central Venous Catheters, Am J Surg, pp. 212-214, vol. 176 No. 2, Aug. 1998.
ComboWire® Pressure/Flow Guide Wire Ref 9500 Series, Instructions for Use, Apr. 2011.
Corsten, et al., "Central Placement Catheter Placement Using the ECG-Guided Cavafix-Certodyn SD Catheter." Journal of Clinical Anesthesiology, vol. 6, Nov./Dec. 1994.
Cucchiara, Roy et al, Time Required and Success Rate of Percantaneous Right Atrial Catherization: Description of a Technique, Canad. Anaesth. Soc. J., pp. 572-573, vol. 27, No. 6, Nov. 1980.
Cullinane, DC et al, The Futility of Chest Roentgenograms Following Routine Central Venous Line Changes, Am J Surg, pp. 283-285, vol. 176 No. 3, Sep. 1998.
Curet, Myriam J. et al., University and Practice-based Physicians' Input on the Content of a Surgical Curriculum, The American Journal of Surgery® vol. 178 Jul. 1999, 78-84.
David, et al., "Is ECG-Guidance a Helpful Method to Correctly Position a Central Venous Catheter During Prehospital Emergency Care?" ACTA Anaesthesiologic Scandinavica, vol. 49, pp. 1010-1014, 2005.
DELTEC Cath-Finder® Tracking System Operation Manual, 1994.
Egelhof, Petra, Effects of Somatostatin on Portal Blood Flow and Portal Vein Pressure in Patients with Portal Hypertension due to Liver Cirrhosis Invasive Monitoring during TIPSS Procedures, Dissertation submitted to: Technical University of Munich, Faculty of Medicine, May 13, 2002; Date of examination: Feb. 26, 2003.
Engelhardt, W et al, ECG-Controlled Placement of Central Venous Catheters in Patients with Atrial Fibrallation, Anaesthesist, pp. 476-479, vol. 38 No. 9, Sep. 1989 (Abstract only).
EP 08855396.1 filed Jun. 15, 2010 European Search Report dated Jul. 31, 2012.
EP 08855396.1 filed Jun. 15, 2010 Intent to Grant dated Jul. 5, 2013.
EP 09707467.8 supplemental European search report dated Jun. 18, 2013.
EP 09743249.6 filed Oct. 18, 2010 Extended European Search Report dated Jan. 13, 2016.
EP 09743249.6 filed Oct. 18, 2010 Intention to Grant dated Mar. 2, 2017.
EP 09808901.4 filed Aug. 21, 2009 European Search Report dated May 23, 2012.
EP 09808901.4 filed Aug. 21, 2009 Examination Report dated May 10, 2013.
EP 09813632.8 filed Apr. 5, 2011 European Search Report dated Jul. 4, 2012.
EP 09813632.8 filed Apr. 5, 2011 Office Action dated Apr. 30, 2013.
EP 09813632.8 filed Apr. 5, 2011 Summons to Attend Oral Proceedings dated Apr. 16, 2014.
EP 10 808 660.4 filed Feb. 15, 2012 Extended European Search Report dated Mar. 4, 2014.
EP 10786978.6 filed Dec. 19, 2011 Extended European Search Report dated Mar. 7, 2014.
EP 10786978.6 filed Dec. 19, 2011 Office Action dated Aug. 11, 2017.
EP 10821193.9 filed Mar. 27 2012 Partial European Search Report dated Oct. 9, 2015.
EP 11 818 828.3 filed Mar. 18, 2013 Extended European Search Report dated Dec. 10, 2014.
EP 11740309.7 filed Aug. 23, 2012 Extended European Search Report dated Aug. 3, 2015.
EP 11787515.3 filed Dec. 12, 2012 partial European search report dated Jun. 23, 2015.
EP 11787515.3 filed Dec. 12, 2012 partial European search report dated Oct. 27, 2015.
EP 11787527.8 filed Dec. 19 2012 Extended European Search Report dated Oct. 9, 2015.
EP 11787527.8 filed Dec. 19, 2012 partial European search report dated May 26, 2015.
EP 11827551.0 filed Feb. 7, 2013 Extended European Search Report dated Sep. 19, 2017.
EP 11837113.7 filed May 28, 2013 Extended European Search Report dated Apr. 24, 2014.
EP 11850625.2 filed Jul. 22, 2013 Extended European Search Report dated Jun. 21, 2017.
EP 12177438.4 filed Jul. 23, 2012 Communication dated Jan. 13, 2014.
EP 12177438.4 filed Jul. 23, 2012 European Search Report dated Dec. 4, 2012.
EP 12177438.4 filed Jul. 23, 2012 European Search Report dated Jun. 7, 2015.
EP 10786978.6 filed Dec. 19, 2011 Office Action dated Jan. 16, 2019.
EP 11850625.2 filed Jul. 22, 2013 Office Action dated Feb. 25, 2019.
EP 15746326.6 filed Jul. 1, 2016 Office Action dated Jan. 29, 2019.
KR 10-2014-7002789 filed Feb. 3, 2014 Office Action dated Feb. 22, 2019.
U.S. Appl. No. 14/040,205, filed Sep. 27, 2013 Board Decision dated May 1, 2019.
U.S. Appl. No. 14/054,700, filed Oct. 15, 2013 Board Decision dated May 1, 2019.
U.S. Appl. No. 14/054,700, filed Oct. 15, 2013 Notice of Allowance dated Jun. 6, 2019.
U.S. Appl. No. 14/201,300, filed Mar. 7, 2014 Board Decision dated Apr. 12, 2019.
U.S. Appl. No. 14/996,247, filed Jan. 15, 2016 Restriction Requirement dated Mar. 22, 2019.
U.S. Appl. No. 15/284,355, filed Oct. 3, 2016 Notice of Allowance dated Feb. 21, 2019.
U.S. Appl. No. 15/365,698, filed Nov. 30, 2016 Non-Final Office Action dated Apr. 18, 2019.
U.S. Appl. No. 15/585,051, filed May 2, 2017 Examiner's Answer dated May 2, 2019.
CN 201380051172.5 filed Mar. 30, 2015 Office Action dated Jul. 30, 2018.
CN 201480010988.8 filed Aug. 27, 2015 Office Action dated Aug. 17, 2018.
CN 201580007645.0 filed Aug. 8, 2016 Office Action dated Sep. 12, 2018.
CN 201610127217.8 filed Mar. 7, 2016 Office Action dated Jun. 11, 2018.
CN 201610127217.8 filed Mar. 7, 2016 Office Action dated Nov. 19, 2018.
Enrique Company-Bosch, "ECG Front-End Design is Simplified with MicroConverter." Analog Dialogue 37-11, (dated Nov. 2003).
EP 11850625.2 filed Jul. 22, 2013 Office Action dated Sep. 24, 2018.
EP 14197137.4 filed Dec. 10, 2014, Office Action dated Nov. 21, 2018.
EP14197136.6 filed Dec. 10, 2014 Office Action dated Nov. 21, 2018.
Hamza, N. et al. "Interference reduction in ECG signal acquisition: Ground electrode removal." 2013 International Conference on Computer Medical Applications (ICCMA), Jan. 2013.
Honeywell, "1, 2 and 3 Axis Magnetic Sensors HMC1051/HMC1052L/HMC1053" dated Jan. 2010.
JP 2013-530322 filed Mar. 18, 2013, Office Action dated Jul. 6, 2018.
KR 10-2014-7002789 filed Feb. 3, 2014 Office Action dated Jun. 21, 2018.
RU 2015110633 filed Mar. 26, 2015 Office Action dated Oct. 25, 2018.
Thakor, N. V., et al. "Ground-Free ECG Recording with Two Electrodes." IEEE Transactions on Biomedical Engineering, vol. BME-27, No. 12, Dec. 1980.
U.S. Appl. No. 14/141,046, filed Dec. 26, 2013 Examiner's Answer dated Oct. 15, 2018.
U.S. Appl. No. 14/788,305, filed Jun. 30, 2015 Advisory Action dated Oct. 19, 2018.
U.S. Appl. No. 14/788,305, filed Jun. 30, 2015 Final Office Action dated Jul. 27, 2018.

(56) References Cited

OTHER PUBLICATIONS

U.S. Appl. No. 14/788,305, filed Jun. 30, 2015 Notice of Allowance dated Nov. 15, 2018.
U.S. Appl. No. 15/192,561, filed Jun. 24, 2016 Final Office Action dated Nov. 1, 2018.
U.S. Appl. No. 15/266,977, filed Sep. 15, 2016 Non-Final Office Action dated Oct. 30, 2018.
U.S. Appl. No. 15/284,355, filed Oct. 3, 2016 Advisory Action dated Aug. 13, 2018.
U.S. Appl. No. 15/365,698, filed Nov. 30, 2016 Final Office Action dated Jul. 12, 2018.
U.S. Appl. No. 15/365,752, filed Nov. 30, 2016 Final Office Action dated Jul. 12, 2018.
U.S. Appl. No. 15/365,752, filed Nov. 30, 2016 Notice of Allowance dated Nov. 6, 2018.
U.S. Appl. No. 15/365,872, filed Nov. 30, 2016 Non-Final Office Action dated Aug. 27, 2018.
U.S. Appl. No. 15/365,872, filed Nov. 30, 2016 Notice of Allowance dated Dec. 21, 2018.
U.S. Appl. No. 15/900,623, filed Feb. 20, 2018 Final Office Action dated Sep. 20, 2018.
EP 11827551.0 filed Feb. 7, 2013 Office Action dated Mar. 13, 2020.
EP 20154593.6 filed Jan. 30, 2020 Extended European Search Report dated Jun. 2, 2020.
U.S. Appl. No. 14/201,300, filed Mar. 7, 2014 Notice of Allowance dated May 8, 2020.
U.S. Appl. No. 15/418,475, filed Jan. 27, 2017 Advisory Action dated May 28, 2020.
U.S. Appl. No. 15/585,051, filed May 2, 2017 Board Decision dated Apr. 21, 2020.
U.S. Appl. No. 15/585,051, filed May 2, 2017 Notice of Allowance dated Jul. 31, 2020.
U.S. Appl. No. 15/625,842, filed Jun. 16, 2017 Non-Final Office Action dated Mar. 18, 2020.
U.S. Appl. No. 15/816,932, filed Nov. 17, 2017 Advisory Action dated Jun. 18, 2020.
U.S. Appl. No. 15/900,623, filed Feb. 20, 2018 Advisory Action dated Aug. 7, 2020.
U.S. Appl. No. 15/900,623, filed Feb. 20, 2018 Final Office Action dated Jun. 12, 2020.
U.S. Appl. No. 16/017,695, filed Jun. 25, 2018 Non-Final Office Action dated Jul. 20, 2020.

* cited by examiner

SYSTEMS AND METHODS FOR GUIDANCE AND PLACEMENT OF AN INTRAVASCULAR DEVICE

CROSS-REFERENCE TO RELATED APPLICATIONS

This application is a continuation of U.S. patent application Ser. No. 14/615,932, filed Feb. 6, 2015, now U.S. Pat. No. 9,839,372, which claims the benefit of U.S. Provisional Patent Application No. 61/936,825, filed Feb. 6, 2014, and titled "SYSTEMS AND METHODS FOR GUIDANCE AND PLACEMENT OF AN INTRAVASCULAR DEVICE," each of which is incorporated herein by reference in its entirety.

BRIEF SUMMARY

Briefly summarized, embodiments of the present invention are directed to a guidance and placement system for assisting a clinician in the placement of a catheter or other medical device within the vasculature of a patient, and related methods. The guidance and placement system enables a distal tip of a catheter to be placed within the patient vasculature in desired proximity to the patient's heart using ECG signals produced by the heart.

In one embodiment, a method for guiding a medical device to a desired location within a vasculature of a patient is disclosed. The method comprises detecting an intravascular ECG signal of the patient and identifying a P-wave of a waveform of the intravascular ECG signal, wherein the P-wave varies according to proximity of the medical device to the desired location.

The method further comprises determining whether the identified P-wave is elevated, determining a deflection value of the identified P-wave when the identified P-wave is elevated, and reporting information relating to a location of the medical device within the patient's vasculature at least partially according to the determined deflection value of the elevated P-wave.

In one embodiment, the intended destination of the catheter within the patient body is such that the distal tip of the catheter is disposed in the lower $\frac{1}{3}^{rd}$ portion of the superior vena cava ("SVC"). The guidance and placement system analyzes the ECG signals of the patient to determine when the catheter has reached its intended destination within the vasculature, then notifies the clinician via a display, for instance. Thus, the system includes an ECG modality for assisting in medical device placement within the patient.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to a guidance and placement system, also referred to herein as a "placement system" or "system," for assisting a clinician in the placement of a catheter or other medical device within the body of a patient, such as within the vasculature. In one embodiment, the guidance and placement system enables a distal tip of a catheter to be placed within the patient vasculature in desired proximity to the heart using ECG signals produced by the patient's heart. In one embodiment, the medical device includes a catheter and the intended destination of the catheter within the patient body is such that the distal tip of the catheter is disposed in the lower $\frac{1}{3}^{rd}$ portion of the superior vena cava ("SVC"). The guidance and placement system analyzes the ECG signals of the patient to determine when the catheter has reached its intended destination within the vasculature, then notifies the clinician via a display, for instance. Thus, the system includes an ECG modality for assisting in medical device placement within the patient.

In one embodiment, the above-referenced ECG guidance modality of the guidance and placement system is accompanied by an ultrasound ("US") modality to assist with initial insertion of the medical device into the body, and a magnetic element-based tracking, or tip location system ("TLS") modality to track the position and orientation of the medical device as it advances toward its intended destination.

Figure 1:
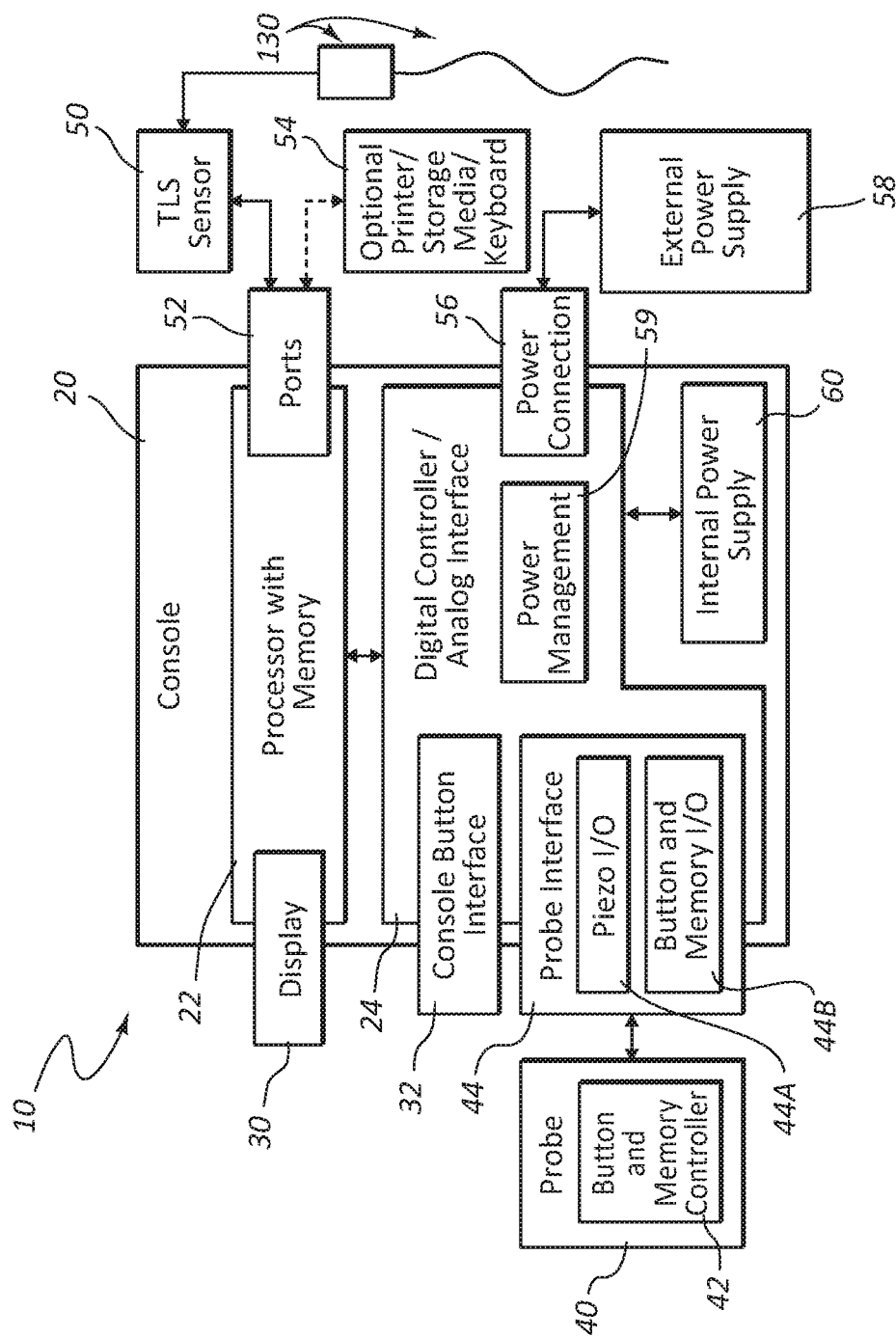
FIG. 1 is a block diagram showing various components of a guidance and placement system according to one embodiment.
Figure 2:
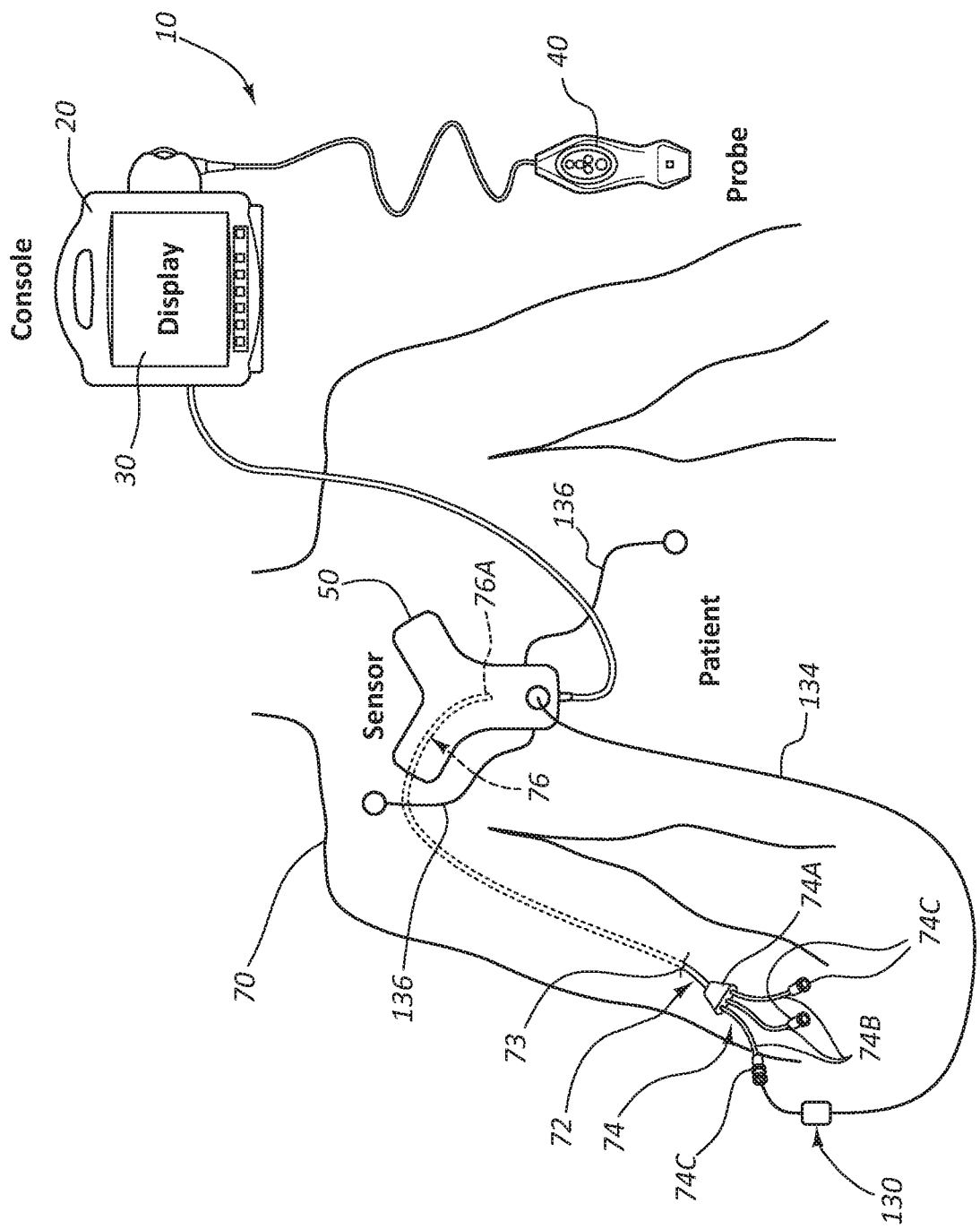
FIG. 2 shows the system of FIG. 1 in use to guide insertion and placement of a catheter into a body of a patient.

Reference is first made to FIGS. 1 and 2 which depict various components of a placement system ("system"), generally designated at 10, configured in accordance with one example embodiment of the present invention. As shown, the system 10 generally includes a console 20, display 30, probe 40, and sensor 50, each of which is described in further detail below.

FIG. 2 shows the general relation of these components to a patient 70 during a procedure to place a catheter 72 into the patient vasculature through a skin insertion site 73. FIG. 2 shows that the catheter 72 generally includes a proximal portion 74 that remains exterior to the patient and a distal portion 76 that resides within the patient vasculature after placement is complete. In the present embodiment, the system 10 is employed to ultimately position a distal tip 76A of the catheter 72 in a desired position within the patient vasculature. In one embodiment, the desired position for the catheter distal tip 76A is proximate the patient's heart, such as in the lower one-third ($1/3^{rd}$) portion of the Superior Vena Cava ("SVC"). Of course, the system 10 can be employed to place the catheter distal tip in other locations. The catheter proximal portion 74 further includes a hub 74A that provides fluid communication between the one or more lumens of the catheter 72 and one or more extension legs 74B extending proximally from the hub.

A processor 22, including non-volatile memory such as EEPROM for instance, is included in the console 20 for controlling system function during operation of the system 10, thus acting as a control processor. A digital controller/analog interface 24 is also included with the console 20 and is in communication with both the processor 22 and other system components to govern interfacing between the probe 40, sensor 50, and other system components.

The system 10 further includes ports 52 for connection with the sensor 50 and optional components 54 including a printer, storage media, keyboard, etc. The ports in one embodiment are USB ports, though other port types or a combination of port types can be used for this and the other interfaces connections described herein. A power connection 56 is included with the console 20 to enable operable connection to an external power supply 58. An internal battery 60 can also be employed, either with or exclusive of an external power supply. Power management circuitry 59 is included with the digital controller/analog interface 24 of the console to regulate power use and distribution.

The display 30 in the present embodiment is integrated into the console 20 and is used to display information to the clinician during the catheter placement procedure. In another embodiment, the display may be separate from the console. As will be seen, the content depicted by the display 30 changes according to which mode the catheter placement system is in: US, TLS, or in other embodiments, ECG tip confirmation. In one embodiment, a console button interface 32 and buttons included on the probe 40 can be used to immediately call up a desired mode to the display 30 by the clinician to assist in the placement procedure. In one embodiment, information from multiple modes, such as TLS and ECG, may be displayed simultaneously. Thus, the single display 30 of the system console 20 can be employed for ultrasound guidance in accessing a patient's vasculature, TLS guidance during catheter advancement through the vasculature, and (as in later embodiments) ECG-based confirmation of catheter distal tip placement with respect to a node of the patient's heart. In one embodiment, the display 30 is an LCD device.

The probe 40 is employed in connection with the first modality mentioned above, i.e., ultrasound ("US")-based visualization of a vessel, such as a vein, in preparation for insertion of the catheter 72 into the vasculature. Such visualization gives real time ultrasound guidance for introducing the catheter into the vasculature of the patient and assists in reducing complications typically associated with such introduction, including inadvertent arterial puncture, hematoma, pneumothorax, etc.

As such, in one embodiment a clinician employs the first, US, modality to determine a suitable insertion site and establish vascular access, such as with a needle and introducer, then with the catheter. The clinician can then seamlessly switch, via button pushes on the probe button pad, to the second, TLS, modality without having to reach out of the sterile field. The TLS mode can then be used to assist in advancement of the catheter 72 through the vasculature toward an intended destination.

FIG. 1 shows that the probe 40 further includes button and memory controller 42 for governing button and probe operation. The button and memory controller 42 can include non-volatile memory, such as EEPROM, in one embodiment. The button and memory controller 42 is in operable communication with a probe interface 44 of the console 20, which includes a piezo input/output component 44A for interfacing with the probe piezoelectric array and a button and memory input/output component 44B for interfacing with the button and memory controller 42.

Note that while a vein is typically depicted on the display 30 during use of the system 10 in the US modality, other body lumens or portions can be imaged in other embodiments. Note that the US mode can be simultaneously depicted on the display 30 with other modes, such as the TLS mode or ECG mode, if desired. In addition to the visual display 30, aural information, such as beeps, tones, etc., or vibratory/motion-based cues can also be employed by the system 10 to assist the clinician during catheter placement. Moreover, the buttons included on the probe 40 and the console button interface 32 can be configured in a variety of ways, including the use of user input controls in addition to buttons, such as slide switches, toggle switches, electronic or touch-sensitive pads, etc. Additionally, US, TLS, and ECG activities can occur simultaneously or exclusively during use of the system 10.

As just described, the handheld ultrasound probe 40 is employed as part of the integrated catheter placement system 10 to enable US visualization of the peripheral vasculature of a patient in preparation for transcutaneous introduction of the catheter. In the present example embodiment, however, the probe is also employed to control functionality of the TLS portion, or second modality, of the system 10 when navigating the catheter toward its desired destination within the vasculature as described below. Again, as the probe 40 is used within the sterile field of the patient, this feature enables TLS functionality to be controlled entirely from within the sterile field. Thus the probe 40 is a dual-purpose device, enabling convenient control of both US and TLS functionality of the system 10 from the sterile field. In one embodiment, the probe can also be employed to control some or all ECG-related functionality, or third modality, of the catheter placement system 10, as described further below.

The catheter placement system 10 further includes the second modality mentioned above, i.e., the magnetically-based catheter TLS, or tip location system. The TLS enables the clinician to quickly locate and confirm the position and/or orientation of the catheter 72, such as a peripherally-inserted central catheter ("PICC"), central venous catheter ("CVC"), or other suitable catheter or medical device, during initial placement into and advancement through the vasculature of the patient 70. Specifically, the TLS modality detects a magnetic field generated by a magnetic element-equipped tip location stylet, which is pre-loaded in one embodiment into a longitudinally defined lumen of the catheter 72, thus enabling the clinician to ascertain the general location and orientation of the catheter tip within the patient body. In one embodiment, the magnetic assembly can be tracked using the teachings of one or more of the following U.S. Pat. Nos. 5,775,322; 5,879,297; 6,129,668; 6,216,028; and 6,263,230. The contents of the afore-mentioned U.S. patents are incorporated herein by reference in their entireties. The TLS also displays the direction in which the catheter tip is pointing, thus further assisting accurate catheter placement. The TLS further assists the clinician in determining when a malposition of the catheter tip has occurred, such as in the case where the tip has deviated from a desired venous path into another vein.

As mentioned, the TLS utilizes a stylet to enable the distal end of the catheter 72 to be tracked during its advancement through the vasculature. In one embodiment, the stylet includes a proximal end and a distal end, with a handle included at the proximal end and a core wire extending distally therefrom. A magnetic assembly is disposed distally of the core wire. The magnetic assembly includes one or more magnetic elements disposed adjacent one another proximate the stylet distal end and encapsulated by tubing. In the present embodiment, a plurality of magnetic elements is included, each element including a solid, cylindrically shaped ferromagnetic stacked end-to-end with the other magnetic elements. An adhesive tip can fill the distal tip of the tubing, distally to the magnetic elements.

Note that in other embodiments, the magnetic elements may vary from the design in not only shape, but also composition, number, size, magnetic type, and position in the stylet distal segment. For example, in one embodiment, the plurality of ferromagnetic magnetic elements is replaced with an electromagnetic assembly, such as an electromagnetic coil, which produces a magnetic field for detection by the sensor. Another example of an assembly usable here can be found in U.S. Pat. No. 5,099,845, entitled "Medical Instrument Location Means," which is incorporated herein by reference in its entirety. Yet other examples of stylets including magnetic elements that can be employed with the TLS modality can be found in U.S. Pat. No. 8,784,336, entitled "Stylet Apparatuses and Methods of Manufacture," which is incorporated herein by reference in its entirety. These and other variations are therefore contemplated by embodiments of the present invention. It should appreciated herein that "stylet" as used herein can include any one of a variety of devices configured for removable placement within a lumen of the catheter to assist in placing a distal end of the catheter in a desired location within the patient's vasculature. In one embodiment, the stylet includes a guidewire.

FIG. 2 shows disposal of a stylet 130 substantially within a lumen in the catheter 72 such that the proximal portion thereof extends proximally from the catheter lumen, through the hub 74A and out through a selected one of the extension legs 74B. So disposed within a lumen of the catheter, the distal end 100B of the stylet 100 in the present embodiment is substantially co-terminal with the distal catheter end 76A such that detection by the TLS of the stylet distal end correspondingly indicates the location of the catheter distal end. In other embodiments, other positional relationships between the distal ends of the stylet and catheter or medical device are possible.

The TLS sensor 50 is employed by the system 10 during TLS operation to detect the magnetic field produced by the magnetic elements of the stylet 130. As seen in FIG. 2, the TLS sensor 50 is placed on the chest of the patient during catheter insertion. The TLS sensor 50 is positioned on the chest of the patient in a predetermined location, such as through the use of external body landmarks, to enable the magnetic field of the stylet magnetic elements, disposed in the catheter 72 as described above, to be detected during catheter transit through the patient vasculature. Again, as the magnetic elements of the stylet magnetic assembly are co-terminal with the distal end 76A of the catheter 72 in one embodiment (FIG. 2), detection by the TLS sensor 50 of the magnetic field of the magnetic elements provides information to the clinician as to the position and orientation of the catheter distal end during its transit.

In greater detail, the TLS sensor 50 is operably connected to the console 20 of the system 10 via one or more of the ports 52, as shown in FIG. 1. Note that other connection schemes between the TLS sensor and the system console can also be used without limitation. As just described, the magnetic elements are employed in the stylet 130 to enable the position of the catheter distal end 76A (FIG. 2) to be observable relative to the TLS sensor 50 placed on the patient's chest. Detection by the TLS sensor 50 of the stylet magnetic elements is graphically displayed on the display 30 of the console 20 during TLS mode. In this way, a clinician placing the catheter is able to generally determine the location of the catheter distal end 76A within the patient vasculature relative to the TLS sensor 50 and detect when catheter malposition, such as advancement of the catheter along an undesired vein, is occurring.

As discussed above, the system 10 includes additional functionality in the present embodiment wherein determination of the proximity of the catheter distal tip 76A relative to a sino-atrial ("SA") or other electrical impulse-emitting node of the heart of the patient 70 can be determined, thus providing enhanced ability to accurately place the catheter distal tip in a desired location proximate the node. Also referred to herein as "ECG" or "ECG-based tip confirmation," this third modality of the system 10 enables detection of ECG signals from the SA node in order to place the catheter distal tip in a desired location within the patient vasculature. Note that the US, TLS, and ECG modalities are seamlessly combined in the present system 10, but can be employed in concert or individually to assist in catheter placement. In one embodiment, it is understood that the ECG modality as described herein can be included in a stand-alone system without the inclusion of the US and TLS modalities. Thus, the environments in which the embodiments herein are described are understood as merely example environments and are not considered limiting of the present disclosure.

As described, the catheter stylet 130 is removably pre-disposed within the lumen of the catheter 72 being inserted into the patient 70 via the insertion site 73. The stylet 130, in addition to including a magnetic assembly for the magnetically-based TLS modality, includes a sensing component, i.e., an internal, intravascular ECG sensor assembly, proximate its distal end and including a portion that is co-terminal with the distal end of the catheter tip for intravascularly sensing ECG signals produced by the SA node, in the present embodiment when the catheter 72 and accompanying stylet 130 are disposed within the patient vasculature. The intravascular ECG sensor assembly is also referred to herein as an internal or intravascular ECG sensor component.

The stylet 130 includes a tether 134 extending from its proximal end that operably connects to the TLS sensor 50, though other connection schemes to the system 10 are contemplated. As will be described in further detail, the stylet tether 134 permits ECG signals detected by the ECG sensor assembly included on a distal portion of the stylet 130 to be conveyed to the TLS sensor 50 during confirmation of the catheter tip location as part of the ECG signal-based tip confirmation modality.

External reference and ground ECG electrodes 136 attach to the body of the patient 70 in the present embodiment and are operably attached to the TLS sensor 50 to provide an external baseline ECG signal to the system 10 and to enable the system to filter out high level electrical activity unrelated to the electrical activity of the SA node of the heart, thus enabling the ECG-based tip confirmation functionality. As shown, in the present embodiment, one external electrode 136 is placed on the patient skin proximate the upper right shoulder ("right arm" placement) while another external electrode is placed proximate the lower left abdomen ("left leg" placement). This electrode arrangement provides a lead II configuration according to Einthoven's triangle of electrocardiography. Operable attachment of the external electrodes 136 with the sensor 50 enables the ECG signals detected by the external electrodes to be conveyed to the console 20 of the system 10 or to another suitable destination. As such, the external electrodes 136 serve as one example of an external ECG sensor component. Other external sensors for detecting a baseline ECG signal external to the patient body can also be employed in other embodiments. In addition, other electrode locations are also possible.

Together with the external ECG signal received from the external ECG sensor component (i.e., the external ECG electrodes 136 placed on the patient's skin), an internal, intravascular ECG signal sensed by the internal ECG sensor component (i.e., the stylet ECG sensor assembly of the stylet 130), is received by the TLS sensor 50 positioned on the patient's chest (FIG. 10) or other designated component of the system 10. The TLS sensor 50 and/or console processor 22 can process the external and internal ECG signal data to produce one or more electrocardiogram traces, including a series of discrete ECG complexes, on the display 30, as will be described. In the case where the TLS sensor 50 processes the external and internal ECG signal data, a processor is included therein to perform the intended functionality. If the console 20 processes the ECG signal data, the processor 22, controller 24, or other processor can be utilized in the console to process the data.

Thus, as it is advanced through the patient vasculature, the catheter 72 equipped with the stylet 130 as described above can advance under the TLS sensor 50, which is positioned on the chest of the patient as shown in FIG. 10. This enables the TLS sensor 50 to detect the position of the magnetic assembly of the stylet 130 (described further above), which is substantially co-terminal with the distal tip 76A of the catheter as located within the patient's vasculature. The detection by the TLS sensor 50 of the stylet magnetic assembly is depicted on the display 30 during ECG mode.

The display 30 can further depict during ECG mode one or more ECG electrocardiogram traces produced as a result of patient heart's electrical activity as detected by the external and internal ECG sensor components described above. In greater detail, the ECG electrical activity of the SA node, including the P-wave of the trace, is detected by the external and internal sensor components and forwarded to the TLS sensor 50 and console 20. The ECG electrical activity is then processed for depiction on the display 30, as will be described further below.

A clinician placing the catheter can then observe the ECG data, which assists in determining optimum placement of the distal tip 76A of the catheter 72, such as proximate the SA node, for instance. In one embodiment, the console 20 includes the electronic components, such as the processor 22 (FIG. 1), necessary to receive and process the signals detected by the external and internal sensor components. In another embodiment, the TLS sensor 50 can include the necessary electronic components processing the ECG signals.

As already discussed, the display 30 is used to display information to the clinician during the catheter placement procedure. The content of the display 30 changes according to which mode the catheter placement system is in: US, TLS, or ECG. Any of the three modes can be immediately called up to the display 30 by the clinician, and in some cases information from multiple modes, such as TLS and ECG, may be displayed simultaneously. In one embodiment, as before, the mode the system is in may be controlled by the control buttons included on the handheld probe 40, thus eliminating the need for the clinician to reach out of the sterile field (such as touching the button interface 32 of the console 20) to change modes. Thus, in the present embodiment the probe 40 is employed to also control some or all ECG-related functionality of the system 10. Note that the button interface 32 or other input configurations can also be used to control system functionality. Also, in addition to the visual display 30, aural information, such as beeps, tones, etc., can also be employed by the system to assist the clinician during catheter placement.

Note that further details regarding the system 10 can be found in U.S. Pat. No. 8,848,382, issued Sep. 30, 2014, and entitled "Apparatus and Display Methods Relating to Intravascular Placement of a Catheter," which is incorporated herein by reference in its entirety.

Figure 3:
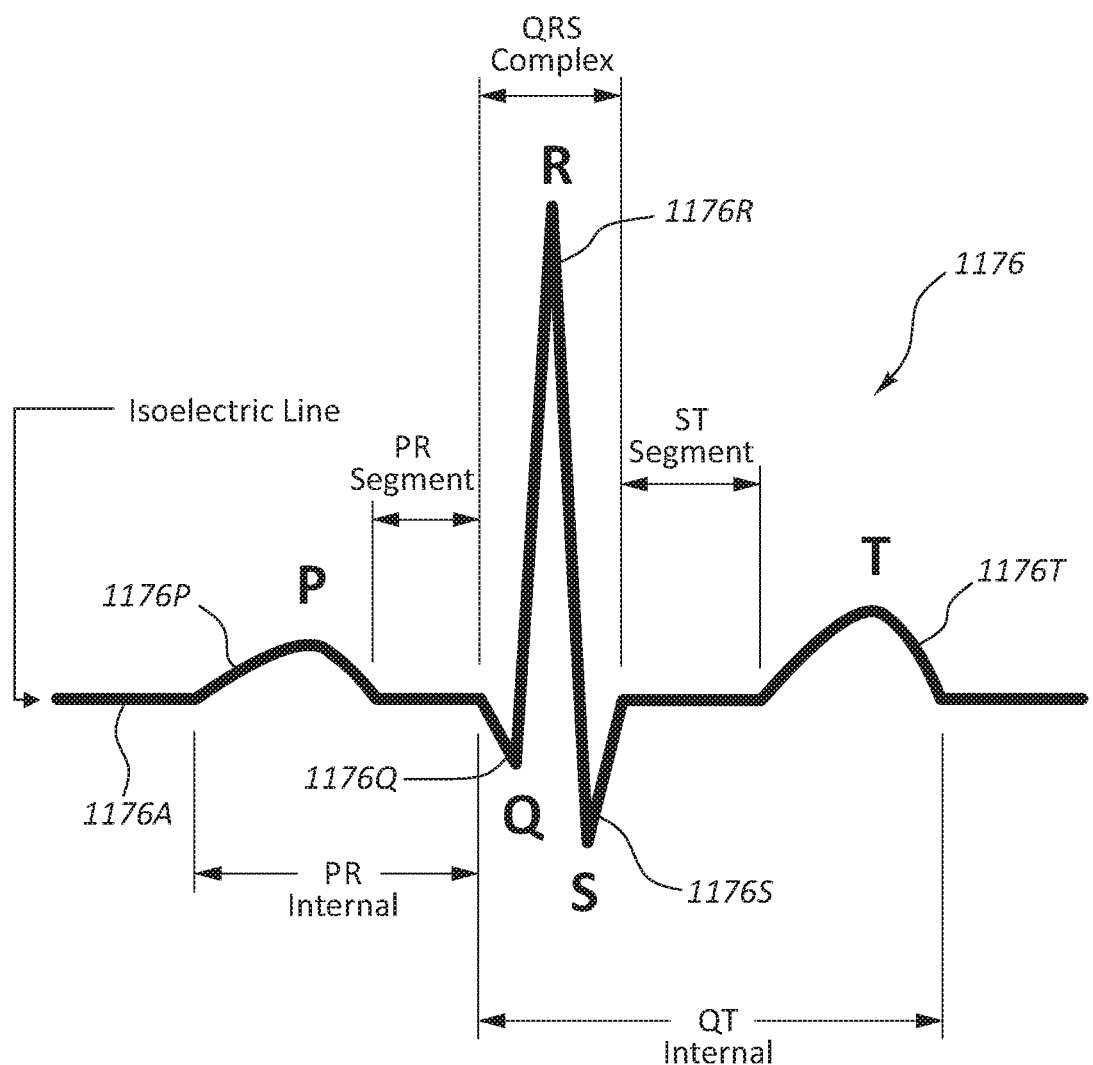
FIG. 3 shows various details of an ECG complex.
Figure 4:
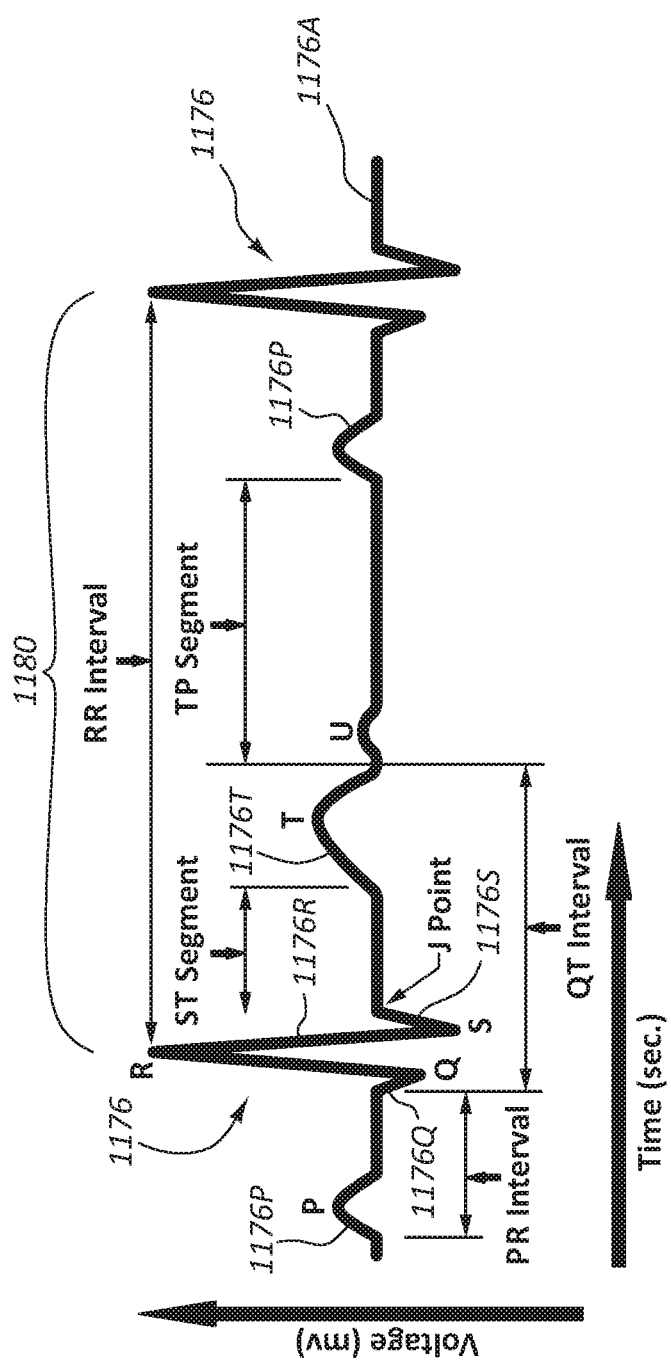
FIG. 4 shows various details of an ECG trace.

FIG. 3 depicts various details of an ECG complex 1176 of an electrocardiogram trace of a patient, including an isoelectric line 1176A, a P-wave 1176P, a Q-wave 1176Q, an R-wave 1176R, and S-wave 1176S, and a T-wave 1176T. FIG. 4 depicts further details and relationships between adjacent ECG complexes 1176, including an RR interval 1180 between successive ECG complexes, which is typically employed to determine the heart rate of the patient. These waves and intervals are used by the system 10 in the present embodiment to determine proximity of the catheter 72 or other medical device to the SA node or other desired location within the patient vasculature, as described herein.

Figure 5:
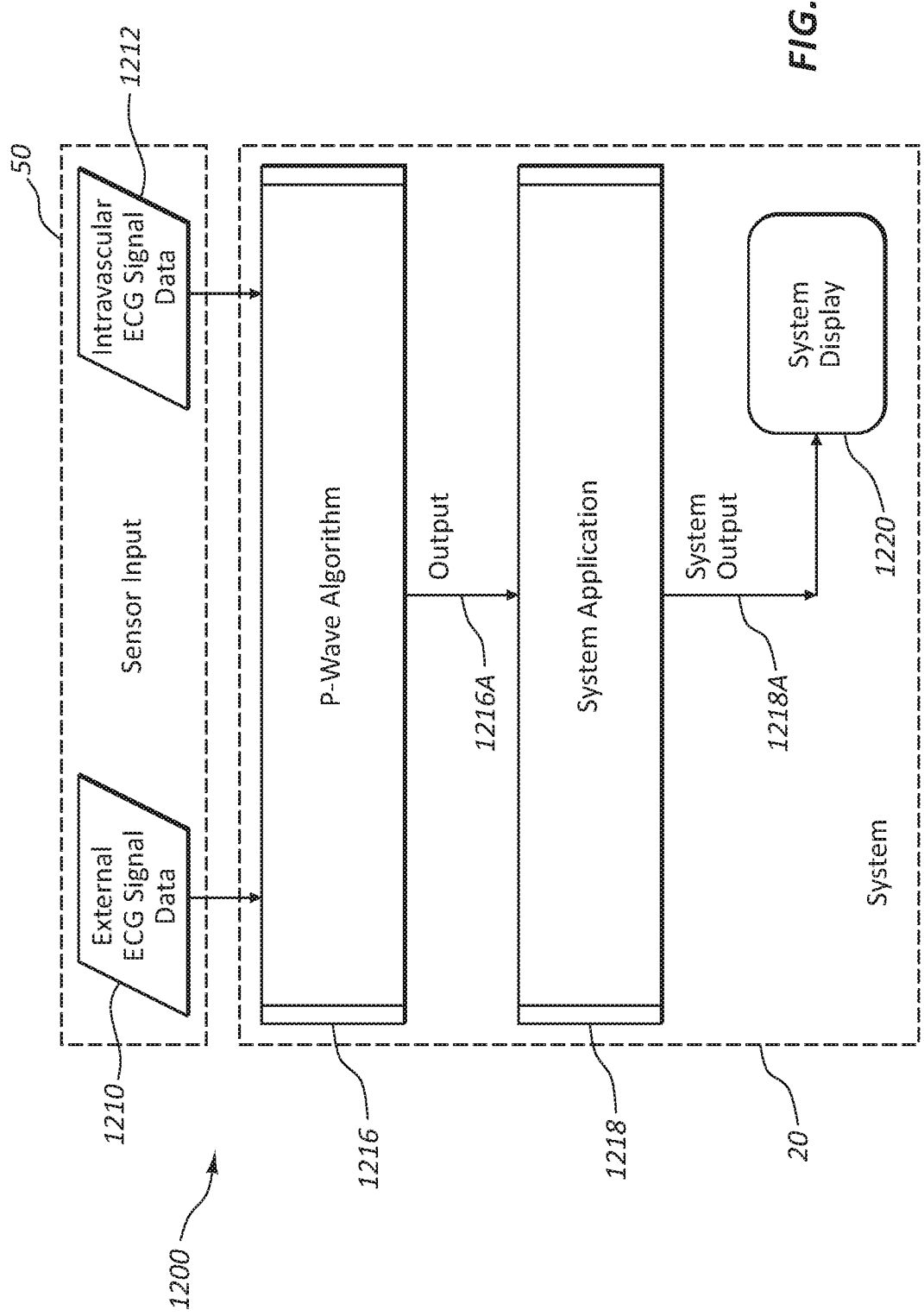
FIG. 5 is a block diagram showing various aspects of a guidance and placement system according to one embodiment.

FIG. 5 depicts an overview of the system 10 and a method 1200 for guiding the catheter to a desired intravascular location. As shown, the method 1200 employs external ECG data 1210 acquired from the external electrodes 136 (also referred to herein as external ECG sensor components) placed externally on the skin of the patient 70, as shown in FIG. 2, though the particular location of the electrodes can vary. As mentioned, the external electrodes 136 in the present embodiment are placed in a right arm/left leg "Lead II" arrangement.

The method 1200 further employs internal, intravascular ECG data 1212 acquired from the above-described internal ECG sensor component, implemented in the present embodiment as the ECG sensor assembly of the stylet 130. The external and intravascular ECG data 1210, 1212 is received and conditioned by processing componentry located in the TLS sensor 50 (FIG. 2) in one embodiment, though other system components can also include this functionality, such as the processor 22 of the system console 20.

Briefly and in accordance with one embodiment, the external and intravascular ECG data 1210, 1212 are input into a P-wave algorithm 1216 in order to determine intravascular proximity of the stylet distal tip to the SA node or other desired location within the patient 70 (FIG. 2). The P-wave algorithm 1216 in one embodiment is executed by a processor included in the TLS sensor 50, or in another embodiment by the processor 22 of the console 20, or by another suitable processor.

Output produced by the P-wave algorithm 1216 includes data relating to analysis of the P-wave of one or more ECG complexes of the intravascular ECG signal and corresponding zone designations relating to the proximity of the distal tip of the stylet 130 of the catheter 72 to the SA node of the heart. The output is received (via arrow 1216A) to a system application executed by the processor 22 of the system console 20, which can then output (via arrow 1218A) graphical information relating to the stylet distal tip position for depiction on a system display 1220, such as the display 30 of the system 10 (FIGS. 1, 2). Observation of the display 30 by the clinician of the information relating to the intravascular position of the stylet distal tip, which in the present embodiment is co-terminal with the distal tip of the catheter 72, aids the clinician in placing the catheter distal tip in the desired location.

Figure 6:
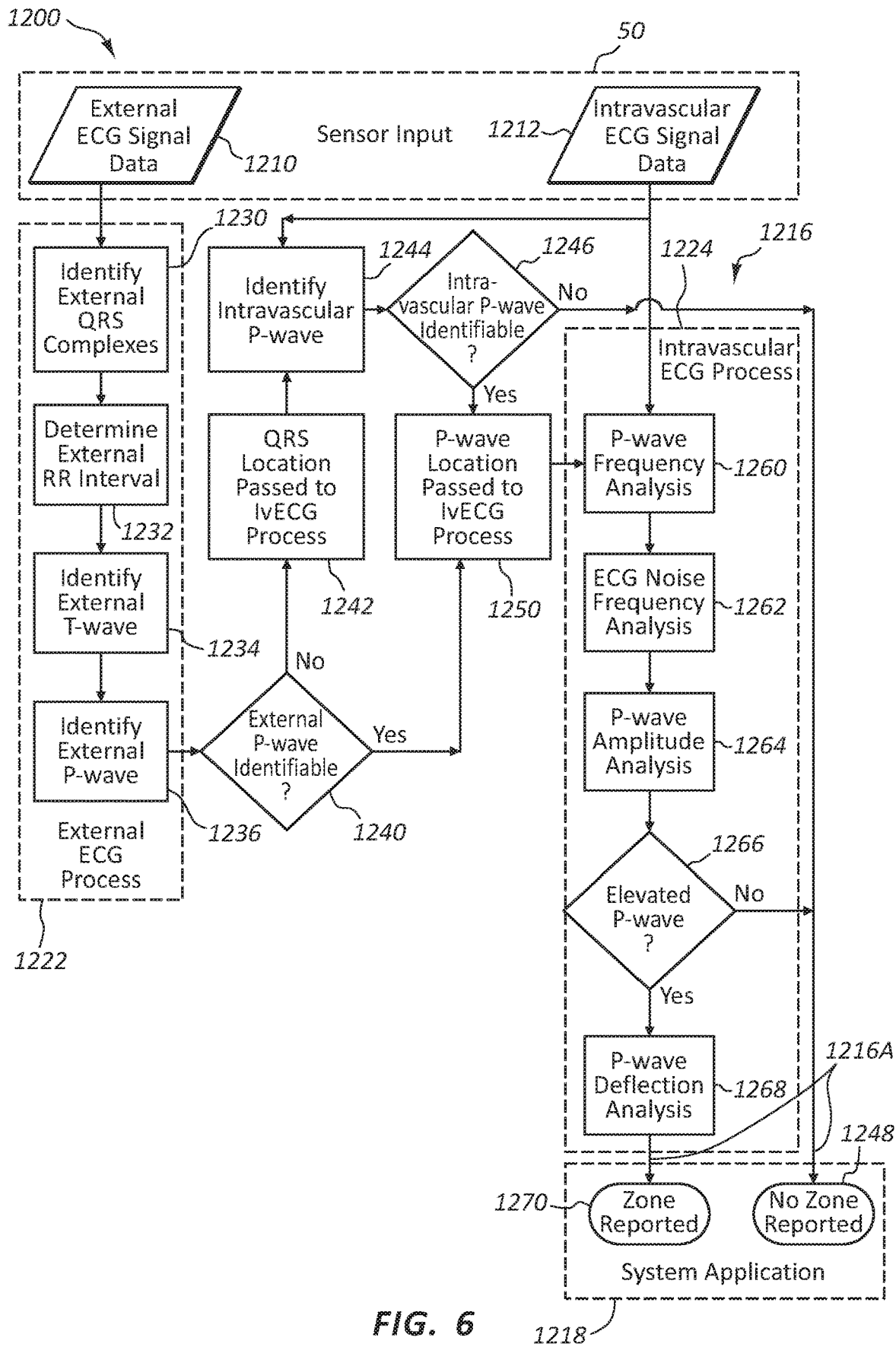
FIG. 6 is a block diagram showing various stages of a method for guiding a medical device according to one embodiment.

FIG. 6 further depicts various details regarding the method 1200 (FIG. 5) for guiding the catheter according to the present embodiment. As shown, the method 1200 includes an external ECG process 1222 utilizing the external ECG data 1210 and an intravascular ECG process 1224 utilizing the intravascular ECG data 1212, with various intermediate actions. Again, in one embodiment the method 1200 is executed by a suitable processor, such as the processor 22 disposed in the system console 22 or a processor disposed in the TLS sensor 50, utilizing external and intravascular ECG signal data detected by the system components, as described above.

The top portion of FIG. 6 shows that the external ECG signal data 1210, including ECG complexes of an external ECG signal detected by the external sensor component (i.e., the skin-placed external electrodes 136), is received by the TLS sensor 50. Likewise, the intravascular ECG signal data 1212, including ECG complexes of an intravascular ECG signal detected by the intravascular sensor component (i.e., the stylet ECG sensor assembly of the stylet 70), is also received by the TLS sensor 50. These data are utilized in the method 1200 as described below.

The external ECG process 1222, which utilizes the external ECG data 1210, is performed first in the present embodiment. Note that the process 1222, as with the other processes to be described herein, can be performed by a suitable processor included in the system 10 or operably associated therewith. As already mentioned, such a processor can include a processor of the TLS sensor 50, the processor 22 of the system console 10, etc.

The external ECG process 1222 includes stage 1230 wherein a QRS complex of a current ECG complex, such as the ECG complex 1176 (FIG. 3), is identified in the ECG signal of the external ECG signal data 1210. In particular, stage 1230 includes determining the location or point in time of occurrence of the QRS complex in the external ECG signal data 1210, which is also referred to herein as time-stamping of the QRS complex within the external ECG signal data 1210. Similar time-stamping can occur for other identified aspects of the ECG complex(es) of succeeding stages. In one embodiment, a $16^{th}$-order finite impulse response ("FIR") filter is employed to identify two successive QRS complexes (waveforms) in stage 1230. Other modes can also be employed to identify this and other waveform components Note that the external ECG signal data 1210 and the intravascular ECG signal data 1212 are time-synchronous such that the occurrence of the QRS complex or other aspect of an ECG complex detected in the external ECG signal data 1210 will correspond in time with the same aspect of the ECG complex detected in the intravascular ECG signal data 1212, in the present embodiment. Thus, the identified aspects of ECG complexes in the external ECG signal data 1210 can be used to find the corresponding aspects in the ECG complexes in the intravascular ECG signal data 1212.

At stage 1232, the time interval for the R-R interval, such as the R-R interval 1180 shown in FIG. 4, between two successive ECG complexes in the external ECG signal data 1210 is determined. This can be used, among other things, for determining patient heart rate.

At stage 1234, the T-wave, such as the T-wave 1176T of FIG. 3, is identified from the current ECG complex of the external ECG signal data 1210 under analysis. Finally, at stage 1236, the P-wave, such as the P-wave 1176P of FIG. 3, is identified from the current ECG complexes of the external ECG data 1210. With such identification, the time of onset (beginning), offset (ending), and maximum amplitude of the identified P-wave are performed at stage 1236 in the present embodiment.

Note that an algorithm to perform one embodiment of stages 1230 to 1236 has been developed as a object library or software library from Monebo Technologies, Inc., 1800 Barton Creek Blvd., Austin, Tex. 78735. In one embodiment, the software library can be accessed via an application program interface ("API") as a callable function. The software library can be accessed by the system application 1218 (FIG. 5). Note also that, in one embodiment, multiple ECG complexes of the external ECG signal data 1210 can be analyzed in performing the above-described stages of the external ECG process 1222.

At stage 1240, a decision is made to confirm that the P-wave has been identified in stage 1236. If not, the method 1200 proceeds to stage 1242, wherein data regarding the QRS location identified at stage 1230 is passed to a new procedure at stage 1244. Indeed, at stage 1244, the P-wave is again identified, but it is identified in the intravascular ECG signal data 1212, using the time-stamped location of the identified QRS complex of the external ECG signal data 1210 from stage 1230. Again note that, because both the external and intravascular ECG data 1210, 1212 are measurements of the electrical activity of the SA node of the patient's heart, they are time-synchronized despite being detected via different apparatus (i.e., the external electrodes 136 for the external ECG signal data, and the stylet sensor assembly of the stylet 130 for the intravascular ECG signal data). Thus, identification of the QRS complex of an ECG complex from the external ECG signal data 1210 will correspond in time/location to a QRS complex or other component of the corresponding ECG complex in the intravascular ECG signal data 1212.

At stage 1246 it is determined whether the intravascular P-wave (identified from the intravascular ECG signal data 1212) has been successfully identified in stage 1244. If the answer is "no," the process forwards a "no report" signal to the system 10 at stage 1248. If the answer at stage 1246 is "yes" as to successful identification of the intravascular P-wave, the time-stamped location of the intravascular P-wave is forwarded at stage 1250 to the intravascular ECG process 1224. Alternatively, if the answer at stage 1240 is "yes" as to successful identification of the external P-wave, the stages 1242, 1244, and 1246 are skipped, as seen in FIG. 6, and the time-stamped external P-wave (identified from the external ECG signal data 1210) is forwarded at stage 1250 to the intravascular ECG process 1224. In one embodiment, time-stamping data regarding various aspects of the P-wave are forwarded, including time of P-wave onset, P-wave peak (or maximum amplitude), and P-wave offset.

Upon receipt of the P-wave location (via identification thereof in the external ECG signal data 1210 at stage 1236 or in the intravascular ECG signal data 1212 at stage 1244) from stage 1250, the intravascular ECG process 1224 begins at stage 1260 by performing a frequency analysis of the P-wave as detected by the internal ECG sensor. In the present embodiment and as executed by the processor 22 (FIG. 1) or other suitable processing component, stage 1260 includes analyzing the P-wave in the frequency domain to determine whether it meets or exceeds a predetermined threshold value. In one embodiment, the frequency of the P-wave can be thought of as the inclined slope of the P-wave in the time domain.

At stage 1264, an amplitude analysis of the P-wave is also performed in the time domain to determine whether it meets or exceeds a predetermined threshold value. In the present embodiment, the P-wave is determined to be at a maximum when its possesses the following threshold values: an amplitude of between about 250 microvolts and about 1500 microvolts at or above about 20 Hz; and a frequency (inclined slope) range between: exceeding about 10 microvolts per millisecond when the P-wave amplitude is at about 250 microvolts and exceeding 60 microvolts per millisecond when the P-wave amplitude is at about 1500 microvolts. Of course, other ranges and values can be used in other embodiments according to application, desired sensitivity, intended target location, etc.

At stage 1262 an analysis is performed to determine whether noise in the intravascular ECG signal data 1212 exceeds acceptable levels such that reliable P-wave determination is impossible. In detail, the process 1224 at stage 1262 reports a value related to the level of noise encountered. In the present embodiment, the threshold noise values include: the maximum level of high frequency (i.e., greater than about 20 Hz) noise present between the offset, or end, of the QRS complex of an ECG complex and onset, or beginning, of the P-wave of the successive ECG complex is less than about 35 microvolts, with a ratio of the maximum level of high frequency noise to the maximum amplitude of the high frequency component of the P-wave in the current ECG complex is less than about 50%. Other noise values can be employed by the process 1224 in determining acceptable noise threshold levels.

Figure 7:
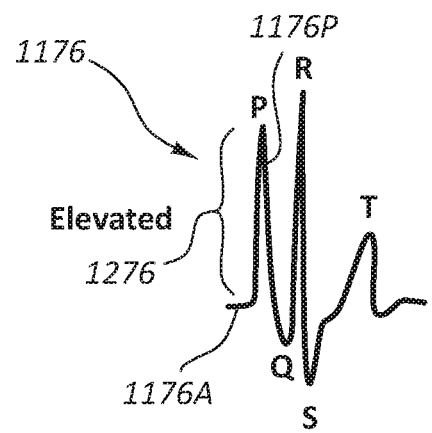
FIG. 7 shows various details of a captured intravascular ECG complex according to one embodiment.

At stage 1266, it is determined whether an elevated, or maximum P-wave in the ECG complex, such as that seen at 1176P in the ECG complex 1176 of FIG. 7, has been identified. This is done by determining whether the above-discussed P-wave frequency, amplitude and noise threshold values (determined in stages 1260, 1264, and 1262, respectively) have each been met. If one or more have not been met, the process forwards a "no report" signal to the system 10 at stage 1248.

Figure 8:
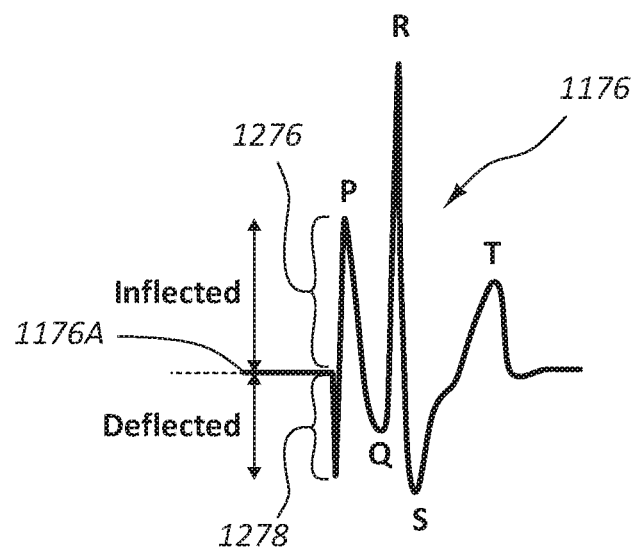
FIG. 8 shows various details of a captured intravascular ECG complex according to one embodiment.

If each of the above threshold values of stages 1260, 1262, and 1264 has been met, stage 1266 reports a "yes" and stage 1268 is executed, wherein a deflection analysis of the P-wave is performed. FIG. 8 shows a P-wave portion of the ECG complex 1176 as including a deflection portion 1278, or negative P-wave component that dips below the isoelectric line 1176A before rising to form the inflected portion 1276—the portion of the P-wave rising above the isoelectric line of the P-wave. Stage 1268 analyzes the P-wave for such a deflection. In the present embodiment, stage 1268 is performed by dividing the amplitude of the deflection portion 1278 of the P-wave by the inflected portion 1276 of the P-wave, which yields a deflection percentage. The value of the deflection percentage enables the system 10 to determine the proximity of the intravascular ECG sensor (implemented as the stylet ECG sensor assembly of the stylet 130 at the stylet distal tip), and hence the catheter distal tip, to the SA node.

Figure 12:
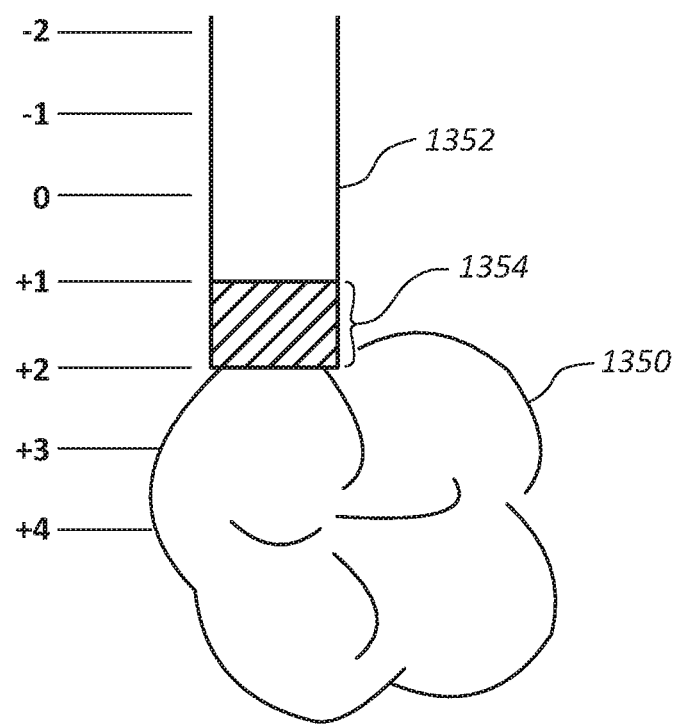
FIG. 12 is a simplified view of a heart with possible reporting zones superimposed thereon, according to one embodiment.

In the present embodiment, a deflection value of about 0% indicates that there is substantially no deflection of the P-wave and that the stylet distal tip is at or near a lower $\frac{1}{3}^{rd}$ portion 1354 of a SVC 1352 near a heart 1350 of the patient vasculature, referred to by the process 1224 as zone 1, shown in FIG. 12. A deflection value of greater than about 0% but less than or equal to about 10% indicates that the P-wave is minimally deflected and that the stylet distal tip has passed but is near the lower $\frac{1}{3}^{rd}$ portion 1354 of the SVC 1352, referred to by the process 1224 as zone 2. A deflection value of greater than about 10% indicates that the P-wave is significantly deflected and that the stylet distal tip is well past the lower $\frac{1}{3}^{rd}$ 1354 portion of the SVC 1352, referred to by the algorithm as zone 3. Note that FIG. 12 illustrates that additional zones can be defined and reported by the process 1224 according to its analysis of the detected P-wave characteristics. Indeed, FIG. 12 shows that a variety of zones can be defined, such as a range extending from −2 to +4, which are equally spaced at varying distances from the lower $\frac{1}{3}^{rd}$ portion 1354 of the SVC 1352. Of course, other zones and spacings can also be defined as part of the method 1200.

The zone assigned by the process 1224 is reported to a system application 1218 of the system 10 at stage 1270. In one embodiment, the system application 1218 includes a controlling firmware or software application as executed by the processor 22 (FIG. 1) or other suitable component of the system 10. Note that in one embodiment the same processor, such as the processor 22 of the system console 20 (FIG. 1), can be employed to execute both the method 1200 and the system application 1218. The above-described three zones, indicating proximity of the catheter distal end to the patient heart 1350 (FIG. 12) can be reported in stage 1270 to the system application 1218. Additional zones can also be defined and reported, in another embodiment. The system application 1218 can then use the reporting of such zones to convey pertinent information to the user of the system 10 to assist the user in placing the catheter at a desired location within the vasculature, as described further below.

The above-described method 1200 is iteratively executed in the present embodiment so as to evaluate successive ECG complexes of the patient as detected by the system 10. In other embodiments, non-iterative operation is possible. Once a sufficient number of zone reports (i.e., reports of the zone in which the stylet distal tip is located with respect to the patient heart) according to the analysis of the P-wave by the method 1200 are received by the system application 1218 of the system 10 (via stages 1270 and/or 1248), the display 30 (FIGS. 1, 2) can be updated to indicate the reported zone, if any, and assist the clinician in determining when the distal tip of the catheter or other suitable medical device has reached the desired intravascular location.

Figure 10A:
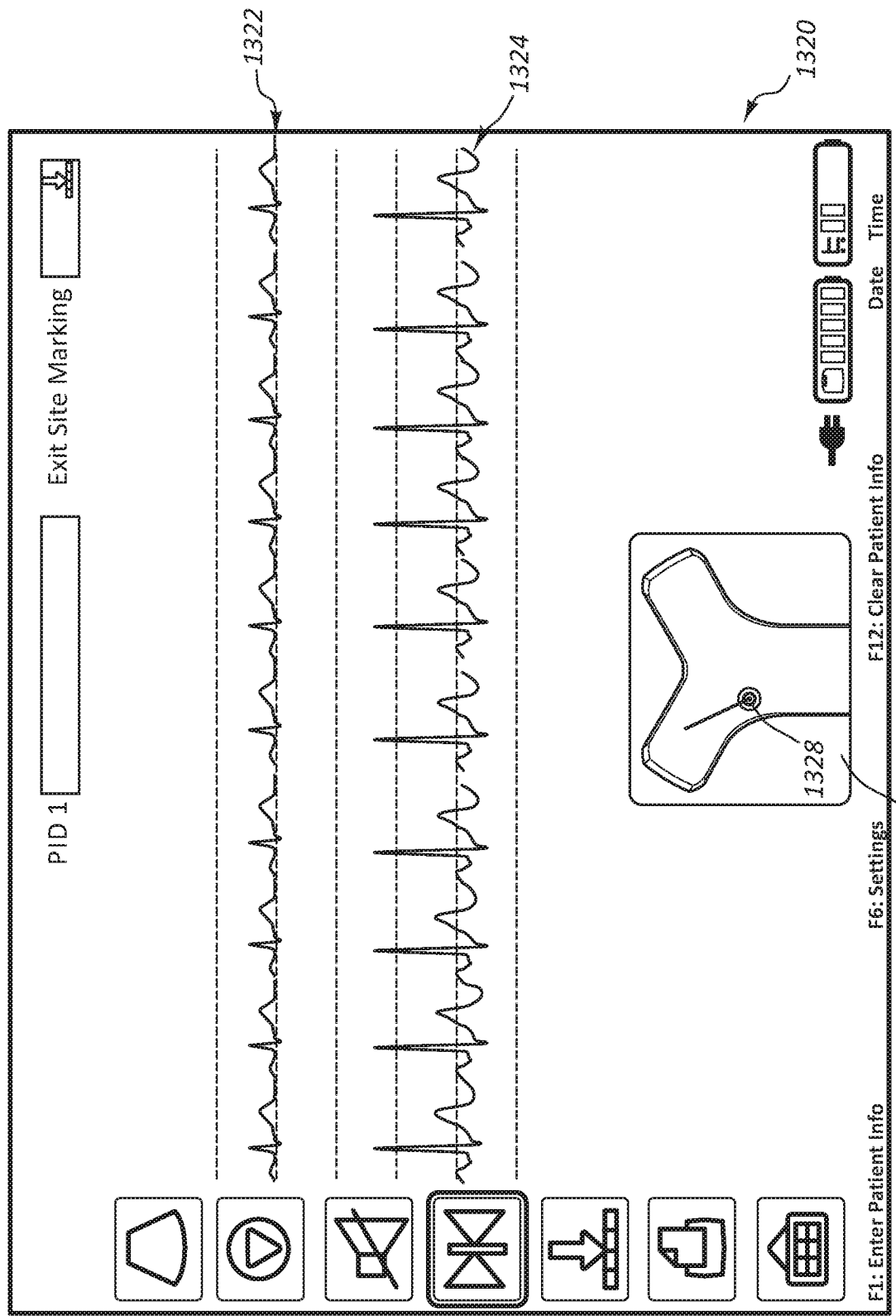
FIGS. 10A-10C show various screenshots of a display of a guidance and placement system according to one embodiment.
Figure 10B:
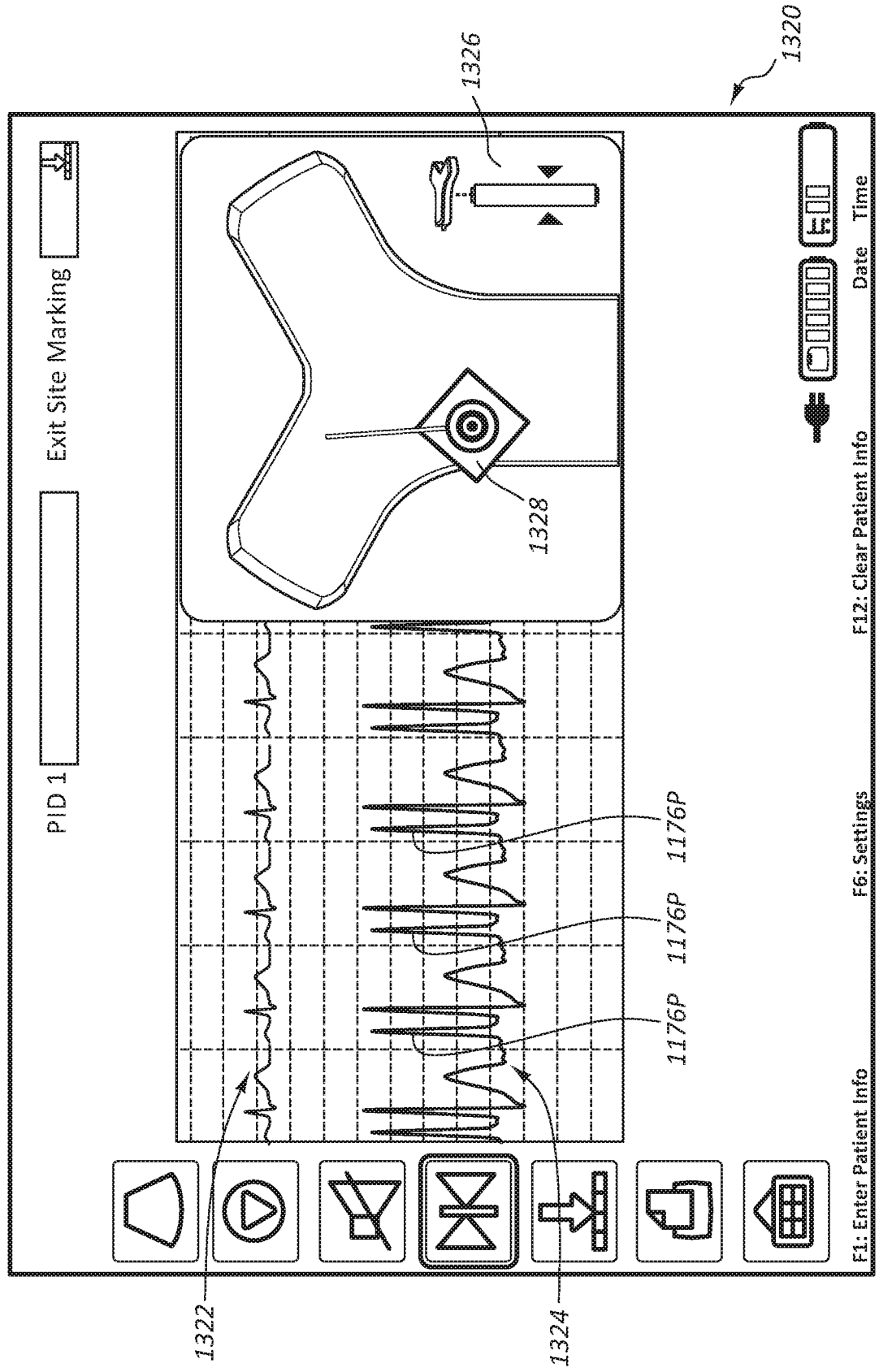
Figure 10C:
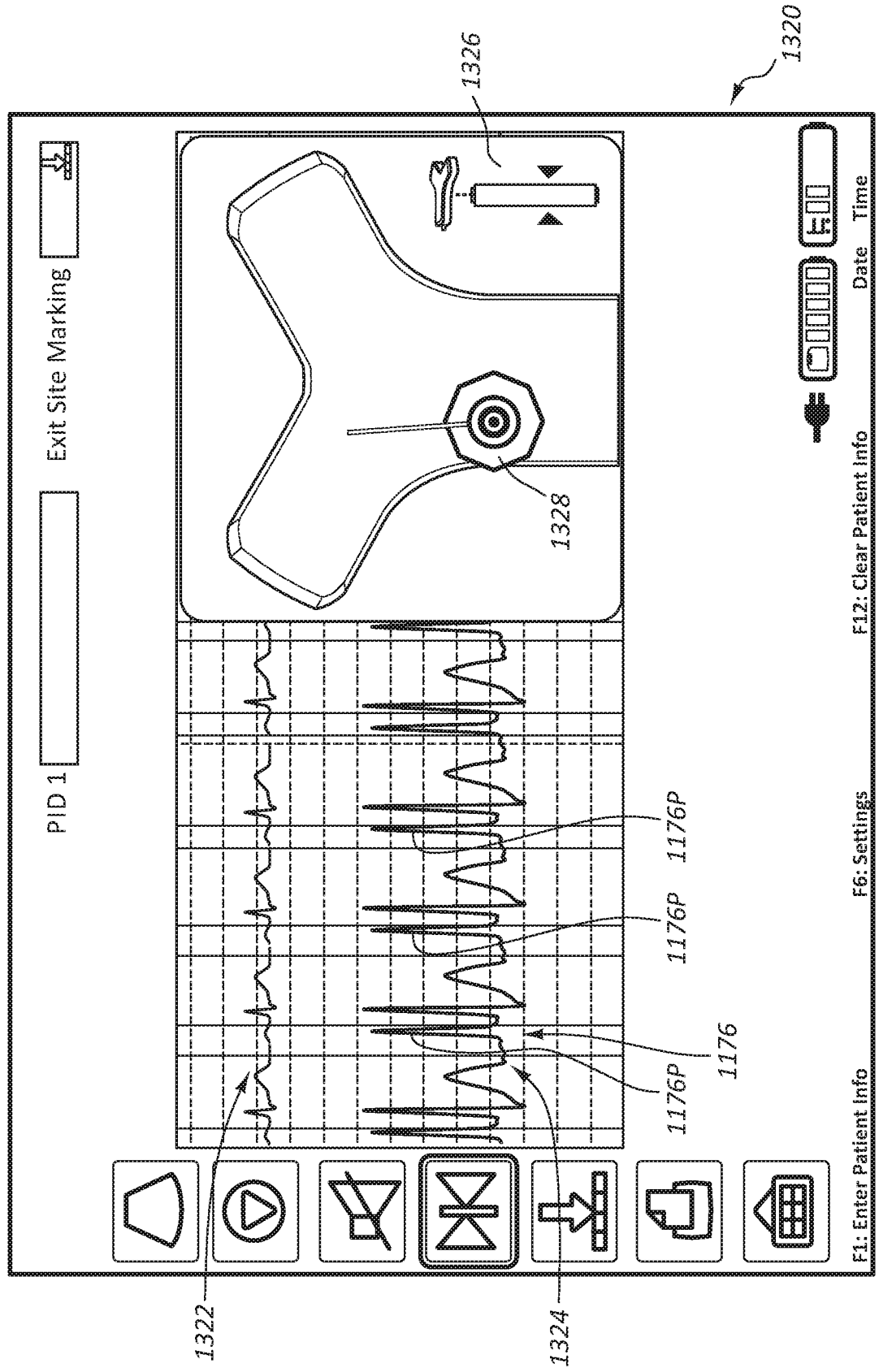

In light of the above, FIGS. 10A-10C show various examples of the depiction of the zone reports provided by the method 1200 of FIG. 6 to the system application 1218, on the display 30 of the system 10 (FIGS. 1, 2). In particular, FIGS. 10A-10C show various depictions, or screenshots 1320 of the display 30 during use of the system 10 to guide and place a catheter within the vasculature of a patient. As shown in FIG. 10A, an external ECG trace 1322 is present, as detected by the external ECG signal sensor component, which in the present embodiment includes the external electrodes 136, as described further above. An intravascular ECG trace 1324 is also depicted, as detected by the intravascular ECG signal sensor component, which in the present embodiment includes the stylet ECG sensor assembly of the stylet 130.

A sensor image 1326 is also shown, which represents the sensor 50 (FIGS. 1, 2) and its detection of the stylet distal tip. A stylet position icon 1328 is shown superimposed on the sensor image 1326 to indicate position of the stylet distal tip via magnet tracking in TLS mode, ECG tracking in the ECG mode just described, or a combination of both. Note that the icon 1328 in FIG. 10A includes a bullseye configuration, indicating that the system while in ECG tracking mode has not yet detected the stylet distal tip as having arrived at zone 1 proximate the lower $\frac{1}{3}^{rd}$ portion 1354 of the SVC 1352 (FIG. 12).

FIG. 10B shows the screenshot 1320 with the sensor image 1326 increased in size, which is an option selectable by the clinician or automatically performed by the system 10, in one embodiment. Note that the stylet position icon 1328 has changed to a diamond, which can be colored green, indicating that the system 10 has determined that the stylet distal tip is located within either zone 1 or 2 (FIG. 12), as reported to the system by the process 1224 (FIG. 6).

In FIG. 10C and according to one embodiment, the P-wave portions of the ECG complexes shown in the external and internal ECG traces 1322, 1324 of the screenshot 1320 are highlighted, such as by color, for clinician convenience. FIG. 10C shows that if the stylet distal tip is advanced beyond the lower $\frac{1}{3}^{rd}$ portion 1354 of the SVC 1352 the process 1224 of the method 1200 would report a zone 3. This, in turn, causes the stylet position icon 1328 to change from a green diamond to a red octagon, indicating that further advancement of the stylet 130 and catheter 72 should stop. Of course, other colors, shapes, designs, and configurations for the stylet position icon can be employed by the system 10. Indeed, further examples of position icons that can be employed are found in U.S. Pat. No. 10,751,509, filed Mar. 7, 2014, and titled "Iconic Representations for Guidance of an Indwelling Medical Device," which is incorporated herein by reference in its entirety.

Figure 9:
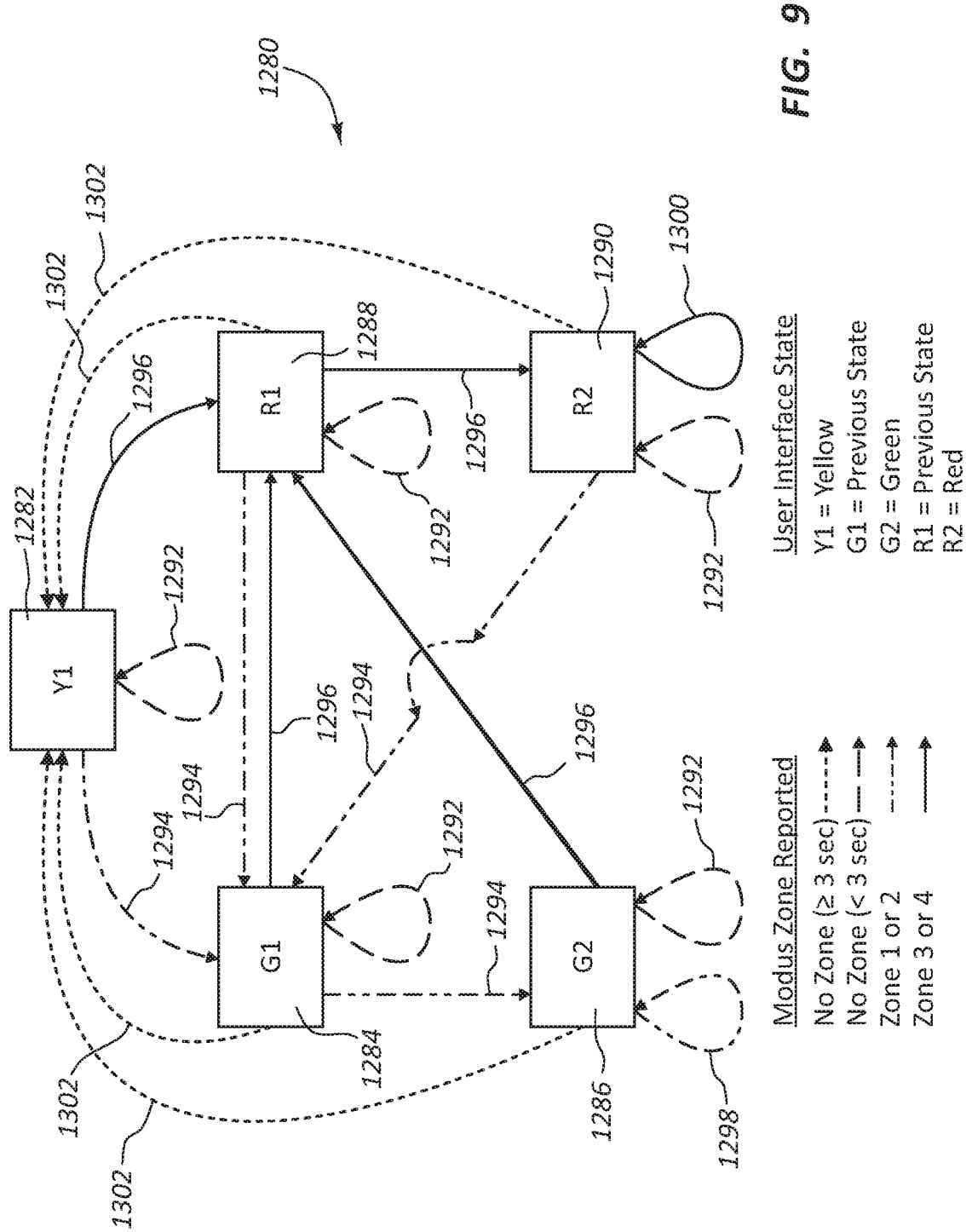
FIG. 9 shows a decision tree for determining display output to a guidance and placement system according to one embodiment.

FIG. 9 shows a zone reporting decision tree 1280 that is employed in the present embodiment by the system application 1218 to determine when changing/updating of the display 30 is warranted so as to accurately reflect the position of the stylet distal tip, and hence the catheter distal tip. During execution of the method 1200 (FIG. 6) while the stylet 130 and catheter 72 are advanced within the patient vasculature, the display 30 will depict the stylet position icon 1328 as a yellow-colored bullseye, such as that seen in FIG. 10 on the sensor image 1326, when no zone has been reported to the system application 1218 by the process 1224. This situation corresponds to block 1282, marked "Y1" to indicate the yellow icon color. Note that in the present embodiment the method 1200 will iteratively report a zone (stage 1270 in FIG. 6) or a no zone (stage 1248) to the system application 1218 during execution of the method and operation of the system 10.

When the process 1224 reports a zone 1 or 2 to the system application 1218 (FIG. 6), advancement from Y1 block 1282 to block 1284, which is marked "G1" to indicate an initial green state, occurs. When the process 1224 iteratively reports a second successive zone 1 or 2, advancement is made from G1 block 1284 to block 1286, which is marked "G2" to indicate a green state. This corresponds to the stylet position icon 1328 being changed from the yellow bullseye icon of FIG. 10A to a green diamond icon as seen in FIG. 10B.

Should the process 1224 then report a zone 3 or greater to the system application 1218, advancement from the G2 block 1286 to block 1288, which is marked "r1" to indicate an initial red state, occurs. If the process 1224 iteratively reports a second successive zone 3 or greater, advancement is made from R1 block 1288 to block 1290, which is marked "R2" to indicate a red state. This corresponds to the stylet position icon 1328 being changed from the green diamond of FIG. 10B to the red octagon as seen in FIG. 10C.

Should the process 1224 then report a zone 1 or 2 to the system application 1218, advancement from the R2 block 1290 back to the G1 block 1284 is made to proceed as described above. This—as well as similar advancement to the G1 block 1284 from the R1 block 1288 or the Y1 block 1282—is indicated by the arrows 1294. Correspondingly, advancement to the R1 block 1288 from blocks 1282, 1284, or 1286 is indicated by the arrows 1296.

On any of the blocks 1282, 1284, 1286, 1288, and 1290, the lack of any reporting from the process 1224 for a period of less than three seconds causes the system application 1218 to remain on the same designated block. This is indicated by the looped arrows 1292 adjacent each of the blocks 1282, 1284, 1286, 1288, and 1290.

On any of the blocks 1282, 1284, 1286, 1288, and 1290, the lack of any reporting from the process 1224 for a period equal to or more than three seconds causes the system application 1218 to revert to the Y1 block 1282, with the corresponding change of the stylet position icon 1328. This is indicated by the dashed arrows 1302 leading to the Y1 block 1282 from the blocks 1284, 1286, 1288, and 1290.

On the G2 block 1286 and the R2 block 1290, continued reporting from the process 1224 of the same zone causes the system application 1218 to remain on the same designated block. This is indicated by the looped arrows 1298 and 1300 for the G2 block 1286 and the R2 block 1290, respectively.

Figure 13:
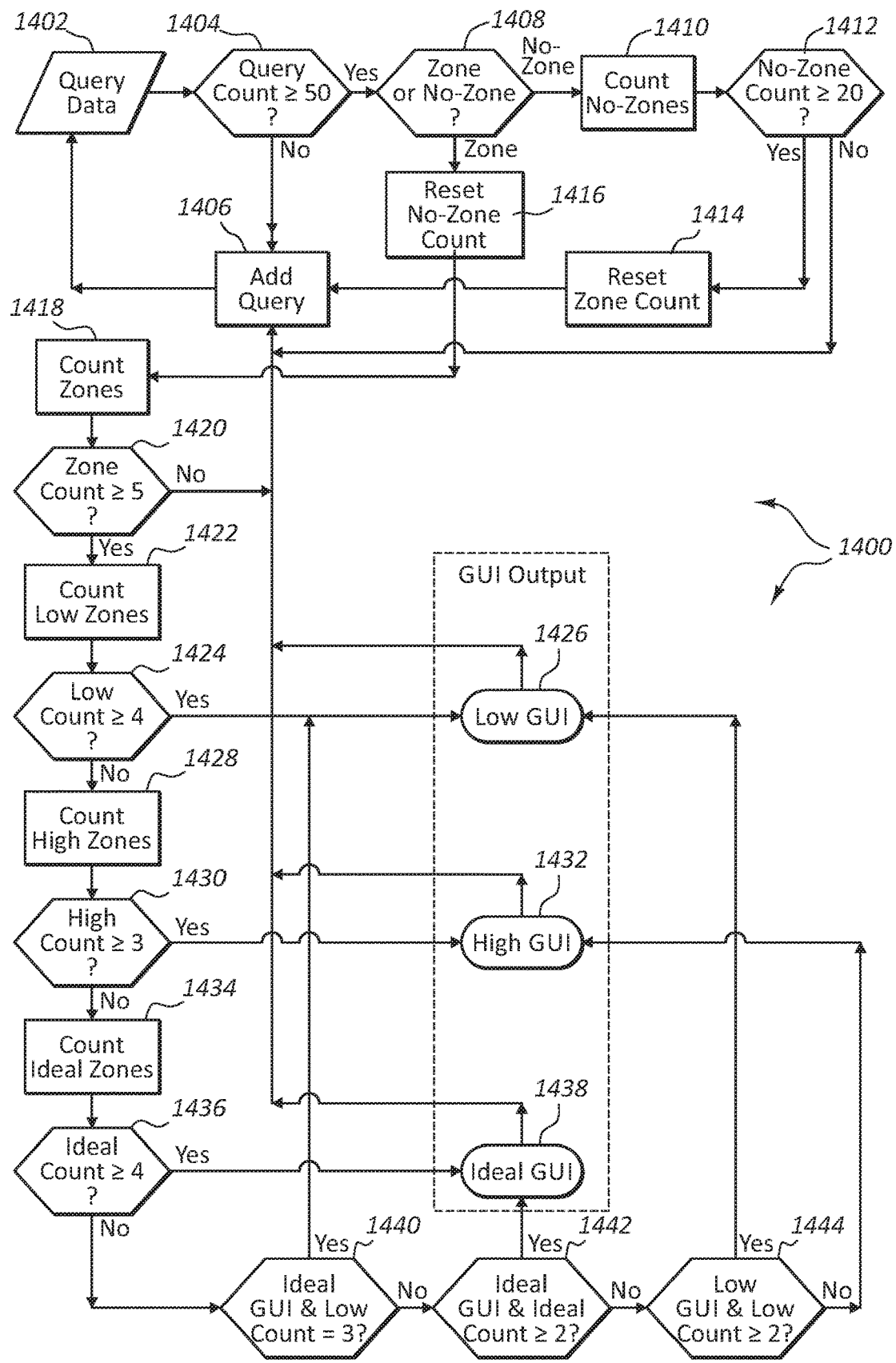
FIG. 13 shows a decision tree for determining display output to a guidance and placement system according to one embodiment.

FIG. 13 shows a zone reporting decision tree 1400 that is employed in one embodiment by the system application 1218 to determine when changing/updating of the display 30 is warranted so as to accurately reflect the position of the stylet distal tip, and hence the catheter distal tip, during catheter insertion and positioning. In particular, the method 1400 is executed in one embodiment by the system application 1218 in deciding how and when to update the depiction on the display 30, including the stylet position icon 1328 (see FIGS. 10A-10C), based on the zone reports 1248, 1270 of the P-wave output 1216A of the process 1224.

Method 1400 begins at stage 1402 by querying the zone report data (also referred to as a "data set") provided to the system application 1218 by the process 1224 via P-wave output 1216A. Each zone report in the zone report data includes either a no-zone indication or one of three zone indications: low, high, and ideal, as described further below. In stage 1404 it is determined whether the query count, or number of zone reports provided to the system application 1218, is equal to or greater than 50. If not, stage 1406 is executed, which adds another query, or zone report, at stage 1402.

If the query count at stage 1404 yields 50 or more in quantity, stage 1408 is executed, wherein the latest zone report is examined to determine whether it reports a zone (corresponding to a "zone reported" at stage 1270 in FIG. 6) or if it reports a "no-zone" (corresponding to a "no zone reported" at stage 1248 in FIG. 6). If the latest zone report is a no-zone, stage 1410 is executed, wherein a no-zone counter is increased by one and the number of consecutive no-zones is counted. Then, at stage 1412, it is determined whether the number of counted consecutive no-zones is equal to or greater than 20. If not, then stage 1406 is executed, which adds another query, or zone report, to stage 1402. If the answer at stage 1412 is "yes," a zone counter is reset to zero at stage 1414, a high state is declared at stage 1432, in which the system application 1218 will depict an appropriate indication on the display 30 (FIG. 2), for instance, indicating to the user that the catheter can be advanced further and has not yet arrived at the desired destination, in this case, the lower $1/3^{rd}$ portion 1354 of the SVC 1352. In one embodiment, the depiction on the display 30 includes the yellow bullseye design of the stylet position icon 1328 as seen in FIG. 10A. Once the depiction is displayed, the method 1400 reverts to stage 1406 then stage 1402, wherein zone report data are queried anew. In one embodiment, previously stored query data are disposed and new data are acquired. The above-described process is iterative with respect to the no-zone reporting.

Note that in the present embodiment, the query count of 50 in stage 1404 corresponds to approximately five seconds of data as captured by the system 10 and the method 1200 (FIG. 6), that is, 500 hertz date rate received by the TLS sensor 50 processed in blocks of 50, yielding 10 zone determinations per second. The buffer used to store the data of stage 1402 operates on a first-in, first-out ("FIFO") basis, ejecting the oldest value in the buffer as a new value is received.

If, at stage 1408 the latest zone report reports a zone, stage 1416 is executed, wherein the no-zone counter is reset to zero and control advances to stage 1418. At stage 1418, the data is analyzed, beginning with the most recent zone reports, and at stake stage 1420, it is determined whether at least five zone reports are present in the queried zone report data from stage 1402 (the at least five zone reports need not be consecutive in the data). If not, the method reverts to stage 1406, wherein another query is added to stage 1402 and the method proceeds from there.

If the answer at stage 1420 is "yes," stage 1422 is executed, wherein the at least five zone reports are analyzed and at stage 1424, it is determined whether four or more of the zone reports are "low" zone reports, indicating that the distal tip of the stylet 130 has passed the lower $1/3^{rd}$ portion 1354 of the SVC 1352 (as in zones +3, +4 of FIG. 12). If yes, a low state is declared at stage 1426, in which the system application 1218 will depict an appropriate indication on the display 30 (FIG. 2), for instance, indicating to the user that the catheter has been advanced too far. In one embodiment, the depiction on the display 30 includes the red octagon design of the stylet position icon 1328 as seen in FIG. 10C. Once the depiction is displayed, the method 1400 reverts to stage 1406 then stage 1402, wherein zone report data are queried anew. In one embodiment, previously stored query data are disposed and new data are acquired.

If the answer at stage 1424 is "no," stage 1428 is executed, wherein the at least five zone reports are analyzed and at stage 1430, it is determined whether three or more of the zone reports are "high" zone reports, indicating that the distal tip of the stylet 130 has not yet arrived proximate the lower $1/3^{rd}$ portion 1354 of the SVC 1352 (as in zones −2, −1, or 0 of FIG. 12). If yes, a high state is declared at stage 1432, in which the system application 1218 will depict an appropriate indication on the display 30 (FIG. 2), for instance, indicating to the user that the catheter can be advanced further. In one embodiment, the depiction on the display 30 includes the yellow bullseye design of the stylet position icon 1328 as seen in FIG. 10A. Once the depiction is displayed, the method 1400 reverts to stage 1406 then stage 1402, wherein zone report data are queried anew. In one embodiment, previously stored query data are disposed and new data are acquired.

If the answer at stage 1430 is "no," stage 1434 is executed, wherein the at least five zone reports are analyzed and at stage 1436, it is determined whether four or more of the zone reports are "ideal" zone reports, indicating that the distal tip of the stylet 130 has arrived proximate the lower $1/3^{rd}$ portion 1354 of the SVC 1352 (as in zones +1 or +2 of FIG. 12). If yes, an ideal state is declared at stage 1438, in which the system application 1218 will depict an appropriate indication on the display 30 (FIG. 2), for instance, indicating to the user that the catheter has arrived at its intended destination according to the present embodiment. In one embodiment, the depiction on the display 30 includes the green diamond design of the stylet position icon 1328 as seen in FIG. 10B. Once the depiction is displayed, the method 1400 reverts to stage 1406 then stage 1402, wherein zone report data are queried anew. In one embodiment, previously stored query data are disposed and new data are acquired.

If the answer at stage 1436 is "no," stage 1440 is executed, wherein the at least five current zone reports are analyzed and a decision made at one or more of three stages 1440, 1442, and 1444. At stage 1440, if the previous zone determination on an immediately prior iteration of the method 1400 yielded an ideal state and three of the five current zone reports are low zone reports, then a low state is declared at stage 1426, which stage is executed as already described further above.

If the answer at stage 1440 is "no," stage 1442 is executed, wherein if the previous zone determination on the immediately prior iteration of the method 1400 yielded an ideal state and two or more of the five current zone reports are ideal zone reports, then an ideal state is declared at stage 1438, which stage is executed as already described further above.

If the answer at stage 1442 is "no," stage 1444 is executed, wherein if the previous zone determination on the immediately prior iteration of the method 1400 yielded a low state and two or more of the five current zone reports are low zone reports, then a low state is declared at stage 1426, which stage is executed as already described further above.

If the answer at stage 1444 is "no," a high state is declared at stage 1432, which stage is executed as described further above. Once the depiction is displayed pursuant stages 1426, 1432, or 1438, the method 1400 reverts to stage 1406 then stage 1402, wherein zone report data are queried anew. In one embodiment, previously stored query data are disposed and new data are acquired.

Note that the method 1400 is iteratively run during the medical device placement process using the system 10. Note also that the particular threshold numbers used in evaluating the zone reports can vary from what is described herein as may be appreciated by one skilled in the art. Also, more than three zone reports can be employed, in one embodiment.

Note that other modes for updating the display 30 according to zone information reported by the method 1200 can also be employed, including different icons or symbols or output modes, differently colored icons, etc. More generally, other reporting decision trees can be utilized to govern depiction of zone information from the method 1200 on the display 30 or other output mode by the system application 1218. In yet another embodiment, parameters other than zones can be reported by the method 1200.

Note that the stages 1260-1264 of the process 1224 can be performed simultaneously or in an order different than that shown in FIG. 6. Also, other parameters can be evaluated by the algorithm of the method 1200, including patient heart rate, isoelectric/baseline wander, and the uprightness of the detected QRS complex. For example, a patient heart rate threshold of between about 50 and about 150 beats per minute can be used as a parameter for evaluation by the method 1200 to ensure proper intravascular placement of the medical device. In another example, an allowable baseline wander of +/−about 300 microvolts at 2.5 Hertz can be used as a parameter. In yet another example, a QRS complex length between about 0.08 and about 0.10 seconds in duration can be used as a parameter. These and other suitable parameters can be employed. Generally, it is noted that more or fewer stages can be included in the method 1200 in other embodiments to assist in tracking and positioning the catheter or other suitable medical device.

Figure 11:
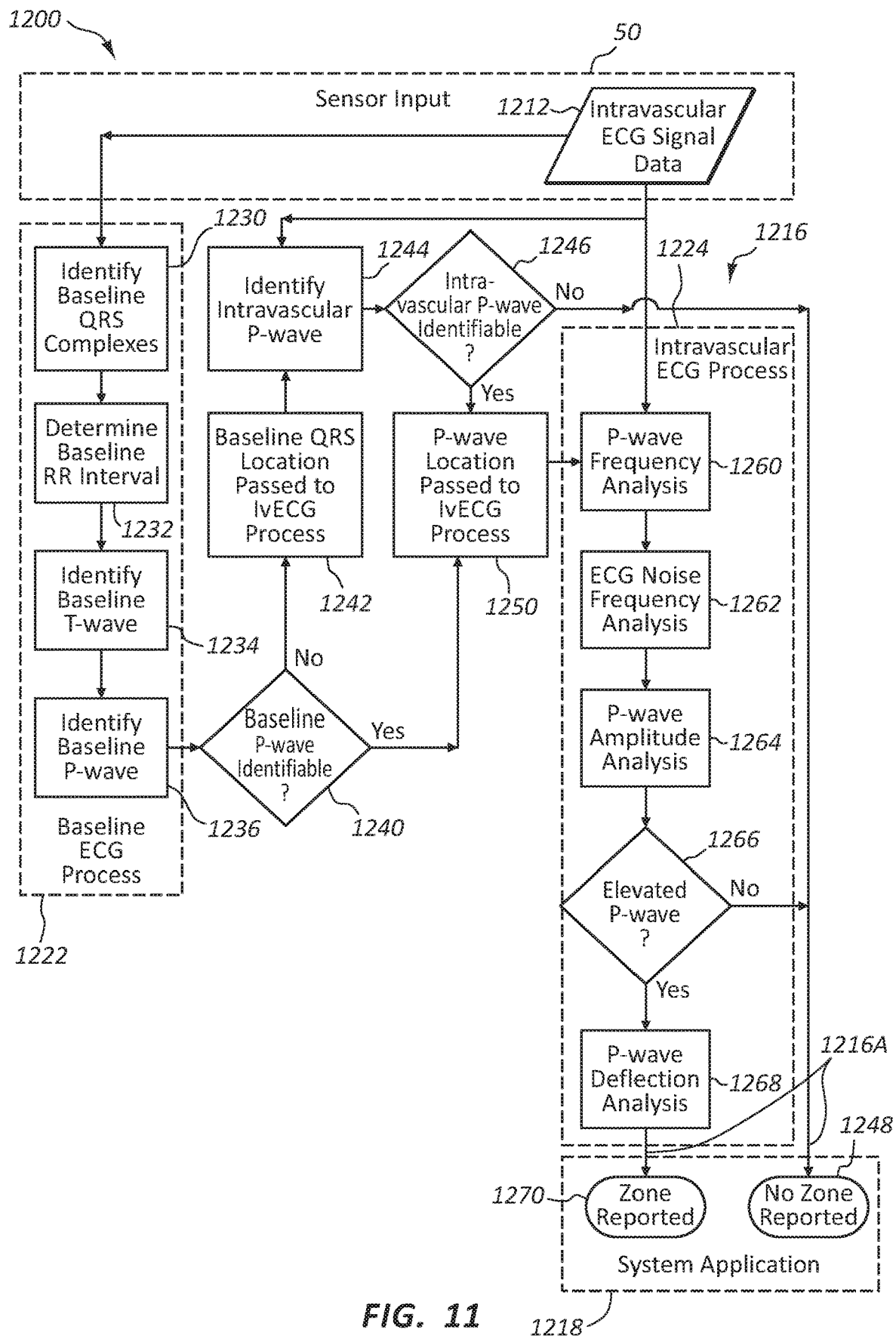
FIG. 11 is a block diagram showing various stages of a method for guiding a medical device according to one embodiment.

FIG. 11 shows the method 1200 according to another embodiment, wherein instead of both external and intravascular ECG sensor components used to determine P-wave maximum, only the intravascular ECG sensor component is employed. As such, no external electrodes, such as the external electrodes 136 (FIG. 2), are disposed on the skin of the patient. Instead, stages 1230, 1232, 1234, 1236, and 1240 are executed by using a baseline ECG signal. The baseline ECG signal is acquired using ECG signals detected by the stylet sensor assembly of the stylet 130 (i.e., the intravascular ECG sensor component). In particular, the baseline ECG signal is acquired from the stylet ECG sensor assembly of the stylet 130 when the stylet distal tip is disposed in the vasculature between the insertion site 73 (FIG. 2) and about the shoulder region of the arm into which the stylet and catheter 72 are inserted (i.e., the right arm in the example shown in FIG. 2). Note that, in another embodiment, the insertion site can be on another limb of the patient, such as the leg, in which case the baseline ECG signal is acquired from the stylet ECG sensor assembly when the stylet distal tip is disposed between the insertion site and the junction point of the limb (leg) with the torso of the patient.

Detection of ECG signals when the stylet sensor assembly is positioned as described immediately above (with the insertion site disposed on the arm of the patient) approximates the detection of ECG signals from a pair of external skin-placed electrodes in a "Lead II" configuration based on Einthoven's triangle. As such, the ECG signal so detected will remain substantially static and can be used as a baseline reference ECG signal against the intravascular ECG signal detected by the stylet sensor assembly when the stylet 130 is advanced past the general shoulder region of the arm into which the stylet and catheter are inserted. Such advancement will enable the stylet sensor assembly to detect the changing P-wave as the stylet nears the SA node of the patient heart 1350 (FIG. 12). Thus, in the present embodiment the stages 1230, 1232, 1234, 1236, and 1240 are executed similar to that described further above in connection with the description of FIG. 6 while using the baseline ECG signal (part of the intravascular ECG signal data 1212) detected by the stylet sensor assembly upon initial insertion of the catheter 72 and included stylet 130 into the vasculature but before advancement past the shoulder region of the arm into which the catheter and stylet are inserted.

Note that the use and analysis of a baseline and intravascular ECG signal that both originate from detection by an intravascular ECG sensor component (i.e., the stylet sensor assembly of the stylet 130) as described in connection with FIG. 11 enables in one embodiment the ability for a clinician to observe conditions that may be evident only in the intravascular ECG signal and not evident in an external ECG signal detected via an external ECG sensor component, such as the external electrodes 136 of FIG. 2. One example of such a condition includes intra-atrial blocks, for instance.

Embodiments disclosed herein may include a special purpose or general-purpose computer including computer hardware, as discussed in greater detail below. Embodiments within the scope of the present disclosure also include computer-readable media for carrying or having computer-executable instructions or data structures stored thereon. Such computer-readable media can be any available media that can be accessed by a general purpose or special purpose computer. By way of example, and not limitation, computer-readable media can comprise physical (or recordable-type) computer-readable storage media, such as, RAM, ROM, EEPROM, CD-ROM or other optical disk storage, solid-state storage, magnetic disk storage or other magnetic storage devices, or any other medium which can be used to store desired program code means in the form of computer-executable instructions or data structures and which can be accessed by a general purpose or special purpose computer.

In this description and in the following claims, a "network" is defined as one or more data links that enable the transport of electronic data between computer systems and/or modules. When information is transferred or provided over a network or another communications connection (either hardwired, wireless, or a combination of hardwired or wireless) to a computer, the computer properly views the connection as a computer-readable medium. Thus, by way of example, and not limitation, computer-readable media can also comprise a network or data links which can be used to carry or store desired program code means in the form of computer-executable instructions or data structures and which can be accessed by a general purpose or special purpose computer.

Computer-executable instructions include, for example, instructions and data which cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the embodiments herein may be practiced in network computing environments with many types of computer system configurations, including personal computers, desktop computers, laptop computers, message processors, hand-held devices, multi-processor systems, microprocessor-based or programmable consumer electronics, network PCs, minicomputers, mainframe computers, mobile telephones, PDAs, pagers, and the like. The embodiments may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A method for guiding a medical device in a patient, comprising: inserting the medical device in the patient; using a tracking system to advance the medical device toward an intended destination in the patient; and positioning the medical device at the intended destination, the positioning comprising:
    detecting an intravascular ECG signal of the patient;
    identifying a P-wave of a waveform of the intravascular ECG signal;
    determining whether the identified P-wave is elevated by analyzing a frequency of the identified P-wave and comparing the frequency to a predetermined threshold value;
    determining a deflection value of the identified P-wave when the frequency of the identified P-wave meets or exceeds the predetermined threshold value; and
    reporting information relating to a location of the medical device in the patient at least partially according to the determined deflection value of the identified P wave.

2. The method for guiding according to claim 1, further comprising:
    detecting an external ECG signal of the patient;
    identifying an external P-wave of a waveform of the external ECG signal; and
    using the identified external P-wave in identifying the P-wave of the intravascular ECG signal.

3. The method for guiding according to claim 2, wherein identifying the external P-wave further includes:
    identifying a QRS complex of the waveform of the external ECG signal;
    identifying a T-wave of the waveform of the external ECG signal; and
    determining a RR interval between successive waveforms of the external ECG signal.

4. The method for guiding according to claim 3, wherein the external ECG signal is detected by a pair of external electrodes placed on a skin of the patient.

5. The method for guiding according to claim 1, wherein the intravascular ECG signal is detected by a sensor component included with a stylet removably received within the medical device.

6. The method for guiding according to claim 1, wherein the steps of identifying the P-wave, determining whether the identified P-wave is elevated, and determining the deflection value are executed by a processor of a system operably connected with the medical device.

7. The method for guiding according to claim 6, wherein the steps of identifying the P-wave, determining whether the identified P-wave is elevated, and determining the deflection value are executed iteratively by the processor.

8. The method for guiding according to claim 1, wherein the step of reporting information relating to the location of the medical device includes reporting one of a plurality of zones, each of the plurality of zones relating to a proximity of the medical device to a signal-emitting node of a heart of the patient.

9. The method for guiding according to claim 1, wherein the step of reporting information relating to the location of the medical device includes outputting the information to at least one of an audio device and a display device.

10. The method for guiding according to claim 1, wherein the step of reporting information relating to the location of the medical device includes outputting graphical information to a display device of a placement system for the medical device.

11. The method for guiding according to claim 10, wherein the graphical information includes a plurality of icons that correspond to a proximity of the medical device to a signal-emitting node of a heart of the patient.

12. A method for guiding a medical device in a patient, comprising:
    detecting an intravascular ECG signal of a signal-emitting portion of a heart of the patient by an intravascular ECG sensor component included with the medical device; and
    determining whether a P-wave of a waveform of the intravascular ECG signal is elevated based on a plurality of predetermined thresholds, the P-wave varying according to a distance of the intravascular ECG sensor component from the signal-emitting portion of the heart, the predetermined thresholds relating to at least one of:
        (a) an amplitude of the P-wave of the intravascular ECG signal within a predetermined range;
        (b) a slope of the P-wave of the intravascular ECG signal within a predetermined range; and
        (c) a noise component of the intravascular ECG signal within a predetermined range.

13. The method for guiding according to claim 12, further comprising:
    determining a deflection value of the P-wave when the P-wave is elevated; and
    reporting information relating to a location of the medical device in the patient at least partially according to the determined deflection value of the P-wave.

14. The method for guiding according to claim 12, wherein the steps of detecting the intravascular ECG signal, determining whether the P-wave is elevated, and determining the deflection value are performed iteratively.

15. A system for guiding a medical device in a patient, comprising: a tracking system for advancing the medical device toward an intended destination in the patient:
    an intravascular ECG sensor for positioning the medical device at the intended destination, the intravascular ECG sensor designed to detect an intravascular ECG signal of the patient;
    a processor designed to:
        receive the intravascular ECG signal;

identify a P-wave of a waveform of the intravascular ECG signal;

determine whether the identified P-wave is elevated by analyzing a frequency of the identified P-wave and comparing the frequency to a predetermined threshold value;

determine a deflection value of the identified P-wave when the frequency of the identified P-wave meets or exceeds the predetermined threshold value; and report information relating to a location of the medical device in the patient at least partially according to the determined deflection value of the identified P wave; and an output device designed to display the information relating to the location of the medical device.

16. The system for guiding according to claim 15, wherein the processor designed to determine whether the identified P-wave is elevated is further designed to analyze:

an amplitude of the identified P-wave to determine whether the amplitude falls within a predetermined range; and a noise component of the intravascular ECG signal to determine whether the noise component falls within a predetermined range.

17. The system for guiding according to claim 15, wherein the processor is designed to execute a decision tree determining when to report the information relating to the location of the medical device.

18. The system for guiding according to claim 17, wherein the system further includes at least one of a magnet tracking modality and an ultrasound imaging modality.

19. In a guidance system including a medical device for insertion into a patient, an external ECG sensor component, and an intravascular ECG sensor component included with the medical device, a method for guiding the medical device, comprising:

(a) identifying a P-wave from a waveform of an intravascular ECG signal from the intravascular ECG sensor component after insertion of the medical device into the patient;

(b) determining whether at least one of a frequency and an amplitude of the identified P-wave falls within a predetermined range;

(c) determining whether a noise component of the intravascular ECG signal falls within a predetermined range; and (d) determining whether the identified P-wave is at an elevated state based upon the determinations of stages (b) and (c).

20. The method for guiding according to claim 19, further comprising:

(e) determining a deflection value for the identified P-wave when the identified P-wave is at an elevated state as determined in stage (d).

21. The method for guiding as defined in claim 20, further comprising:

(f) depicting a position of the medical device based on the deflection value as determined in stage (e).

22. The method for guiding according to claim 21, wherein a processor of the system executes a decision tree, determining an aspect of depicting the position of the medical device.

23. The method for guiding according to claim 22, wherein the decision tree iteratively queries a data set of a plurality of zone reports until at least 50 zone reports are acquired.

24. The method for guiding according to claim 22, wherein the processor depicts the position of the medical device when at least three of five zone reports from the data set are identical.

25. The method for guiding according to claim 19, further comprising:

(e) identifying an external P-wave of a waveform of an external ECG signal from the external ECG sensor component; and (f) using the identified external P-wave to identify the P-wave of the intravascular ECG signal in stage (a).

* * * * *